US006794396B2

(12) United States Patent
Lee et al.

(10) Patent No.: US 6,794,396 B2
(45) Date of Patent: *Sep. 21, 2004

(54) SUBSTITUTED PYRIDINES USEFUL FOR INHIBITING CHOLESTERYL ESTER TRANSFER PROTEIN ACTIVITY

(75) Inventors: Len F. Lee, St. Charles, MO (US); Kevin C. Glenn, Maryland Heights, MO (US); Daniel T. Connolly, Manchester, MO (US); David G. Corley, Prangias (CH); Daniel L. Flynn, Natick, MA (US); Ashton T. Hamme, Ridgeland, MS (US); Shridhar G. Hegde, Ballwin, MO (US); Michele A. Melton, Bridgeton, MO (US); Roger J. Schilling, St. Louis, MO (US); James A. Sikorski, Atlanta, GA (US); Nancy N. Wall, Florissant, MO (US); Jeffery A. Zablocki, Mountain View, CA (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/403,903

(22) Filed: Mar. 31, 2003

(65) Prior Publication Data

US 2004/0038939 A1 Feb. 26, 2004

Related U.S. Application Data

(62) Division of application No. 09/600,870, filed as application No. PCT/US99/01871 on Feb. 11, 1999, now Pat. No. 6,605,624.
(60) Provisional application No. 60/074,586, filed on Feb. 13, 1998.

(51) Int. Cl.[7] .................. C07D 213/02; C07D 401/02; A61K 31/44
(52) U.S. Cl. ................ 514/333; 514/332; 514/345; 514/350; 514/354; 546/262; 546/369.7; 546/290; 546/294; 546/298; 546/301; 546/326
(58) Field of Search .................. 514/332, 354, 514/345, 350, 333; 546/262, 326, 269.7, 294, 298, 290, 301

(56) References Cited

U.S. PATENT DOCUMENTS

| 4,439,607 A | 3/1984 | Drabb ................. 546/89 |
| 4,609,399 A | 9/1986 | Lee ..................... 71/94 |
| 4,655,816 A | 4/1987 | Lee ..................... 71/86 |
| 4,692,184 A | 9/1987 | Lee ..................... 71/94 |
| 4,698,093 A | 10/1987 | Lee et al. ............. 71/94 |
| 4,789,395 A | 12/1988 | Lee et al. ............. 71/94 |
| 4,885,026 A | 12/1989 | Lee et al. ............. 71/94 |
| 4,925,852 A | 5/1990 | Kesseler et al. ....... 514/333 |
| 4,936,905 A | 6/1990 | Miller et al. .......... 71/94 |
| 4,988,384 A | 1/1991 | Sing et al. ............ 71/94 |
| 5,037,469 A | 8/1991 | Hegde et al. ........... 71/94 |
| 5,125,956 A | 6/1992 | Korte et al. ........... 71/90 |
| 5,125,961 A | 6/1992 | Auinbauh et al. ....... 71/94 |
| 5,129,943 A | 7/1992 | Hegde et al. ........... 71/94 |
| 5,156,670 A | 10/1992 | Lee et al. ............. 71/94 |
| 5,169,432 A | 12/1992 | Auinbauh et al. ....... 71/94 |
| 5,169,857 A | 12/1992 | Angerbauer et al. .... 514/344 |
| 5,260,262 A | 11/1993 | Lee et al. ............. 504/252 |
| 5,519,001 A | 5/1996 | Kushwaha et al. ...... 514/12 |
| 5,925,645 A * | 7/1999 | Schmidt et al. ........ 514/277 |
| 6,605,624 B1 | 8/2003 | Lee et al. ............. 514/332 |

FOREIGN PATENT DOCUMENTS

| EP | 0 133 612 A2 | 2/1985 | ......... C07D/213/80 |
| EP | 0 135 491 B1 | 3/1985 | ......... A01N/43/40 |
| EP | 0 181 852 B1 | 5/1986 | ......... C07D/213/80 |
| EP | 0 182 769 B1 | 5/1986 | ......... C07D/213/80 |
| EP | 0 245 230 A1 | 11/1987 | ......... C07D/213/80 |
| EP | 0 252 055 B1 | 1/1988 | ......... C07D/213/80 |
| EP | 0 276 204 A2 | 7/1988 | ......... A01N/57/16 |
| EP | 0 278 944 B1 | 8/1988 | ......... C07D/401/04 |
| EP | 0 278 945 B1 | 8/1988 | ......... C07D/401/06 |
| EP | 0 278 945 A3 | 8/1988 | ......... C07D/401/06 |
| EP | 0 435 843 B1 | 7/1991 | ......... C07D/405/12 |
| EP | 0 435 843 A1 | 7/1991 | ......... C07D/405/12 |
| EP | 0 796 846 A1 | 9/1997 | ......... C07D/213/30 |
| EP | 0 818 197 A1 | 1/1998 | ......... A61K/31/435 |
| WO | WO 92/20659 | 11/1992 | ......... C07D/213/80 |
| WO | WO 92/21674 | 12/1992 | ......... C07D/401/06 |
| WO | WO 93/11112 | 6/1993 | ......... C07D/213/80 |
| WO | WO 98/04528 | 2/1998 | ......... C07D/213/20 |
| WO | WO 98/34895 | 8/1998 | ........... C07C/33/50 |
| WO | WO 98/35937 | 8/1998 | ......... C07C/323/40 |

OTHER PUBLICATIONS

Barrett et al., *Total synthesis and sterochemical assignment of the quinquecyclopropane–cantaining cholesteryl ester transfer protein inhibitor U–106305*, J. Am. Chem. Soc., 188:7863–64 (1996).

Barter et al., *High density lipoproteins and coronary heart disease*, Atherosclerosis, 121(1)1–12 (1996).

(List continued on next page.)

Primary Examiner—Zinna Northington Davis
(74) Attorney, Agent, or Firm—Harness, Dickey & Pierce, P.L.C.

(57) ABSTRACT

(IA)

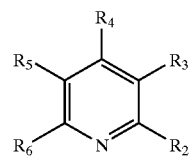

A class of substituted pyridines that are useful for inhibiting the activity of cholesteryl ester transfer protein, and have the structural formula (IA), wherein $R_2$, $R_3$, $R_4$, $R_5$, and $R_6$ are defined in the claims.

14 Claims, No Drawings

OTHER PUBLICATIONS

Bisgaier et al., *Cholesteryl ester transfer protein inhibition by PD 140195*, Lipids, 29(12):811–818 (1994).

Busch et al., *Cholesteryl ester analogs inhibit cholesteryl ester but not triglyceride transfer catalyzed by the plasma cholesteryl ester–triglyceride transfer protein*, Lipids, 25(4):216–220 (1990).

Connolly et al., *Inactivation of cholesteryl ester transfer protein by cysteine modification*, Biochem. Biophys. Res. Comm., 223:42–47 (1996).

Coval et al., *Wiedendiol–A and –B, cholesteryl ester transfer protein inhibitors from the marine sponge xestospongia wiedenmayeri*, Bioorg. Med. Chem. Lett., 5(6):605–610 (1995).

Hegde, S. H., *Selective ether cleavage reactions of 4,6–dialkoxy–2–(trifluoromethyl)pyridine mono– and dicarbxylates*, J. Org. Chem., 56(16):5726–5729 (1991).

Lee et al., *A Cholesteryl ester transfer protein inhibitor from an insect–associated fungus*, J. Antobiotics, 49(7):693–96 (1996).

Lee et al., *A novel dehydrofluorination of 2–(trifluoromethyl)dihydro–3,5–pyridinecarboxylates to 2–(difluoromethyl)–3,5–pyridinedicarboxylates*, J.Org. Chem., 55(9):2872–2877 (1990).

Lee et al., *Synthesis of 2,4–dialkoxy–6–(trifluoromethyl)–3, 5–pyridinedicarboxylates via a novel cyclocondensation of dialkyl 3–oxopentanedionates with trifluoroacetonitrile*, J.Org. Chem., 55(9):2964–2967 (1990).

McCarthy, P.A., *New approaches to atherosclerosis: an overview*, Med. Red. Revs., 13(2):139–159 (1993).

Morton et al., *Purification and characterization of lipid transfer protein(s) from human lipoprotein–deficient plasma*, J. Lipid Res., 23:1058–1067 (1982).

Pietzonka et al., *Phosphonate–containing analogs of cholesteryl ester as novel inhibitors of cholesteryl ester transfer protein*, Bioorg. Med. Chem. Lett., 6(16):1951–54 (1996).

Son et al., *Purification and characterization of human plasma proteins that inhibit lipid transfer activites*, Biochim. Biophys. Acta, 795:473–480 (1984).

Swenson et al., *Mechanism of cholesteryl ester transfer protein inhibition by a neutralizing monoclonal antibody and mapping of the monoclonal antibody epitope*, J. Biol. Chem., 264(24):14318–14326 (1989).

Tall, A. R., *PLasma cholesteryl ester transfer protein*, J. Lipid Res., 34:1255–1274 (1993).

* cited by examiner

SUBSTITUTED PYRIDINES USEFUL FOR INHIBITING CHOLESTERYL ESTER TRANSFER PROTEIN ACTIVITY

CROSS-REFERENCE TO RELATED PATENT APPLICATIONS

This patent is a divisional of U.S. patent application Ser. No. 09/600,870 (filed Dec. 11, 2000, now U.S. Pat. No. 6,605,624 which, in turn, claims priority to International Patent Application No. PCT/US99/01871 (filed on Feb. 11, 1999; and published as International Publication No. WO 99/41237), which, in turn, claims priority to U.S. Provisional Patent Application Serial No. 60/074,586 (filed February 13, 1998). This patent also claims priority to U.S. Provisional Patent Application Serial No. 60/074,586. The entire text of each of the above-referenced patent applications is incorporated by reference into this patent.

FIELD OF THE INVENTION

This invention is in the field of preventing and/or treating cardiovascular disease, and specifically relates to compounds, compositions and methods for preventing and/or treating atherosclerosis and other coronary artery disease. More particularly, the invention relates to substituted pyridine compounds that inhibit cholesteryl ester transfer protein (CETP), also known as plasma lipid transfer protein-I.

BACKGROUND OF THEN INVENTION

Numerous studies have demonstrated that a low plasma concentration of high density lipoprotein (HDL) cholesterol is a powerful risk factor for the development of atherosclerosis (Barter and Rye, *Atherosclerosis*, 121, 1–12 (1996)). HDL is one of the major classes of lipoproteins that function in the transport of lipids through the blood. The major lipids found associated with HDL include cholesterol, cholesteryl ester, triglycerides, phospholipids and fatty acids. The other classes of lipoproteins found in the blood are low density lipoprotein (LDL) and very low density lipoprotein (VLDL). Since low levels of HDL cholesterol increase the risk of atherosclerosis, methods for elevating plasma HDL cholesterol would be therapeutically beneficial for the treatment of atherosclerosis and other diseases associated with accumulation of lipid in the blood vessels. These diseases include, but are not limited to, coronary heart disease, peripheral vascular disease, and stroke.

Atherosclerosis underlies most coronary artery disease (CAD), a major cause of morbidity and mortality in modern society. High LDL cholesterol (above 180 mg/dl) and low HDL cholesterol (below 35 mg/dl) have been shown to be important contributors to the development of atherosclerosis. Other diseases, such as peripheral vascular disease, stroke, and hypercholesterolaemia are negatively affected by adverse HDL/LDL ratios. Inhibition of CETP by the subject compounds are shown to effectively modify plasma HDL/LDL ratios, and to check the progress and/or formation of these diseases.

CETP is a plasma protein that facilitates the movement of cholesteryl esters and triglycerides between the various lipoproteins in the blood (Tall, *J. Lipid Res.*, 34, 1255–74 (1993)). The movement of cholesteryl ester from HDL to LDL by CETP has the effect of lowering HDL cholesterol. It therefore follows that inhibition of CETP should lead to elevation of plasma HDL cholesterol and lowering of plasma LDL cholesterol, thereby providing a therapeutically beneficial plasma lipid profile (McCarthy, *Medicinal Res. Revs.*, 13, 139–59 (1993)). This exact phenomenon was first demonstrated by Swenson et al., (*J. Biol. Chem.*, 264, 14318 (1989)) with the use of a monoclonal antibody that specifically inhibited CETP. In rabbits, the antibody caused an elevation of the plasma HDL cholesterol and a decrease in LDL cholesterol. Son et al. (*Biochim. Biophys. Acta* 795, 743–480 (1984)) describes proteins from human plasma that +inhibit CETP. U.S. Pat. No. 5,519,001, issued to Kushwaha et al., describes a 36 amino acid peptide derived from baboon apo C-1 that inhibits CETP activity.

There have been several reports of compounds that act as CETP inhibitors. Barrett et al. (*J. Am. Chem. Soc.*, 188, 7863–63 (1996)) describes cyclopropane-containing CETP inhibitors. Pietzonka et al. (*Bioorg. Med. Chem. Lett*, 6, 1951–54 (1996)) describe phosphonate-containing analogs of cholesteryl ester as CETP inhibitors. Coval et al. (*Bioorg. Med. Chem. Lett.*, 5, 605–610 (1995)) describe Wiedendiol-A and -B, and related sesquiterpene compounds, as CETP inhibitors. Lee et al. (*J. Antibiotics*, 49, 693–96 (1996)) describe CETP inhibitors derived from an insect fungus. Busch et al. (*Lipids*, 25, 216–220, (1990)) describe cholesteryl acetyl bromide as a CETP inhibitor. Morton and Zilversmit (*J. Lipid Res.*, 35, 836–47 (1982)) describe that p-chloromercuriphenyl sulfonate, p-hydroxymercuribenzoate and ethyl mercurithiosalicylate inhibit CETP. Bisgaier et al. (*Lipids*, 29, 811–8 (1994) describe 4-phenyl-5-tridecyl-4H-1,2,4-triazole-thiol as a CETP inhibitor.

A number of substituted pyridine compounds are known. For example, U.S. Pat. Nos. 4,609,399, 4,655,816; 4,692, 184; 4,698,093; 4,789,395; 4,885,026; 4,936,905; 4,988, 384; 5,037,469; 5,125,961; 5,129,943; 5,156,670; 5,169, 432; and 5,260,262 each disclose novel substituted pyridines which are useful as herbicides and herbicide intermediates. No pharmacologic properties for the substituted pyridines are recited in these patents. Except as set forth below, the literature does not describe substituted pyridines as inhibitors of CETP.

Connolly et al. (*Biochem. Biophys. Res. Comm.* 223, 42–47 (1996)), describe 4,4'-dithiopyridine, 2,2'-dithiopyridine, 6,6'-dithionicotinic acid and 2,2'-dithiobis (pyridine-N-oxide) as CTEP inhibitors. The isolated pyridine compounds tested by Connolly et al. were, at best, inhibitory only after a 16 hour pre-incubation period and would not be useful in situations requiring rapid and potent inhibition. Connolly et al. also neither addressed whether substitution of the reported pyridines would increase their potency nor suggested the testing or use of specific substituted pyridines.

European Patent Application 796 846 A1 describes certain 2-aryl-substituted pyridines for use in the treatment of lipoproteinaemia and hyperlipoproteinaemia.

European Patent Application 818 197 A1 describes certain 2-aryl-substituted pyridines for use in the treatment of hyperlipoproteinaemia and atherosclerosis.

U.S. Pat. No. 4,925,852 describes 3-demethylmevalonic acid derivatives for use as inhibitors of cholesterol biosynthesis.

U.S. Pat. No. 5,169,857 describes 7-(polysubstituted pyridyl)-hept-6-endates for use in the treatment of hyperproteinaemia, lipoproteinaemia or arteriosclerosis.

WO 98/04528 describes certain 4-aryl-pyridyl compounds as anti-hypercholesterolemic, anti-hyperlipoproteinemic and anti-hyperglycemic agents.

SUMMARY OF THE INVENTION

The present invention is directed to a method for administering to a subject a therapeutically effective amount of a substituted pyridine of Formula I:

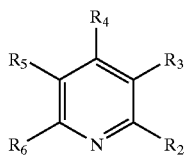
(I)

wherein:

$R_2$ and $R_6$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of $R_2$ and $R_6$ is fluorinated alkyl, chlorofluorinated alkyl or alkoxyalkyl;

$R_3$ is selected from the group consisting of hydroxy, amido, arylcarbonyl, heteroarylcarbonyl, hydroxymethyl,

—CHO,

—CO$_2$R$_7$, wherein R$_7$ is selected from the group consisting of hydrogen, alkyl and cyanoalkyl; and

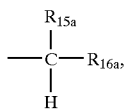

wherein $R_{15a}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy and heterocyclyloxy, and $R_{16a}$ is selected from the group consisting of alkyl, haloalkyl, alkenyl, haloalkenyl, alkynyl, haloalkynyl, aryl, heteroaryl, and heterocyclyl, arylalkoxy, trialkylsilyloxy;

$R_4$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkoxy, alkenoxy, alkynoxy, aryloxy, heteroaryloxy, heterocyclyloxy, alkanoyloxy, alkenoyloxy, alkynoyloxy, aryloyloxy, heteroaroyloxy, heterocyclyloyloxy, alkoxycarbonyl, alkenoxycarbonyl, alkynoxycarbonyl, aryloxycarbonyl, heteroaryloxycarbonyl, heterocyclyloxycarbonyl, thio, alkylthio, alkenylthio, alkynylthio, arylthio, heteroarylthio, heterocyclylthio, cycloalkylthio, cycloalkenylthio, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkylamino, alkenylamino, alkynylamino, arylamino, heteroarylamino, heterocyclylamino, aryldialkylamino, diarylamino, diheteroarylamino, alkylarylamino, arylheteroarylamino, arylheteroarylamino, trialkylsilyl, trialkenylsilyl, triarylsilyl, —OC(O)N(R$_{8a}$R$_{8b}$), wherein R$_{8a}$ and R$_{8b}$ are independently selected from the group consisting of alkyl, alkenyl, alkynyl, aryl, heteroaryl and heterocyclyl, —SO$_2$R$_9$, wherein R$_9$ is selected from the group consisting of hydroxy, alkyl, alkenyl, alkynyl, aryl, heteroaryl and heterocyclyl, —OP(O) (OR$_{10a}$) (OR$_{10b}$), wherein R$_{10a}$ and R$_{10b}$ are independently selected from the group consisting of hydrogen, hydroxy, alkyl, alkenyl, alkynyl, aryl, heteroaryl and heterocyclyl, and —OP(S) (OR$_{11a}$) (OR$_{11b}$), wherein R$_{11a}$ and R$_{11b}$ are independently selected from the group consisting of alkyl, alkenyl, alkynyl, aryl, heteroaryl and heterocyclyl;

$R_5$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, alkoxy, alkenoxy, alkynoxy, aryloxy, heteroaryloxy, heterocyclyloxy, alkylcarbonyloxyalkyl, alkenylcarbonyloxyalkyl, alkynylcarbonyloxyalkyl, arylcarbonyloxyalkyl, heteroarylcarbonyloxyalkyl, heterocyclylcarbonyloxyalkyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, cycloalkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkoxyalkyl, alkenoxyalkyl, alkynoxyalkyl, aryloxyalkyl, heteroaryloxyalkyl, heterocyclyloxyalkyl, alkoxyalkenyl, alkenoxyalkenyl, alkynoxyalkenyl, aryloxyalkenyl, heteroaryloxyalkenyl, heterocyclyloxyalkenyl, cyano, hydroxymethyl,

—CO$_2$R$_{14}$, wherein $R_{14}$ is selected from the group consisting of alkyl, alkenyl, alkynyl, aryl, heteroaryl and heterocyclyl;

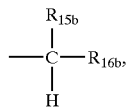

wherein $R_{15b}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy, heterocyclyloxy, aroyloxy, and alkylsulfonyloxy, and $R_{16b}$ is selected from the group consisting of alkyl, alkenyl, alkynyl, aryl, heteroaryl, heterocyclyl, arylalkoxy, and trialkylsilyloxy;

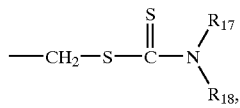

wherein $R_{17}$ and $R_{18}$ are independently selected from the group consisting of alkyl, cycloalkyl, alkenyl, alkynyl, aryl, heteroaryl and heterocyclyl;

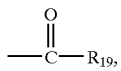

wherein $R_{19}$ is selected from the group consisting of alkyl, cycloalkyl, alkenyl, alkynyl, aryl, heteroaryl, heterocyclyl, —$SR_{20}$, —$OR_{21}$, and —$R_{22}CO_2R_{23}$, wherein $R_{20}$ is selected from the group consisting of alkyl, alkenyl, alkynyl, aryl, heteroaryl, heterocyclyl, aminoalkyl, aminoalkenyl, aminoalkynyl, aminoaryl, aminoheteroaryl, aminoheterocyclyl, alkylheteroarylamino, arylheteroarylamino, $R_{21}$ is selected from the group consisting of alkyl, alkenyl, alkynyl, aryl, heteroaryl, and heterocyclyl, $R_{22}$ is selected from the group consisting of alkylene or arylene, and $R_{23}$ is selected from the group consisting of alkyl, alkenyl, alkynyl, aryl, heteroaryl, and heterocyclyl;

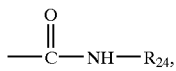

wherein $R_{24}$ is selected from the group consisting of hydrogen, alkyl, cycloalkyl, alkenyl, alkynyl, aryl, heteroaryl, heterocyclyl, aralkyl, aralkenyl, and aralkynyl;

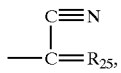

wherein $R_{25}$ is heterocyclylidenyl;

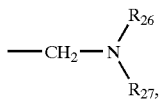

wherein $R_{26}$ and $R_{27}$ are independently selected from the group consisting of hydrogen, alkyl, cycloalkyl, alkenyl, alkynyl, aryl, heteroaryl, and heterocyclyl;

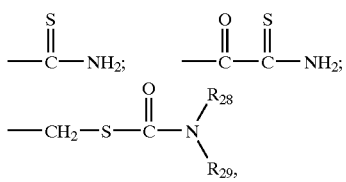

wherein $R_{28}$ and $R_{29}$ are independently selected from the group consisting of hydrogen, alkyl, cycloalkyl, alkenyl, alkynyl, aryl, heteroaryl, and heterocyclyl;

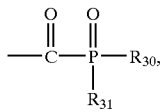

wherein $R_{30}$ and $R_{31}$ are independently alkoxy, alkenoxy, alkynoxy, aryloxy, heteroaryloxy, and heterocyclyloxy;

and

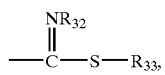

wherein $R_{32}$ and $R_{33}$ are independently selected from the group consisting of hydrogen, alkyl, cycloalkyl, alkenyl, alkynyl, aryl, heteroaryl, and heterocyclyl;

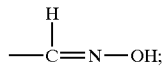

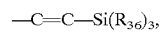

wherein $R_{36}$ is selected from the group consisting of alkyl, alkenyl, aryl, heteroaryl and heterocyclyl;

wherein $R_{37}$ and $R_{38}$ are independently selected from the group consisting of hydrogen, alkyl, cycloalkyl, alkenyl, alkynyl, aryl, heteroaryl, and heterocyclyl;

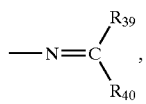

wherein $R_{39}$ is selected from the group consisting of hydrogen, alkoxy, alkenoxy, alkynoxy, aryloxy, heteroaryloxy, heterocyclyloxy, alkylthio, alkenylthio, alkynylthio, arylthio, heteroarylthio and heterocyclylthio, and $R_{40}$ is selected from the group consisting of haloalkyl, haloalkenyl, haloalkynyl, haloaryl, haloheteroaryl, haloheterocyclyl, cycloalkyl, cycloalkenyl, heterocyclylalkoxy, heterocyclylalkenoxy, heterocyclylalkynoxy, alkylthio, alkenylthio, alkynylthio, arylthio, heteroarylthio and heterocyclylthio;

wherein $R_{41}$ is heterocyclylidenyl;

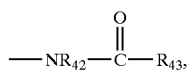

wherein $R_{42}$ is selected from the group consisting of hydrogen, alkyl, alkenyl, alkynyl, aryl, heteroaryl, and heterocyclyl, and $R_{43}$ is selected from the group consisting of hydrogen, alkyl, alkenyl, alkynyl, aryl, heteroaryl, heterocyclyl, cycloalkyl, cycloalkenyl, haloalkyl, haloalkenyl, haloalkynyl, haloaryl, haloheteroaryl, and haloheterocyclyl;

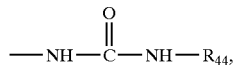

wherein $R_{44}$ is selected from the group consisting of hydrogen, alkyl, cycloalkyl, alkenyl, alkynyl, aryl, heteroaryl and heterocyclyl;

—N=S=O;

—N=C=S;

—N=C=O;

—N$_3$;

—SR$_{45}$, wherein $R_{45}$ is selected from the group consisting of hydrogen, alkyl, alkenyl, alkynyl, aryl, heteroaryl, heterocyclyl, haloalkyl, haloalkenyl, haloalkynyl, haloaryl, haloheteroaryl, haloheterocyclyl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, aminocarbonylalkyl, aminocarbonylalkenyl, aminocarbonylalkynyl, aminocarbonylaryl, aminocarbonylheteroaryl, and aminocarbonylheterocyclyl, —SR$_{46}$, and —CH$_2$R$_{47}$, wherein $R_{46}$ is selected from the group consisting of alkyl, alkenyl, alkynyl, aryl, heteroaryl and heterocyclyl, and $R_{47}$ is selected from the group consisting of hydrogen, alkyl, alkenyl, alkynyl, aryl, heteroaryl and heterocyclyl; and

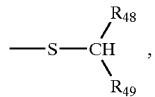

wherein $R_{48}$ is selected from the group consisting of hydrogen, alkyl, cycloalkyl, alkenyl, alkynyl, aryl, heteroaryl and heterocyclyl, and $R_{49}$ is selected from the group consisting of alkoxy, alkenoxy, alkynoxy, aryloxy, heteroaryloxy, heterocyclyloxy, haloalkyl, haloalkenyl, haloalkynyl, haloaryl, haloheteroaryl and haloheterocyclyl;

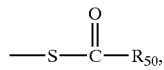

wherein $R_{50}$ is selected from the group consisting of hydrogen, alkyl, cycloalkyl, alkenyl, alkynyl, aryl, heteroaryl, heterocyclyl, alkoxy, alkenoxy, alkynoxy, aryloxy, heteroaryloxy and heterocyclyloxy;

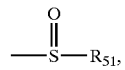

wherein $R_{51}$ is selected from the group consisting of alkyl, alkenyl, alkynyl, aryl, heteroaryl, heterocyclyl, haloalkyl, haloalkenyl, haloalkynyl, haloaryl, haloheteroaryl and haloheterocyclyl; and

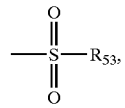

wherein $R_{53}$ is selected from the group consisting of alkyl, alkenyl, alkynyl, aryl, heteroaryl and heterocyclyl;

or a pharmaceutically acceptable salt or tautomer thereof, provided that when $R_5$ is selected from the group consisting of heterocyclylalkyl and heterocyclylalkenyl, then the heterocyclyl radical of the corresponding heterocyclylalkyl or heterocyclylalkenyl is other than a δ-lactone; and provided that when $R_4$ is aryl, heteroaryl or heterocyclyl, and one of $R_2$ and $R_6$ is trifluoromethyl, then the other of $R_2$ and $R_6$ is difluoromethyl.

In another embodiment, the method involves the administration of a therapeutically effective amount of a substituted pyridine of Formula IA wherein:

(IA)

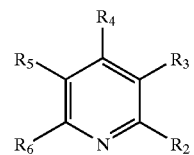

$R_2$ and $R_6$ are independently selected from the group consisting of hydrogen, hydroxy, alkyl, fluorinated alkyl, chlorofluorinated alkyl, cycloalkyl, heterocyclyl, aryl, heteroaryl, alkoxy, alkoxyalkyl, and alkoxycarbonyl; provided that at least one of $R_2$ and $R_6$ is fluorinated alkyl, chlorofluorinated alkyl or alkoxyalkyl;

$R_3$ is selected from the group consisting of hydroxy, amido, arylcarbonyl, heteroarylcarbonyl, hydroxymethyl,

—CO$_2$R$_7$, wherein $R_7$ is selected from the group consisting of hydrogen, alkyl and cyanoalkyl; and

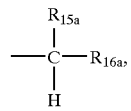

wherein $R_{15a}$ is selected from the group consisting of hydroxy, halogen, alkylthio and alkoxy, and $R_{16a}$ is selected from the group consisting of alkyl, aryl and heteroaryl;

$R_4$ is selected from the group consisting of hydrogen, hydroxy, halogen, alkyl, cycloalkyl, haloalkyl, alkenyl, aryl, heteroaryl, cycloalkylalkyl, heteroarylalkyl, aralkenyl, alkoxy, aralkoxy, alkoxycarbonyl, arylcarbonyloxy, thio, alkylthio, arylthio, cycloalkylthio, heterocyclylthio, alkylthioalkyl, alkylamino, trialkylsilyl, —OC(O)N($R_8$)$_2$, wherein $R_8$ is aryl, —SO$_2$$R_9$, wherein $R_9$ is aryl, —OP(O) (O$R_{10}$)$_2$, wherein $R_{10}$ is alkyl, and —OP(S) (O$R_{11}$)$_2$, wherein $R_{11}$ is alkyl;

$R_5$ is selected from the group consisting of hydrogen, hydroxy, halogen, alkyl, haloalkyl, alkynyl, heterocyclyl, heteroaryl, alkoxy, aryloxy, arylcarbonyloxyalkyl, heterocyclylalkyl, alkylthioalkyl, arylthioalkyl, heteroarylthioalkyl, alkoxyalkenyl, cyano, hydroxymethyl,

—CO$_2$$R_{14}$, wherein $R_{14}$ is alkyl;

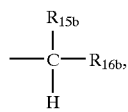

wherein $R_{15b}$ is selected from the group consisting of hydroxy, hydrogen, halogen, alkylthio and alkoxy, and $R_{16b}$ is selected from the group consisting of alkyl, aryl and heteroaryl;

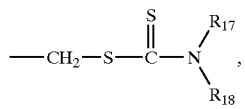

wherein $R_{17}$ and $R_{18}$ are independently alkyl;

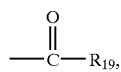

wherein $R_{19}$ is selected from the group consisting of aryl, heteroaryl, —S$R_{20}$, —O$R_{21}$, and —$R_{22}$CO$_2$$R_{23}$,
wherein $R_{20}$ is selected from the group consisting of alkyl, aryl and aminoalkyl,
$R_{21}$ is aryl,
$R_{22}$ is alkylene, and
$R_{23}$ is alkyl;

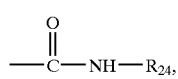

wherein $R_{24}$ is selected from the group consisting of hydrogen, unsubstituted alkyl, and aralkyl;

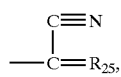

wherein $R_{25}$ is heterocyclylidenyl;

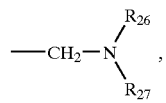

wherein $R_{26}$ and $R_{27}$ are independently alkyl;

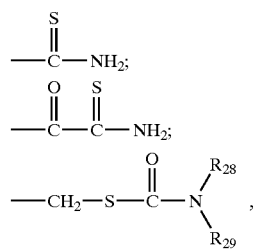

wherein $R_{28}$ and $R_{29}$ are independently alkyl;

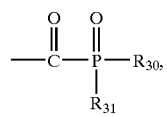

wherein $R_{30}$ and $R_{31}$ are independently alkoxy;

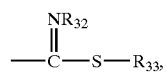

wherein $R_{32}$ is selected from the group consisting of hydrogen and alkyl, and
$R_{33}$ is alkyl;

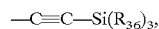

wherein $R_{36}$ is alkyl;

wherein $R_{37}$ and $R_{38}$ are independently alkyl;

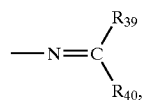

wherein $R_{39}$ is selected from the group consisting of hydrogen, alkoxy, and alkylthio, and
$R_{40}$ is selected from the group consisting of haloalkyl, cycloalkyl, heterocyclylalkoxy, and alkylthio;

—N=$R_{41}$, wherein $R_{41}$ is heterocyclylidenyl;

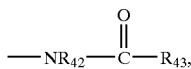

wherein $R_{42}$ is selected from the group consisting of hydrogen and alkyl, and $R_{43}$ is selected from the group consisting of cycloalkyl, chlorinated alkyl and substituted heteroaryl;

wherein $R_{44}$ is heteroaryl;

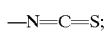

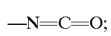

wherein $R_{45}$ is selected from the group consisting of hydrogen, alkyl, haloalkyl, heterocyclyl, aralkyl, heteroaralkyl, alkylthioalkyl, aminocarbonylalkyl, —$SR_{46}$, and —$CH_2R_{47}$, wherein $R_{46}$ is selected from the group consisting of aryl and heteroaryl, and $R_{47}$ is selected from the group consisting of aryl and heteroaryl; and

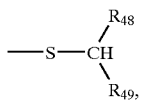

wherein $R_{48}$ is selected from the group consisting of hydrogen and alkyl, and $R_{49}$ is selected from the group consisting of alkoxy and haloalkyl;

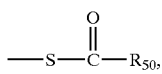

wherein $R_{50}$ is selected from the group consisting of alkyl, alkoxy, aryl and heteroaryl;

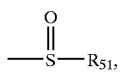

wherein $R_{51}$ is selected from the group consisting of haloalkyl and alkyl; and

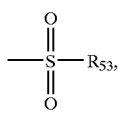

wherein $R_{53}$ is aryl;

or a pharmaceutically acceptable salt or tautomer thereof, provided that when $R_5$ is heterocyclylalkyl or heterocyclylalkenyl, then the heterocyclyl radical is other than a δ-lactone and the alkyl or alkenyl radical is other than —$CH_2CH_2$— or —CH═CH—.

Preferably, the immediately preceding embodiment involves the administration of a substituted pyridine of Formula IA as described above wherein:

when $R_2$ is difluoromethyl, $R_3$ is —$CO_2CH_3$, $R_5$ is

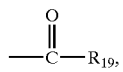

$R_6$ is trifluoromethyl and $R_{19}$ is the heteroaryl 1-pyrazolyl, then $R_4$ is other than isopropylamino; and when $R_2$ is difluoromethyl, $R_3$ is —$CO_2CH_3$, $R_5$ is the unsubstituted heterocyclyl 2-(4,5-dihydro-oxazolyl), and $R_6$ is trifluoromethyl, then $R_4$ is other than cyclopropylmethyl; and when $R_2$ and $R_6$ are selected from the group consisting of difluoromethyl and trifluoromethyl, $R_3$ is selected from the group consisting of —$CO_2H$ and —$CO_2C_2H_5$, and $R_5$ is cyano, then $R_4$ is other than ethyl or —CH═C(CH$_3$)$_2$; and when $R_2$ is methyl, $R_3$ is —$CO_2C_2H_5$, $R_5$ is

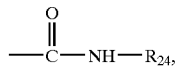

$R_6$ is methyl, and $R_{24}$ is —C(O)NHCH$_2$-(4-chlorophenyl), then $R_4$ is other than hydrogen; and when $R_2$ is methyl, $R_3$ and $R_5$ are —$CO_2C_2H_5$, $R_4$ is i-propoxy, then $R_6$ is other than methyl; and when $R_2$ is difluoromethyl, $R_4$ is —CH═C(CH$_3$)$_2$, $R_5$ is —$CO_2CH_3$, and $R_6$ is trifluoromethyl, then $R_3$ is other than —$CO_2H$; and when $R_2$ is methyl, $R_4$ is hydrogen, $R_5$ is —$CO_2C_2H_5$, and $R_6$ is methyl, then $R_3$ is other than —$CO_2C_2H_5$;

when $R_2$ is difluoromethyl, $R_4$ is hydrogen, $R_5$ is —$CO_2C_2H_5$, and $R_6$ is trifluoromethyl, then $R_3$ is other than —$CO_2C_2H_5$;

when $R_2$ is difluoromethyl, $R_4$ is —$CH_2SCH_3$, $R_5$ is —$CO_2C_2H_5$, and $R_6$ is trifluoromethyl, then $R_3$ is other than —$CO_2H$;

when $R_2$ is trifluoromethyl, $R_3$ is —$CO_2CH_3$, $R_4$ is isobutyl, $R_5$ is —$CO_2CH_3$, then $R_6$ is other than methyl;

when $R_2$ is difluoromethyl, $R_4$ is selected from the group consisting of isopropyl and isobutyl, $R_5$ is —$CO_2R_{14}$, $R_6$ is trifluoromethyl, and $R_{14}$ is alkyl, then $R_3$ is other than amido;

when $R_2$ is selected from the group consisting of hydroxy and trifluoromethyl, $R_4$ and $R_5$ are hydrogen, and $R_6$ is selected from the group consisting of methyl and trifluoromethyl, then $R_3$ is other than —$CO_2H$;

when $R_2$ is selected from the group consisting of methyl, difluoromethyl and trifluoromethyl, $R_3$ is —$CO_2CH_3$, $R_5$ is hydrogen, and $R_6$ is selected from the group consisting of methyl and trifluoromethyl, then $R_4$ is other than alkyl or arylcarbonyloxy;

when $R_2$ is trifluoromethyl, $R_3$ is —$CO_2C_2H_5$, $R_4$ is hydroxy, and $R_5$ is hydrogen, then $R_6$ is other than hydrogen; and when $R_2$ is trifluoromethyl, $R_3$ is selected from the group consisting of —$CO_2H$ and —$CO_2C_2H_5$, $R_5$ is methyl, and $R_6$ is selected from the group consisting of hydrogen and trifluoromethyl, then $R_4$ is other than hydroxy.

Among the objects of the present method are the inhibition of CTEP in vivo; the treatment or prevention of coronary artery disease; the treatment or prevention of atherosclerosis; the alteration of the LDL/HDL ratio or profile in plasma; and the elevation of HDL levels in plasma.

The present invention is additionally directed to the novel substituted pyridines of Formula IIA:

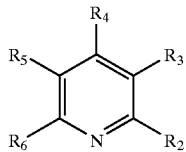

(IIA)

wherein:

$R_2$ and $R_6$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of $R_2$ and $R_6$ is fluorinated alkyl, chlorofluorinated alkyl or alkoxyalkyl;

$R_3$ is selected from the group consisting of arylcarbonyl, heteroarylcarbonyl, hydroxymethyl, arylalkoxyalkyl, trialkylsilyloxyalkyl,

—CHO,

—CO$_2$R$_7$, wherein $R_7$ is selected from the group consisting of hydrogen and alkyl; and

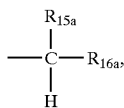

wherein $R_{15a}$ is selected from the group consisting of hydroxy, halogen, alkylthio and alkoxy, and $R_{16a}$ is selected from the group consisting of alkyl, haloalkyl, alkenyl, aryl and heteroaryl;

$R_4$ is selected from the group consisting of hydrogen, hydroxy, alkyl, aryl, cycloalkyl, cycloalkylalkyl, heteroarylalkyl, alkoxy, thio, trialkylsilyl, alkylamino, and —OC(O)N(R$_8$)$_2$, wherein $R_8$ is aryl;

$R_5$ is selected from the group consisting of hydrogen, alkyl, haloalkyl, alkenyl, haloalkenyl, alkynyl, haloalkynyl, aralkyl, alkoxy, aryloxy, cycloalkylthioalkyl, arylthioalkyl, heteroarylthioalkyl, alkoxyalkenyl, arylcarbonyloxyalkyl, pyrrolyl, substituted pyrrolidinyl, hydroxymethyl, arylalkoxyalkyl, and trialkylsilyloxyalkyl,

—CO$_2$R$_{14}$, wherein $R_{14}$ is alkyl;

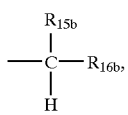

wherein $R_{15b}$ is selected from the group consisting of hydroxy, halogen, alkoxy, and alkylthio, aroyloxy, and alkylsulfonyloxy, and $R_{16b}$ is selected from the group consisting of alkyl, alkenyl, aryl, and heteroaryl;

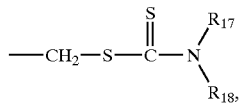

wherein $R_{17}$ and $R_{18}$ are independently alkyl;

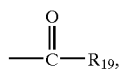

wherein $R_{19}$ is aryl, heteroaryl, —SR$_{20}$, and —OR$_{21}$, wherein $R_{20}$ is selected from the group consisting of aryl, heteroaryl and aminoalkyl, and $R_{21}$ is selected from the group consisting of aryl and heteroaryl;

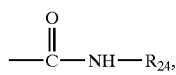

wherein $R_{24}$ is aralkyl;

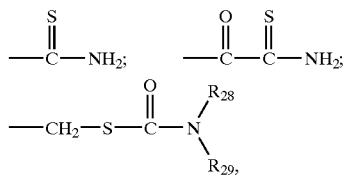

wherein $R_{28}$ and $R_{29}$ are independently alkyl;

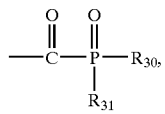

wherein $R_{30}$ and $R_{31}$ are independently alkoxy;

—C≡C—Si(R$_{36}$)$_3$, wherein $R_{36}$ is alkyl;

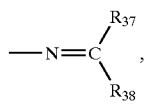

wherein $R_{37}$ is selected from the group consisting of hydrogen, alkoxy, and alkylthio, and $R_{38}$ is selected from the group consisting of haloalkyl, cycloalkyl, heterocyclylalkoxy, and alkylthio;

provided that when $R_{37}$ is hydrogen, then $R_{38}$ is selected from the group consisting of haloalkyl, cycloalkyl, and heterocyclylalkoxy;

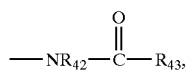

wherein $R_{42}$ is selected from the group consisting of hydrogen and alkyl, and $R_{43}$ is substituted heteroaryl;

wherein $R_{44}$ is selected from the group consisting of aryl and heteroaryl;

—$SR_{45}$, wherein $R_{45}$ is selected from the group consisting of haloalkyl, heterocyclyl, alkylthioalkyl, aminocarbonylalkyl, —$SR_{46}$, and —$CH_2R_{47}$, wherein $R_{46}$ is selected from the group consisting of aryl and heteroaryl, and $R_{47}$ is selected from the group consisting of methylenedioxyphenyl, pyridyl, quinolinyl, tetrahydronaphthyl and benzodioxanyl;

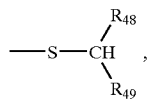

wherein $R_{48}$ is selected from the group consisting of hydrogen and alkyl, and $R_{49}$ is selected from the group consisting of alkoxy and haloalkyl;

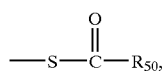

wherein $R_{50}$ is selected from the group consisting of alkyl, alkoxy, and heteroaryl; and

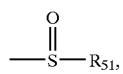

wherein $R_{51}$ is haloalkyl;

or a pharmaceutically acceptable salt or tautomer thereof, provided that:

when $R_2$ is selected from the group consisting of difluoromethyl and trifluoromethyl, $R_3$ is selected from the group consisting of —$CO_2H$, —$CO_2CH_3$ and —$CO_2C_2H_5$, $R_5$ is hydrogen, and $R_6$ is selected from the group consisting of hydrogen and trifluoromethyl, then $R_4$ is other than hydrogen, hydroxy or iso-butyl; provided further that when $R_2$, $R_3$ and $R_5$ are as defined above, and $R_4$ is selected from the group consisting of alkylamino and alkoxy, then $R_6$ is hydrogen;

when $R_2$ is selected from the group consisting of fluorinated methyl and chlorofluorinated methyl, $R_3$ is selected from the group consisting of hydroxymethyl and $CO_2R_7$, $R_5$ is selected from the group consisting of hydroxymethyl and $CO_2R_{14}$, $R_6$ is selected from the group consisting of alkyl, fluorinated methyl and chlorofluorinated methyl, and $R_7$ and $R_{14}$ are independently alkyl, then $R_4$ is other than alkyl, cycloalkyl, cycloalkylalkyl, hydroxy, alkoxy, aryl, alkylamino and heteroarylalkyl;

when $R_2$ is selected from the group consisting of difluoromethyl and trifluoromethyl, $R_3$ is —$CO_2C_2H_5$, $R_4$ is hydrogen, and $R_5$ is —$CO_2C_2H_5$, then $R_6$ is other than trifluoromethyl;

when $R_2$ is trifluoromethyl, $R_3$ is $CO_2R_7$, $R_5$ is methyl, and $R_6$ is selected from the group consisting of fluorinated methyl, fluorinated ethyl and chlorofluorinated methyl, then $R_4$ is other than alkoxy, alkylamino and hydroxy;

when $R_4$ is selected from the group consisting of alkyl, cycloalkyl and cycloalkylalkyl, $R_3$ is —$CO_2R_7$, and $R_7$ is alkyl, then $R_5$ is other than arylcarbonyl, heteroarylcarbonyl or

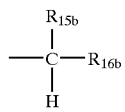

wherein $R_{16b}$ is alkyl when $R_{15b}$ is selected from the group consisting of hydroxy, halogen, alkylthio and alkoxy, or wherein $R_{16b}$ is aryl or heteroaryl when $R_{15b}$ is hydroxy;

when $R_4$ is selected from the group consisting of alkyl, cycloalkyl and cycloalkylalkyl, $R_5$ is —$CO_2R_{14}$, and $R_{14}$ is alkyl, then $R_3$ is other than arylcarbonyl, heteroarylcarbonyl or

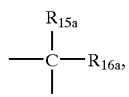

wherein $R_{16a}$ is alkyl when $R_{15a}$ is selected from the group consisting of hydroxy, halogen, alkylthio and alkoxy, or wherein $R_{16a}$ is aryl or heteroaryl when $R_{15a}$ is hydroxy; and when $R_2$ and $R_6$ are independently selected from fluorinated methyl and chlorofluorinated methyl, $R_3$ is $CO_2R_7$, $R_5$ is hydroxy, alkoxy or aryloxy, then $R_4$ is other than hydrogen, hydroxy, alkyl or alkoxy; and when $R_4$ is aryl and one of $R_2$ and $R_6$ is trifluoromethyl, then the other of $R_2$ and $R_6$ is difluoromethyl.

DETAILED DESCRIPTION OF THE PREFERRED EMBODIMENTS

Novel Methods

The present invention comprises a method for the treatment or prophylaxis of CTEP-mediated disorders (such as coronary artery disease) in a subject, comprising administering to the subject having such a disorder a therapeutically-effective amount of a compound of Formula I:

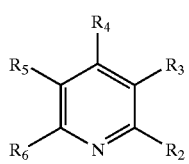

(I)

wherein:

$R_2$ and $R_6$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of $R_2$ and $R_6$ is fluorinated alkyl, chlorofluorinated alkyl or alkoxyalkyl;

$R_3$ is selected from the group consisting of hydroxy, amido, arylcarbonyl, heteroarylcarbonyl, hydroxymethyl,

—CHO,

—$CO_2R_7$, wherein $R_7$ is selected from the group consisting of hydrogen, alkyl and cyanoalkyl; and $$\begin{array}{c} R_{15a} \\ | \\ -C-R_{16a}, \\ | \\ H \end{array}$$

wherein $R_{15a}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy and heterocyclyloxy, and $R_{16a}$ is selected from the group consisting of alkyl, haloalkyl, alkenyl, haloalkenyl, alkynyl, haloalkynyl, aryl, heteroaryl, and heterocyclyl, arylalkoxy, trialkylsilyloxy;

$R_4$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkoxy, alkenoxy, alkynoxy, aryloxy, heteroaryloxy, heterocyclyloxy, alkanoyloxy, alkenoyloxy, alkynoyloxy, aryloyloxy, heteroaroyloxy, heterocyclyloyloxy, alkoxycarbonyl, alkenoxycarbonyl, alkynoxycarbonyl, aryloxycarbonyl, heteroaryloxycarbonyl, heterocyclyloxycarbonyl, thio, alkylthio, alkenylthio, alkynylthio, arylthio, heteroarylthio, heterocyclylthio, cycloalkylthio, cycloalkenylthio, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkylamino, alkenylamino, alkynylamino, arylamino, heteroarylamino, heterocyclylamino, aryldialkylamino, diarylamino, diheteroarylamino, alkylarylamino, alkylheteroarylamino, arylheteroarylamino, trialkylsilyl, trialkenylsilyl, triarylsilyl, —$OC(O)N(R_{8a}R_{8b})$, wherein $R_{8a}$ and $R_{8b}$ are independently selected from the group consisting of alkyl, alkenyl, alkynyl, aryl, heteroaryl and heterocyclyl, —$SO_2R_9$, wherein $R_9$ is selected from the group consisting of hydroxy, alkyl, alkenyl, alkynyl, aryl, heteroaryl and heterocyclyl, —$OP(O)(OR_{10a})(OR_{10b})$, wherein $R_{10a}$ and $R_{10b}$ are independently selected from the group consisting of hydrogen, hydroxy, alkyl, alkenyl, alkynyl, aryl, heteroaryl and heterocyclyl, and —$OP(S)(OR_{11a})(OR_{11b})$, wherein $R_{11a}$ and $R_{11b}$ are independently selected from the group consisting of alkyl, alkenyl, alkynyl, aryl, heteroaryl and heterocyclyl;

$R_5$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, alkoxy, alkenoxy, alkynoxy, aryloxy, heteroaryloxy, heterocyclyloxy, alkylcarbonyloxyalkyl, alkenylcarbonyloxyalkyl, alkynylcarbonyloxyalkyl, arylcarbonyloxyalkyl, heteroarylcarbonyloxyalkyl, heterocyclylcarbonyloxyalkyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, cycloalkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkoxyalkyl, alkenoxyalkyl, alkynoxyalkyl, aryloxyalkyl, heteroaryloxyalkyl, heterocyclyloxyalkyl, alkoxyalkenyl, alkenoxyalkenyl, alkynoxyalkenyl, aryloxyalkenyl, heteroaryloxyalkenyl, heterocyclyloxyalkenyl, cyano, hydroxymethyl,

—$CO_2R_{14}$, wherein $R_{14}$ is selected from the group consisting of alkyl, alkenyl, alkynyl, aryl, heteroaryl and heterocyclyl;

$$\begin{array}{c} R_{15b} \\ | \\ -C-R_{16b}, \\ | \\ H \end{array}$$

wherein $R_{15b}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy, heterocyclyloxy, aroyloxy, and alkylsulfonyloxy, and $R_{16b}$ is selected from the group consisting of alkyl, alkenyl, alkynyl, aryl, heteroaryl, heterocyclyl, arylalkoxy, and trialkylsilyloxy;

$$-CH_2-S-\overset{\overset{\displaystyle S}{\|}}{C}-N\overset{R_{17}}{\underset{R_{18}}{\diagup}},$$

wherein $R_{17}$ and $R_{18}$ are independently selected from the group consisting of alkyl, cycloalkyl, alkenyl, alkynyl, aryl, heteroaryl and heterocyclyl;

$$-\overset{\overset{\displaystyle O}{\|}}{C}-R_{19},$$

wherein $R_{19}$ is selected from the group consisting of alkyl, cycloalkyl, alkenyl, alkynyl, aryl, heteroaryl, heterocyclyl, —$SR_{20}$, —$OR_{21}$, and —$R_{22}CO_2R_{23}$, wherein $R_{20}$ is selected from the group consisting of alkyl, alkenyl, alkynyl, aryl, heteroaryl, heterocyclyl, aminoalkyl, aminoalkenyl, aminoalkynyl, aminoaryl, aminoheteroaryl, aminoheterocyclyl, alkylheteroarylamino, arylheteroarylamino, $R_{21}$ is selected from the group consisting of alkyl, alkenyl, alkynyl, aryl, heteroaryl, and heterocyclyl, $R_{22}$ is selected from the group consisting of alkylene or arylene, and $R_{23}$ is selected from the group consisting of alkyl, alkenyl, alkynyl, aryl, heteroaryl, and heterocyclyl;

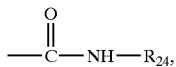

wherein $R_{24}$ is selected from the group consisting of hydrogen, alkyl, cycloalkyl, alkenyl, alkynyl, aryl, heteroaryl, heterocyclyl, aralkyl, aralkenyl, and aralkynyl;

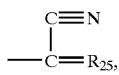

wherein $R_{25}$ is heterocyclylidenyl;

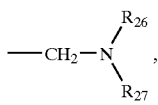

wherein $R_{26}$ and $R_{27}$ are independently selected from the group consisting of hydrogen, alkyl, cycloalkyl, alkenyl, alkynyl, aryl, heteroaryl, and heterocyclyl;

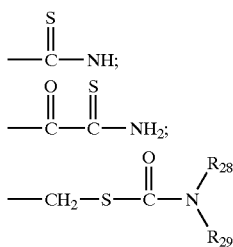

wherein $R_{28}$ and $R_{29}$ are independently selected from the group consisting of hydrogen, alkyl, cycloalkyl, alkenyl, alkynyl, aryl, heteroaryl, and heterocyclyl;

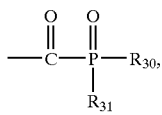

wherein $R_{30}$ and $R_{31}$ are independently alkoxy, alkenoxy, alkynoxy, aryloxy, heteroaryloxy, and heterocyclyloxy; and

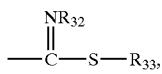

wherein $R_{32}$ and $R_{33}$ are independently selected from the group consisting of hydrogen, alkyl, cycloalkyl, alkenyl, alkynyl, aryl, heteroaryl, and heterocyclyl;

wherein $R_{36}$ is selected from the group consisting of alkyl, alkenyl, aryl, heteroaryl and heterocyclyl;

wherein $R_{37}$ and $R_{38}$ are independently selected from the group consisting of hydrogen, alkyl, cycloalkyl, alkenyl, alkynyl, aryl, heteroaryl, and heterocyclyl;

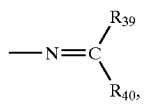

wherein $R_{39}$ is selected from the group consisting of hydrogen, alkoxy, alkenoxy, alkynoxy, aryloxy, heteroaryloxy, heterocyclyloxy, alkylthio, alkenylthio, alkynylthio, arylthio, heteroarylthio and heterocyclylthio, and $R_{40}$ is selected from the group consisting of haloalkyl, haloalkenyl, haloalkynyl, haloaryl, haloheteroaryl, haloheterocyclyl, cycloalkyl, cycloalkenyl, heterocyclylalkoxy, heterocyclylalkenoxy, heterocyclylalkynoxy, alkylthio, alkenylthio, alkynylthio, arylthio, heteroarylthio and heterocyclylthio;

wherein $R_{41}$ is heterocyclylidenyl;

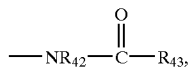

wherein $R_{42}$ is selected from the group consisting of hydrogen, alkyl, alkenyl, alkynyl, aryl, heteroaryl, and heterocyclyl, and $R_{43}$ is selected from the group consisting of hydrogen, alkyl, alkenyl, alkynyl, aryl, heteroaryl, heterocyclyl, cycloalkyl, cycloalkenyl, haloalkyl, haloalkenyl, haloalkynyl, haloaryl, haloheteroaryl, and haloheterocyclyl;

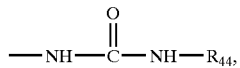

wherein $R_{44}$ is selected from the group consisting of hydrogen, alkyl, cycloalkyl, alkenyl, alkynyl, aryl, heteroaryl and heterocyclyl;

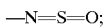

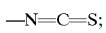

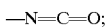

wherein $R_{45}$ is selected from the group consisting of hydrogen, alkyl, alkenyl, alkynyl, aryl, heteroaryl, heterocyclyl, haloalkyl, haloalkenyl, haloalkynyl, haloaryl, haloheteroaryl, haloheterocyclyl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, aminocarbonylalkyl, aminocarbonylalkenyl, aminocarbonylalkynyl, aminocarbonylaryl, aminocarbonylheteroaryl, and aminocarbonylheterocyclyl, —SR$_{46}$, and —CH$_2$R$_{47}$, wherein R$_{46}$ is selected from the group consisting of alkyl, alkenyl, alkynyl, aryl, heteroaryl and heterocyclyl, and R$_{47}$ is selected from the group consisting of hydrogen, alkyl, alkenyl, alkynyl, aryl, heteroaryl and heterocyclyl; and

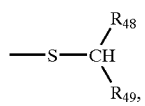

wherein R$_{48}$ is selected from the group consisting of hydrogen, alkyl, cycloalkyl, alkenyl, alkynyl, aryl, heteroaryl and heterocyclyl, and R$_{49}$ is selected from the group consisting of alkoxy, alkenoxy, alkynoxy, aryloxy, heteroaryloxy, heterocyclyloxy, haloalkyl, haloalkenyl, haloalkynyl, haloaryl, haloheteroaryl and haloheterocyclyl;

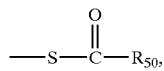

wherein R$_{50}$ is selected from the group consisting of hydrogen, alkyl, cycloalkyl, alkenyl, alkynyl, aryl, heteroaryl, heterocyclyl, alkoxy, alkenoxy, alkynoxy, aryloxy, heteroaryloxy and heterocyclyloxy;

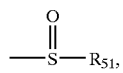

wherein R$_{51}$ is selected from the group consisting of alkyl, alkenyl, alkynyl, aryl, heteroaryl, heterocyclyl, haloalkyl, haloalkenyl, haloalkynyl, haloaryl, haloheteroaryl and haloheterocyclyl; and

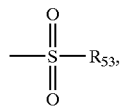

wherein R$_{53}$ is selected from the group consisting of alkyl, alkenyl, alkynyl, aryl, heteroaryl and heterocyclyl;
or a pharmaceutically acceptable salt or tautomer thereof, provided that when R$_5$ is selected from the group consisting of heterocyclylalkyl and heterocyclylalkenyl, then the heterocyclyl radical of the corresponding heterocyclylalkyl or heterocyclylalkenyl is other than a δ-lactone; and provided that when R$_4$ is aryl, heteroaryl or heterocyclyl, and one of R$_2$ and R$_6$ is trifluoromethyl, then the other of R$_2$ and R$_6$ is difluoromethyl.

In another embodiment, the method comprises the administration of a therapeutically effective amount of a substituted pyridine of Formula IA:

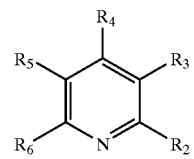

(IA)

wherein:

R$_2$ and R$_6$ are independently selected from the group consisting of hydrogen, hydroxy, alkyl, fluorinated alkyl, chlorofluorinated alkyl, cycloalkyl, heterocyclyl, aryl, heteroaryl, alkoxy, alkoxyalkyl, and alkoxycarbonyl; provided that at least one of R$_2$ and R$_6$ is fluorinated alkyl, chlorofluorinated alkyl or alkoxyalkyl;

R$_3$ is selected from the group consisting of hydroxy, amido, arylcarbonyl, heteroarylcarbonyl, hydroxymethyl,

wherein R$_7$ is selected from the group consisting of hydrogen, alkyl (preferably methyl or ethyl) and cyanoalkyl; and

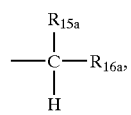

wherein R$_{15a}$ is selected from the group consisting of hydroxy, halogen, alkylthio and alkoxy, and R$_{16a}$ is selected from the group consisting of alkyl, aryl and heteroaryl;

R$_4$ is selected from the group consisting of hydrogen, hydroxy, halogen, alkyl, cycloalkyl, haloalkyl, alkenyl, aryl, heteroaryl, cycloalkylalkyl, heteroarylalkyl, aralkenyl, alkoxy, aralkoxy, alkoxycarbonyl, arylcarbonyloxy, thio, alkylthio, arylthio, cycloalkylthio, heterocyclylthio, alkylthioalkyl, alkylamino, trialkylsilyl, —OC(O)N(R$_8$)$_2$, wherein R$_8$ is aryl, —SO$_2$R$_9$, wherein R$_9$ is aryl, —OP(O) (OR$_{10}$)$_2$, wherein R$_{10}$ is alkyl, and —OP(S) (OR$_{11}$)$_2$, wherein R$_{11}$ is alkyl;

R$_5$ is selected from the group consisting of hydrogen, hydroxy, halogen, alkyl, haloalkyl, alkynyl, heterocyclyl, heteroaryl, alkoxy, aryloxy, arylcarbonyloxyalkyl, heterocyclylalkyl, alkylthioalkyl, arylthioalkyl, heteroarylthioalkyl, alkoxyalkenyl, cyano, hydroxymethyl,

—CO$_2$R$_{14}$, wherein $R_{14}$ is alkyl;

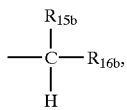

wherein $R_{15b}$ is selected from the group consisting of hydroxy, hydrogen, alkylthio and alkoxy, and $R_{16b}$ is selected from the group consisting of alkyl, aryl and heteroaryl;

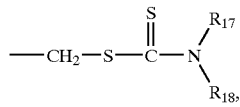

wherein $R_{17}$ and $R_{18}$ are independently alkyl;

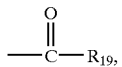

wherein $R_{19}$ is selected from the group consisting of aryl, heteroaryl, —$SR_{20}$, —$OR_{21}$, and —$R_{22}CO_2R_{23}$, wherein $R_{20}$ is selected from the group consisting of alkyl, aryl and aminoalkyl, $R_{21}$ is aryl, $R_{22}$ is alkylene, and $R_{23}$ is alkyl;

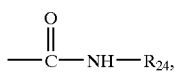

wherein $R_{24}$ is selected from the group consisting of hydrogen, unsubstituted alkyl, and aralkyl;

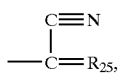

wherein $R_{25}$ is heterocyclylidenyl;

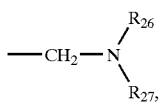

wherein $R_{26}$ and $R_{27}$ are independently alkyl;

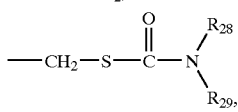

wherein $R_{28}$ and $R_{29}$ are independently alkyl;

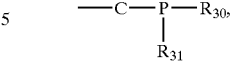

wherein $R_{30}$ and $R_{31}$ are independently alkoxy;

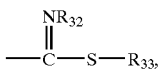

wherein $R_{32}$ is selected from the group consisting of hydrogen and alkyl, and $R_{33}$ is alkyl;

wherein $R_{36}$ is alkyl;

wherein $R_{37}$ and $R_{38}$ are independently alkyl;

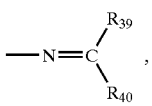

wherein $R_{39}$ is selected from the group consisting of hydrogen, alkoxy, and alkylthio, and $R_{40}$ is selected from the group consisting of haloalkyl, cycloalkyl, heterocyclylalkoxy, and alkylthio;

—N=$R_{41}$, wherein $R_{41}$ is heterocyclylidenyl;

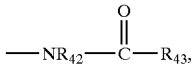

wherein $R_{42}$ is selected from the group consisting of hydrogen and alkyl, and $R_{43}$ is selected from the group consisting of cycloalkyl, chlorinated alkyl and substituted heteroaryl;

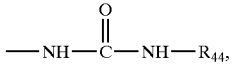

wherein $R_{44}$ is heteroaryl;

—N=S=O;

—N=C=S;

—N=C=O;

—$N_3$;

—$SR_{45}$, wherein $R_{45}$ is selected from the group consisting of hydrogen, alkyl, haloalkyl, heterocyclyl, aralkyl, heteroaralkyl, alkylthioalkyl, aminocarbonylalkyl, —$SR_{46}$, and —$CH_2R_{47}$, wherein $R_{46}$ is selected from the group consisting of aryl and heteroaryl, and $R_{47}$ is selected from the group consisting of aryl and heteroaryl; and

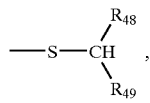

wherein $R_{48}$ is selected from the group consisting of hydrogen and alkyl, and $R_{49}$ is selected from the group consisting of alkoxy and haloalkyl;

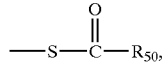

wherein $R_{50}$ is selected from the group consisting of alkyl, alkoxy, aryl and heteroaryl;

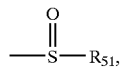

wherein $R_{51}$ is selected from the group consisting of haloalkyl and alkyl; and

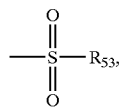

wherein $R_{53}$ is aryl;

or a pharmaceutically acceptable salt or tautomer thereof, provided that when $R_5$ is selected from the group consisting of heterocyclylalkyl and heterocyclylalkenyl, then the heterocyclyl radical is other than a δ-lactone and the alkyl or alkenyl radical is other than —$CH_2CH_2$— or —CH=CH—.

Preferably, the immediately preceding embodiment involves the administration of a substituted pyridine of Formula IA as described above wherein:

when $R_2$ is difluoromethyl, $R_3$ is —$CO_2CH_3$, $R_5$ is

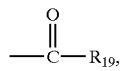

$R_6$ is trifluoromethyl, and $R_{19}$ is the heteroaryl 1-pyrazolyl, then $R_4$ is selected from the group consisting of hydrogen, hydroxy, halogen, alkoxy, cycloalkyl, haloalkyl, alkenyl, aryl, heteroaryl, cycloalkylalkyl, heteroarylalkyl, aralkenyl, alkoxy, aralkoxy, alkoxycarbonyl, arylcarbonyloxy, thio, alkylthio, arylthio, cycloalkylthio, heterocyclylthio, alkylthioalkyl, trialkylsilyl, —$OC(O)N(R_8)_2$, wherein $R_8$ is aryl, —$SO_2R_9$, wherein $R_9$ is aryl, —$OP(O)(OR_{10})_2$, wherein $R_{10}$ is alkyl, and —$OP(S)(OR_{11})_2$, wherein $R_{11}$ is alkyl; and when $R_2$ is difluoromethyl, $R_3$ is —$CO_2CH_3$, $R_5$ is the heterocyclyl 2-(4,5-dihydro-oxazolyl), and $R_6$ is trifluoromethyl, then $R_4$ is selected from the group consisting of hydrogen, hydroxy, halogen, alkyl, cycloalkyl, haloalkyl, alkenyl, aryl, heteroaryl, heteroarylalkyl, aralkenyl, alkoxy, aralkoxy, alkoxycarbonyl, arylcarbonyloxy, thio, alkylthio, arylthio, cycloalkylthio, heterocyclylthio, alkylthioalkyl, alkylamino, trialkylsilyl, —$OC(O)N(R_8)_2$, wherein $R_8$ is aryl, —$SO_2R_9$, wherein $R_9$ is aryl, —$OP(O)(OR_{10})_2$, wherein $R_{10}$ is alkyl, and —$OP(S)(OR_{11})_2$, wherein $R_{11}$ is alkyl; and when $R_2$ and $R_6$ are independently fluorinated methyl, $R_3$ is —$CO_2R_7$, $R_5$ is cyano, and $R_7$ is selected from the group consisting of hydrogen and alkyl, then $R_4$ is selected from the group consisting of hydrogen, hydroxy, halogen, cycloalkyl, haloalkyl, heteroaryl, cycloalkylalkyl, heteroarylalkyl, aralkenyl, alkoxy, aralkoxy, alkoxycarbonyl, arylcarbonyloxy, thio, alkylthio, arylthio, cycloalkylthio, heterocyclylthio, alkylthioalkyl, alkylamino, trialkylsilyl, —$OC(O)N(R_8)_2$, wherein $R_8$ is aryl, —$SO_2R_9$, wherein $R_9$ is aryl, —$OP(O)(OR_{10})_2$, wherein $R_{10}$ is alkyl, and —$OP(S)(OR_{11})_2$, wherein $R_{11}$ is alkyl; and when $R_2$ is methyl, $R_3$ is —$CO_2C_2H_5$, $R_5$ is

$R_6$ is methyl, and $R_{24}$ is aralkyl, then $R_4$ is selected from the group consisting of hydroxy, halogen, alkyl, cycloalkyl, haloalkyl, alkenyl, aryl, heteroaryl, cycloalkylalkyl, heteroarylalkyl, aralkenyl, alkoxy, aralkoxy, alkoxycarbonyl, arylcarbonyloxy, thio, alkylthio, arylthio, cycloalkylthio, heterocyclylthio, alkylthioalkyl, alkylamino, trialkylsilyl, —$OC(O)N(R_8)_2$, wherein $R_8$ is aryl, —$SO_2R_9$, wherein $R_9$ is aryl, —$OP(O)(OR_{10})_2$, wherein $R_{10}$ is alkyl, and —$OP(S)(OR_{11})_2$, wherein $R_{11}$ is alkyl, and when $R_2$ is methyl, $R_3$ and $R_5$ are —$CO_2C_2H_5$, and $R_4$ is alkoxy, then $R_6$ is selected from the group consisting of hydrogen, hydroxy, alkyl comprising at least two carbon atoms, fluorinated alkyl, chlorofluorinated alkyl, alkoxy, alkoxyalkyl, and alkoxycarbonyl;

when $R_2$ is difluoromethyl, $R_3$ is —$CO_2R_7$, $R_4$ is alkenyl, $R_5$ is $CO_2CH_3$, and $R_6$ is trifluoromethyl, then $R_7$ is selected from the group consisting of alkyl and cyanoalkyl, when $R_2$ is methyl, $R_4$ is hydrogen, $R_5$ is $CO_2C_2H_5$, and $R_6$ is methyl, then $R_3$ is selected from the group consisting of hydroxy, amido and —$CO_2R_7$, wherein $R_7$ is selected from the group consisting of hydrogen, methyl, alkyl comprising at least three carbon atoms, and cyanoalkyl, when $R_2$ is difluoromethyl, $R_4$ is hydrogen, $R_5$ is $CO_2C_2H_5$, and $R_6$ is trifluoromethyl, then $R_3$ is selected from the group consisting of hydroxy, amido and —$CO_2R_7$, wherein $R_7$ is selected from the group consisting of hydrogen, methyl, alkyl comprising at least three carbon atoms, and cyanoalkyl, when $R_2$ is difluoromethyl, $R_4$ is alkylthioalkyl, $R_5$ is —$CO_2C_2H_5$, and $R_6$ is trifluoromethyl, then $R_3$ is selected from the group consisting of hydroxy, amido and —$CO_2R_7$, wherein $R_7$ is selected from the group consisting of alkyl and cyanoalkyl, when $R_2$ is trifluoromethyl, $R_3$ is —$CO_2CH_3$, $R_4$ is alkyl, $R_5$ is —$CO_2CH_3$, then $R_6$ is selected from the group consisting of hydrogen, hydroxy, alkyl comprising at least two carbon atoms, fluorinated alkyl, chlorofluorinated alkyl, alkoxy, alkoxyalkyl, and alkoxycarbonyl, when $R_2$ is difluoromethyl, $R_4$ is alkyl, $R_5$ is —$CO_2R_{14}$, $R_6$ is trifluoromethyl, and $R_{14}$ is alkyl, then $R_3$ is selected from the group consisting of hydroxy and —$CO_2R_7$, wherein $R_7$ is selected from the group consisting of hydrogen, alkyl and cyanoalkyl, when $R_2$ is selected from the group consisting of hydroxy and trifluoromethyl, $R_4$ and $R_5$ are hydrogen, and $R_6$ is selected from the group consisting of methyl and trifluoromethyl, then $R_3$ is selected from the group consisting of hydroxy, amido and —$CO_2R_7$, wherein $R_7$ is selected from the group consisting of alkyl and cyanoalkyl, when $R_2$ is selected from the group consisting of methyl, difluoromethyl and trifluoromethyl, $R_3$ is —$CO_2CH_3$, $R_5$ is hydrogen, and $R_6$ is selected from the group consisting of methyl and trifluoromethyl, then $R_4$ is selected from the group consisting of hydrogen, hydroxy, halogen, cycloalkyl, alkenyl, aryl, heteroaryl, cycloalkylalkyl, heteroarylalkyl, aralkenyl, alkoxy, aralkoxy, alkoxycarbonyl, thio, alkylthio, arylthio, cycloalkylthio, heterocyclylthio, alkylthioalkyl, alkylamino, trialkylsilyl, —OC(O) N($R_8$)$_2$, wherein $R_8$ is aryl, —SO$_2R_9$, wherein $R_9$ is aryl, —OP(O) (OR$_{10}$)$_2$, wherein $R_{10}$ is alkyl; and —OP(S) (OR$_{11}$)$_2$, wherein $R_{11}$ is alkyl; and when $R_2$ is trifluoromethyl, $R_3$ is —$CO_2C_2H_5$, $R_4$ is hydroxy, and $R_5$ is hydrogen, then $R_6$ is selected from the group consisting of hydroxy, alkyl, fluorinated alkyl, alkoxy, alkoxyalkyl and alkoxycarbonyl; and when $R_2$ is trifluoromethyl, $R_3$ is selected from the group consisting of —$CO_2H$ and —$CO_2C_2H_5$, $R_5$ is methyl, and $R_6$ is selected from the group consisting of hydrogen and trifluoromethyl, then $R_4$ is selected from the group consisting of hydrogen, halogen, alkyl, cycloalkyl, haloalkyl, alkenyl, aryl, heteroaryl, cycloalkylalkyl, heteroarylalkyl, aralkenyl, alkoxy, aralkoxy, alkoxycarbonyl, arylcarbonyloxy, thio, alkylthio, arylthio, cycloalkylthio, heterocyclylthio, alkylthioalkyl, alkylamino, trialkylsilyl, —OC(O)N($R_8$)$_2$, wherein $R_8$ is aryl, —SO$_2R_9$, wherein $R_9$ is aryl, —OP(O) (OR$_{10}$)$_2$, wherein $R_{10}$ is alkyl, and —OP(S) (OR$_{11}$)$_2$, wherein $R_{11}$ is alkyl.

In another embodiment, the method comprises the administration of a therapeutically effective amount of a substituted pyridine of Formula IA as defined in one of the embodiments discussed above wherein:

$R_2$ is selected from the group consisting of methyl and fluorinated methyl; and $R_3$ is —$CO_2R_7$, wherein $R_7$ is selected from the group consisting of hydrogen, methyl and ethyl.

Pharmaceutically Acceptable Salts

Also included in the family of compounds of Formulae I, IA and IB used in the method of the present invention (as well as in the family of novel compounds of Formula IIA and IIB discussed below) are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compound by reacting, for example, the appropriate acid or base with the compound.

Treatment of CETP-Mediated Disorders

The methods of this invention additionally can be used, for example: (i) to inhibit cholesteryl ester transfer protein (CETP) activity, (ii) to decrease the concentrations of low density lipoprotein (LDL) and/or raise the level of high density lipoprotein (HDL), or otherwise alter lipoprotein profiles, resulting in a therapeutically beneficial plasma lipid profile; (iii) for the primary and secondary treatment of coronary artery disease, myocardial infarction and agina; (iv) for the treatment of dyslipidemia (hypoalphalipoproteinaemia), hyperlipoproteinaemia (chylomicronemia and hyperapobetalipoproteinaemia), peripheral vascular disease, hypercholesterolemia, atherosclerosis, and other CETP-mediated disorders; (v) for the prophylactic treatment of subjects who are at risk of developing CETP-mediated disorders; and (vi) to lower the risk of atherosclerosis. The methods would be also useful in prevention of cerebral vascular accident (CVA) or stroke.

Besides being useful for human treatment, these methods are also useful for veterinary treatment of companion animals, exotic animals and farm animals, including mammals, rodents, and the like. More preferred animals include horses, dogs, and cats.

Without being limited to a specific theory, applicant hypothesizes that the CETP molecule contains one or more specific hydrophobic binding sites that can accommodate the substituted pyridines of the present invention. Binding of the substituted pyridine to these sites is sufficient to inhibit CETP. This binding is generally rapid and reversible.

It is additionally hypothesized that the CETP molecule contains a cysteine at or near these hydrophobic binding sites. Inhibition potency can be enhanced by selecting a substituted pyridine which is capable of undergoing a disulfide exchange with this cysteine. This disulfide exchange is time-dependent and irreversible. While inhibition potency may be enhanced as a result of this disulfide exchange, substituted pyridines which are effective inhibitors and which do not undergo the disulfide exchange may be more desirable given the generally irreversible nature of the disulfide exchange reaction.

It is further hypothesized that such disulfide-modified CETP molecules can aggregate, perhaps as a result of conformational changes induced by interaction with the substituted pyridine.

Additional Embodiments of Novel Methods

In another embodiment, the method comprises the administration of a therapeutically effective amount of a compound of Formula IA wherein:

$R_2$ is fluorinated alkyl;
$R_3$ is —$CO_2R_7$, wherein $R_7$ is selected from the group consisting of hydrogen and alkyl;
$R_4$ is selected from the group consisting of alkyl, cycloalkyl and cycloalkylalkyl;
$R_5$ is selected from the group consisting of:
heteroaryl (preferably 1-pyrrolyl);

wherein $R_{37}$ and $R_{38}$ are independently alkyl;

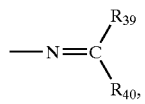

wherein $R_{39}$ is selected from the group consisting of hydrogen, alkoxy, and alkylthio, and
$R_{40}$ is selected from the group consisting of haloalkyl, cycloalkyl, heterocyclylalkoxy, and alkylthio;

—N=$R_{41}$, wherein $R_{41}$ is heterocyclylidenyl;

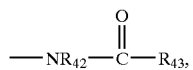

wherein $R_{42}$ is selected from the group consisting of hydrogen and alkyl, and
$R_{43}$ is selected from the group consisting of cycloalkyl, chlorinated alkyl, and heteroaryl;

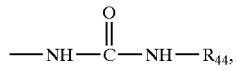

wherein $R_{44}$ is heteroaryl (preferably substituted pyridyl);

—N=S=O;

—N=C=S;

—N=C=O; and

—$N_3$; and $R_6$ is fluorinated alkyl;
or a pharmaceutically acceptable salt or tautomer thereof.

In still another embodiment, the method comprises the administration of a therapeutically effective amount of a compound of Formula IA wherein:

$R_2$ is fluorinated alkyl;
$R_3$ is —$CO_2R_7$, wherein $R_7$ is selected from the group consisting of hydrogen and alkyl;
$R_4$ is selected from the group consisting of alkyl, haloalkyl, cycloalkyl, alkoxy and alkylthio;
$R_5$ is selected from the group consisting of:

—$SR_{45}$, wherein $R_{45}$ is selected from the group consisting of hydrogen, alkyl, haloalkyl, heterocyclyl, aralkyl, heteroaralkyl, aminocarbonylalkyl, alkylthioalkyl, —$SR_{46}$, and —$CH_2R_{47}$,
wherein $R_{46}$ is selected from the group consisting of aryl (preferably substituted aryl) and heteroaryl (preferably substituted pyridyl), and
$R_{47}$ is selected from the group consisting of aryl and heteroaryl ($R_41$ is preferably substituted aryl); and

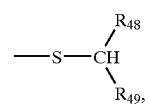

wherein $R_{48}$ is selected from the group consisting of hydrogen and alkyl, and
$R_{49}$ is selected from the group consisting of alkoxy and haloalkyl;

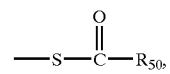

wherein $R_{50}$ is selected from the group consisting of alkyl, alkoxy, aryl and heteroaryl (preferably substituted heteroaryl);

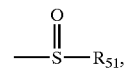

wherein $R_{51}$ is selected from the group consisting of alkyl and haloalkyl; and

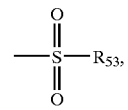

wherein $R_{53}$ is aryl; and
$R_6$ is fluorinated alkyl;
or a pharmaceutically acceptable salt or tautomer thereof.

In still another embodiment, the method comprises the administration of a therapeutically effective amount of a compound of Formula IA wherein:

$R_2$ is selected from the group consisting of alkyl and fluorinated alkyl;

$R_3$ is —$CO_2R_7$, wherein $R_7$ is selected from the group consisting of hydrogen and alkyl;

$R_4$ is selected from the group consisting of hydroxy, alkoxy, aralkoxy, alkoxycarbonyl, alkylthio, arylthio, —OC(O)N($R_8$)$_2$, wherein $R_8$ is aryl, —SO$_2$R$_9$, wherein $R_9$ is aryl, —OP(O) (OR$_{10}$)$_2$, wherein $R_{10}$ is alkyl, and —OP(S) (OR$_{11}$)$_2$, wherein $R_{11}$ is alkyl;

$R_5$ is selected from the group consisting of hydrogen, hydroxy, halogen, alkoxy, and aryloxy; and $R_6$ is selected from the group consisting of hydrogen, fluorinated alkyl and alkoxycarbonyl;

or a pharmaceutically acceptable salt or tautomer thereof, provided that when $R_2$ is trifluoromethyl, $R_3$ is —$CO_2C_2H_5$, $R_4$ is hydroxy and $R_5$ is hydrogen, then $R_6$ is selected from the group consisting of fluorinated alkyl and alkoxycarbonyl.

In yet another preferred embodiment, the method comprises the administration of a therapeutically effective amount of a compound of Formula IA wherein:

$R_2$ is fluorinated alkyl;

$R_3$ is —$CO_2R_7$, wherein $R_7$ is selected from the group consisting of hydrogen, alkyl and cyanoalkyl;

$R_4$ is selected from the group consisting of alkyl, alkoxy, cycloalkyl, cycloalkylalkyl, arylcarbonyloxy, arylthio, and alkylamino;

$R_5$ is selected from the group consisting of alkyl, haloalkyl, alkynyl, heterocyclyl, heteroaryl, heterocyclylalkyl, arylcarbonyloxyalkyl, alkylthioalkyl, arylthioalkyl, heteroarylthioalkyl, alkoxyalkenyl, cyano,

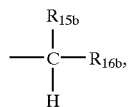

wherein $R_{15a}$ is selected from the group consisting of hydroxy, alkylthio and alkoxy, and $R_{16b}$ is selected from the group consisting of alkyl and heteroaryl;

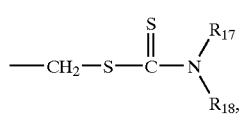

wherein $R_{17}$ and $R_{18}$ are each alkyl;

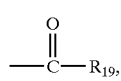

wherein $R_{19}$ is selected from the group consisting of heteroaryl (preferably a substituted pyridyl), —SR$_{20}$, —OR$_{21}$, and —R$_{22}$CO$_2$R$_{23}$, wherein $R_{20}$ is selected from the group consisting of alkyl, aryl (preferably substituted aryl) and aminoalkyl, $R_{21}$ is aryl (preferably substituted aryl), $R_{22}$ is alkylene, and $R_{23}$ is alkyl;

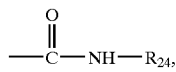

wherein $R_{24}$ is selected from the group consisting of hydrogen, unsubstituted alkyl, and aralkyl;

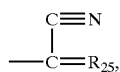

wherein $R_{25}$ is heterocyclylidenyl;

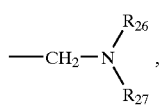

wherein $R_{26}$ and $R_{27}$ are independently alkyl;

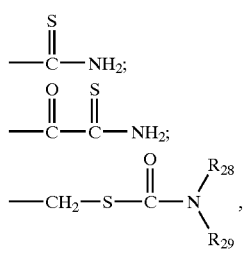

wherein $R_{28}$ and $R_{29}$ are independently alkyl;

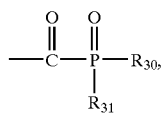

wherein $R_{30}$ and $R_{31}$ are each alkoxy;

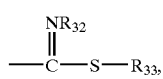

wherein $R_{32}$ is selected from the group consisting of hydrogen and alkyl, and $R_{33}$ is alkyl;

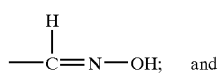 and

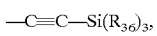

wherein $R_{36}$ is alkyl; and $R_6$ is selected from the group consisting of hydrogen, fluorinated alkyl and alkoxy, or a pharmaceutically acceptable salt or tautomer thereof, provided that:

when $R_2$ is difluoromethyl, $R_3$ is —$CO_2CH_3$, $R_5$ is

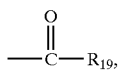

$R_6$ is trifluoromethyl, and $R_{19}$ is the heteroaryl 1-pyrazolyl, then $R_4$ is selected from the group consisting of alkyl, alkoxy, cycloalkyl, cycloalkylalkyl, arylcarbonyloxy, and arylthio; and when $R_2$ is difluoromethyl, $R_3$ is —$CO_2CH_3$, $R_5$ is the heterocyclyl 2-(4,5-dihydro-oxazolyl), and $R_6$ is trifluoromethyl, then $R_4$ is selected from the group consisting of alkyl, alkoxy, cycloalkyl, arylcarbonyloxy, arylthio, and alkylamino; and when $R_2$ and $R_6$ are independently fluorinated methyl, $R_3$ is —$CO_2R_7$, $R_5$ is cyano, and $R_7$ is selected from the group consisting of hydrogen and alkyl, then $R_4$ is selected from the group consisting of alkoxy, cycloalkyl, cycloalkylalkyl, arylcarbonyloxy, arylthio, and alkylamino.

In yet another embodiment, the method comprises the administration of a therapeutically effective amount of a compound of Formula IA wherein:

$R_2$ is selected from the group consisting of hydroxy, alkyl, fluorinated alkyl, and alkoxyalkyl;

$R_3$ is selected from the group consisting of hydroxy, amido, and —$CO_2R_7$, wherein $R_7$ is selected from the group consisting of hydrogen and alkyl;

$R_4$ is selected from the group consisting of hydrogen, hydroxy, halogen, alkyl, cycloalkyl, haloalkyl, alkenyl, aryl, heteroaryl, heteroarylalkyl, alkoxy, alkoxycarbonyl, aralkenyl, thio, alkylthio, cycloalkylthio, heterocyclylthio, alkylthioalkyl, and trialkylsilyl;

$R_5$ is $CO_2R_{14}$, wherein $R_{14}$ is alkyl;

$R_6$ is selected from the group consisting of hydrogen, hydroxy, alkyl, fluorinated alkyl, and alkoxyalkyl;

or a pharmaceutically acceptable salt or tautomer thereof, provided that:

when $R_2$ is methyl, $R_3$ is —$CO_2C_2H_5$, $R_4$ is alkoxy, and $R_5$ is —$CO_2C_2H_5$, then $R_6$ is selected from the group consisting of hydrogen, hydroxy, alkyl comprising at least two carbon atoms, fluorinated alkyl, and alkoxyalkyl;

when $R_2$ is difluoromethyl, $R_3$ is —$CO_2R_7$, $R_4$ is alkenyl, $R_5$ is $CO_2CH_3$, and $R_6$ is trifluoromethyl, then $R_7$ is alkyl;

when $R_2$ is methyl, $R_4$ is hydrogen, $R_5$ is $CO_2R_{14}$, $R_6$ is methyl, and $R_{14}$ is alkyl, then $R_3$ is selected from the group consisting of hydroxy, amido and —$CO_2R_7$, wherein $R_7$ is selected from the group consisting of hydrogen, methyl, alkyl comprising at least three carbon atoms and cyanoalkyl;

when $R_2$ is difluoromethyl, $R_4$ is hydrogen, $R_5$ is $CO_2R_{14}$, $R_6$ is trifluoromethyl, and $R_{14}$ is alkyl, then $R_3$ is selected from the group consisting of hydroxy, amido and —$CO_2R_7$, wherein $R_7$ is selected from the group consisting of hydrogen, methyl, alkyl comprising at least three carbon atoms and cyanoalkyl;

when $R_2$ is difluoromethyl, $R_4$ is alkylthioalkyl, $R_5$ is $CO_2C_2H_5$, and $R_6$ is methyl, then $R_3$ is selected from the group consisting of hydroxy, amido and —$CO_2R_7$, wherein $R_7$ is alkyl;

when $R_2$ is trifluoromethyl, $R_3$ is —$CO_2CH_3$, $R_4$ is alkyl, and $R_5$ is —$CO_2CH_3$, then $R_6$ is selected from the group consisting of hydrogen, hydroxy, alkyl comprising two or more carbon atoms, fluorinated alkyl, and alkoxyalkyl; and when $R_2$ is difluoromethyl, $R_4$ is alkyl, $R_5$ is yselected from the group consisting of —$CO_2CH_3$ and —$CO_2C_2H_5$, and $R_6$ is trifluoromethyl, then $R_3$ is selected from the group consisting of hydroxy and —$CO_2R_7$, wherein $R_7$ is selected from the group consisting of hydrogen and alkyl.

In yet another embodiment, the method comprises the administration of a therapeutically effective amount of a compound of Formula IA which is selected from the compounds disclosed in Tables 1–8 below. While a number of the compounds disclosed in Tables 1–7 below either were specifically known or generically disclosed in the art as herbicides, they were not known to possess the pharmacologic properties of the present invention. Among the compounds of Tables 1–7 used in the method which were not previously specifically known or generically disclosed in the art as herbicides are those compounds identified with an asterisk.

TABLE 1

(T-1)

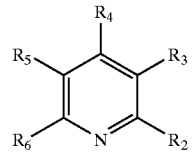

| Compound | $R_2$ | $R_3$ | $R_4$ | $R_5$ | $R_6$ | Procedure Reference | $IC_{50}(\mu m)$ |
|---|---|---|---|---|---|---|---|
| 1 | $CF_2H$ | $CO_2CH_3$ | i-Bu | N=S=O | $CF_3$ | U.S. Pat. No. 4,885,026 EXAMPLE 165 | 2 |
| 2* | $CF_2H$ | $CO_2CH_3$ | SH | $CO_2C_2H_5$ | $CF_3$ | EXAMPLE $2^A$ | 3 |
| 3* | $CF_2H$ | $CO_2CH_3$ | i-Bu | $CH_2S$-(4-t-butylphenyl) | $CF_3$ | EXAMPLE $3^A$ | 9 |
| 4* | $CF_2H$ | $CO_2CH_3$ | S-(4,5-dihydro-2-thiazolyl) | $CO_2C_2H_5$ | $CF_3$ | U.S. Pat. No. 4,698,093 EXAMPLE 169 | 6 |
| 5* | $CF_2H$ | $CO_2CH_3$ | i-Bu | $SC(O)C_{15}H_{31}$ | $CF_3$ | EXAMPLE $23^A$ | 8 |
| 6 | $CF_2H$ | $CO_2CH_3$ | i-Bu | $SCO_2CH_3$ | $CF_3$ | EXAMPLE $11^A$ | 8 |
| 7 | $CF_2H$ | $CO_2CH_3$ | i-Bu | SH | $CF_3$ | EXAMPLE $1^A$ | 8.75 |
| 8 | $CF_2H$ | $CO_2CH_3$ | i-Bu | (1,4-dithian-2- | $CF_3$ | U.S. Pat. No. 5,129,943 | 10 |

TABLE 1-continued (T-1)

Structure: pyridine with R2 (position 2), R3 (position 3), R4 (position 4), R5 (position 5), R6 (position 6), N in ring.

| Compound | $R_2$ | $R_3$ | $R_4$ | $R_5$ | $R_6$ | Procedure Reference | $IC_{50}(\mu m)$ |
|---|---|---|---|---|---|---|---|
| | | | | ylidene) amino | | EXAMPLE43 | |
| 9 | $CF_2H$ | $CO_2$-t-Bu | i-Bu | $CO_2$-t-Bu | $CF_3$ | EXAMPLE 9$^A$ | 20 |
| 10 | $CF_3$ | $CO_2C_2H_5$ | OC(0)[4-trifluoro methyl)-phenyl] | $CH_3$ | $CF_3$ | U.S. Pat. No. 4,655,816 EXAMPLE 61 | 25 |
| 11 | $CF_3$ | $CO_2C_2H_5$ | S-(4-i-propylphenyl) | $CH_3$ | $CF_3$ | EXAMPLE 4$^A$ | 25 |
| 12 | $CF_3$ | $CO_2CH_3$ | i-Bu | 4,5-dihydro-2-thiazolyl | $CF_3$ | U.S. Pat. No. 4,988,384 EXAMPLE 21 | 25 |
| 13 | $CF_2H$ | $CO_2CH_3$ | i-Bu | CH(OH)-2-furyl | $CF_3$ | U.S. Pat. No. 3,280,262 EXAMPLE H | 30 |
| 14 | $CF_2H$ | $CO_2CH_3$ | c-Bu | C(O)S-i-Pr | $CF_3$ | EXAMPLE 12$^A$ | 30 |
| 15 | $CF_2H$ | $CO_2C_2H_5$ | i-Bu | (tran-4,5-di-chloro-4,5-dihydro-3 isoxazolyl | $CF_3$ | U.S. Pat. No. 5,125,961 EX.37, CMPD. 24 | 30 |
| 16* | $CF_2H$ | $CO_2CH_3$ | i-Bu | N=C(OCH$_3$)CH$_2$Br | $CF_3$ | U.S. Pat. No. 4,885,026 SEE EX. 131 | 30 |
| 17 | $CF_3H$ | $CO_2CH_3$ | i-Bu | 4,5-dihydro-4-ethylidine-5-oxo-2-oxazolyl | $CF_3$ | U.S. Pat. No. 4,988,384 EXAMPLE 73 | 30 |
| 18 | $CF_2H$ | $CO_2CH_3$ | i-Bu | N=C=S | $CF_3$ | U.S. Pat. No. 5,129,943 EX. 41, STEP A | 35 |
| 19* | $CF_2H$ | $CO_2CH_3$ | i-Bu | C≡CSi(CH$_3$)$_3$ | $CF_3$ | EXAMPLE 21$^A$ | 35 |
| 20 | $CH_3$ | $CO_2C_2H_5$ | i-Bu | $CO_2C_2H_5$ | $CF_3$ | U.S. Pat. No. 4,692,184 EXAMPLE 246 | 37.5 |
| 21 | $CF_2H$ | $CO_2CH_3$ | $CH_2$c-Pr | CH(CH$_3$)SC$_2$H$_5$ | $CF_3$ | U.S. Pat. No. 5,169,432 EXAMPLE 56 | 40 |
| 22 | $CF_2H$ | $CO_2C_2H_5$ | S-c-C$_5$H$_9$ | $CO_2C_2H_5$ | $CF_3$ | U.S. Pat. No. 4,698,093 EXAMPLE 109 | 40 |
| 23 | $CF_3$ | $CO_2C_2H_5$ | S—Ph | H | $CF_3$ | U.S. Pat. No. 4,655,816 EXAMPLE 23 | 40 |
| 24 | $CF_3$ | $CO_2CH_3$ | OP(S)(OCH$_3$)$_2$ | H | $CF_3$ | U.S. Pat. No. 4,655,816 EXAMPLE 93 | 40 |
| 25* | $CF_3$ | $CO_2CH_3$ | OC(O)NPh$_2$ | H | $CF_3$ | EXAMPLE 13$^A$ | 40 |
| 26 | $CF_2H$ | $CO3CH_3$ | i-Bu | $CH_2SC_2H_3$ | $CF_3$ | U.S. Pat. No. 5,169,432 EXAMPLE 47 | 40 |
| 27* | $CF_2H$ | $CO_2CH_3$ | i-Bu | N=C(OCH$_3$)SCH$_3$ | $CF_3$ | EXAMPLE 34$^A$ | 40 |
| 28 | $CF_2H$ | $CO_2CH_3$ | i-Bu | C≡CH | $CF_3$ | U.S. Pat. No. 5,125,961 EXAMPLE 117 | 40 |
| 29* | $CF_2H$ | $CO_2CH_3$ | i-Bu | N=C(OCH$_3$)c-Pr | $CF_3$ | U.S. Pat. No. 4,885,026 SEE EX. 131 | 40 |
| 30* | $CF_2H$ | $CO_2CH_3$ | i-Bu | N=CHOCH$_2$-(2-oxiranyl) | $CF_3$ | EXAMPLE 36$^A$ | 40 |
| 31* | $CF_3$ | $CO_2C_2H_5$ | Si(CH$_3$)$_3$ | $CO_2C_2H_5$ | $CF_3$ | EXAMPLE 26$^A$ | 40 |
| 32 | $CF_2H$ | $CO_2CH_3$ | i-Bu | CH$_3$I | $CF_3$ | EXAMPLE 37$^A$ | 45 |
| 33* | $CF_2H$ | $CO_2CH_3$ | i-Bu | SCH$_2$SCH$_3$ | $CF_3$ | SEE EX. 23$^A$ | 45 |
| 34* | $CF_2H$ | $CO_2CH_3$ | i-Bu | CH(OCH$_3$)-(5-isothiazolyl) | $CF_3$ | EXAMPLE 38$^A$ | 45 |
| 35* | $CF_2H$ | $CO_2CH_3$ | CH$_3$-c-Pr | C(Br)=CHOCH$_3$ | $CF_3$ | EXAMPLE 52$^A$ | 45 |
| 36 | $CF_3$ | $CO_2C_2H_5$ | i-Bu | $CO_2C_2H_5$ | $CF_3$ | U.S. Pat. No. 4,692,184 EXAMPLE 7 | 45 |
| 37 | $CF_3$ | $CO_2C_2H_5$ | OCH$_2$Ph | H | $CF_3$ | U.S. Pat. No. 4,655,816 EXAMPLE 9 | 45 |
| 38 | $CF_2H$ | $CO_2C_2H_5$ | c-Hx | $CO_2C_2H_5$ | $CF_3$ | U.S. Pat. No. 4,692,184 EXAMPLE 21 | 50 |
| 39 | $CF_2H$ | $CO_2C_2H_5$ | S-t-Bu | $CO_2C_2H_5$ | $CF_3$ | U.S. Pat. No. 4,698,093 EXAMPLE 108 | 50 |
| 40* | $CF_2H$ | $CO_2CH_3$ | i-Bu | CH(OCH$_3$)-(2-thienyl) | $CF_3$ | SEE EX. 38$^A$ | 50 |
| 41* | $CF_2H$ | $CO_2CH_3$ | CH$_2$-c-Pr | CH$_2$OC(O)Ph | $CF_3$ | EXAMPLE 39$^A$ | 50 |
| 42* | $CF_2H$ | $CO_2CH_3$ | i-Bu | N=C(SCH$_3$)$_2$ | $CF_3$ | EXAMPLE 35$^A$ | 50 |
| 43* | $CF_2H$ | $CO_2CH_3$ | i-Bu | CH$_2$SC(S)N(CH$_3$)$_2$ | $CF_3$ | EXAMPLE 52$^A$ | 50 |

TABLE 1-continued

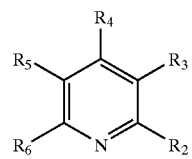

(T-1)

| Compound | R$_2$ | R$_3$ | R$_4$ | R$_5$ | R$_6$ | Procedure Reference | IC$_{50}$($\mu$m) |
|---|---|---|---|---|---|---|---|
| 44* | CF$_2$H | CO$_2$CH$_3$ | i-Bu | S(CH$_2$)$_2$Cl | CF$_3$ | SEE EX. 23$^A$ | 50 |
| 45 | CF$_2$H | CO$_2$CH$_3$ | i-Bu | COCH$_2$CO$_2$C$_2$H$_5$ | CF$_3$ | U.S. Pat. No. 5,260,262 SEE EX. 25 | 50 |
| 46 | CF$_2$H | CO$_2$CH$_3$ | i-Bu | [3-methyl-dihydro 2(3H)- thienylidene]amino | CF$_3$ | U.S. Pat. No. 5,129,943 EXAMPLE 64 | 50 |
| 47 | CF$_2$H | CO$_2$CH$_3$ | CH=C(CH$_3$)Ph | CO$_2$CH$_3$ | CF$_3$ | CMPD. 3f$^B$ | 50 |
| 48* | CF$_3$ | CO$_2$C$_2$H$_5$ | Et | NHC(O)NH-[2- (difluoromethyl)- 4-ethyl-5- carbethoxy-6- (trifluoromethyl)- 3-)pyridyl] | CF$_2$H | EXAMPLE 27$^A$ | 50 |
| 49 | CF$_2$H | CO$_2$CH$_3$ | CH$_2$-i-Bu | CO$_2$CH$_3$ | CF$_3$ | U.S. Pat. No. 4,692,184 SEE EX. 14 | 50 |
| 50 | CF$_2$H | CO$_2$CH$_3$ | i-Bu | 1,3-dithian-2-yl | CF$_3$ | U.S. Pat. No. 4,988,384 EXAMPLE 20 | 50 |
| 51 | CF$_3$ | CO$_2$C$_2$H$_5$ | SO$_2$Ph | H | CF$_3$ | U.S. Pat. No. 4,655,816 EXAMPLE 24 | 50 |
| 52 | CF$_3$ | CO$_2$CH$_3$ | OC$_2$H$_5$ | CO$_2$C$_2$H$_5$ | CF$_3$ | U.S. Pat. No. 4,698,093 EXAMPLE 17 | 50 |
| 53 | CF$_3$ | CO$_2$C$_2$H$_5$ | O-i-Pr | CH$_3$ | CF$_3$ | U.S. Pat. No. 4,655,816 EXAMPLE 37 | 50 |
| 54* | CF$_3$ | CO$_2$CH$_3$ | O-i-Pr | C(O)-[2-(trifluoro- methyl)-3-carbo- methoxy-4-i- propoxy-5-pyridyl) | H | EXAMPLE 28$^A$ | 50 |
| 55 | CF$_2$H | CO$_2$CH$_3$ | CH$_2$-c-Pr | C(CN)=[2-(1,3- dioxolanyl)) | CF$_3$ | U.S. Pat. No. 5,156,670 EXAMPLE 6 | 50 |
| 56 | CF$_2$H | CO$_2$CH$_3$ | i-Bu | CH$_2$N(CH$_3$)$_2$ | CF$_3$ | U.S. Pat. No. 5,169,432 EXAMPLE 50 | 50 |
| 57 | CF$_2$H | CO$_2$CH$_3$ | i-Bu | 5-methyl-3- isothiazolyl | CF$_3$ | U.S. Pat. No. 5,125,961 EXAMPLE 17 | 50 |
| 58 | CF$_2$H | CO$_2$CH$_3$ | i-Bu | C(SCH$_3$)=N-i-Pr | CF$_3$ | EXAMPLE 40$^A$ | 55 |
| 59 | CF$_2$H | CO$_2$CH$_3$ | i-Bu | 1,3-dioxan-2-yl | CF$_3$ | U.S. Pat. No. 4,988,384 EXAMPLE 109 | 55 |
| 60 | CF$_2$H | CO$_2$CH$_3$ | CH$_2$-c-Pr | CH$_2$SCH$_3$ | CF$_3$ | U.S. Pat. No. 5,169,432 EXAMPLE 47 | 60 |
| 61 | CF$_2$H | CO$_2$CH$_3$ | i-Bu | 1,3-dithiolan-2-yl | CF$_3$ | U.S. Pat. No. 4,988,384 EXAMPLE 19 | 60 |
| 62 | CF$_2$H | CO$_2$CH$_3$ | Pr | C(O)SC$_2$H$_5$ | CF$_3$ | U.S. Pat. No. 4,692,184 SEE EX. 140 | 60 |
| 63 | CF$_2$H | CO$_2$CH$_3$ | S-i-Pr | CO$_2$C$_2$H$_5$ | CF$_3$ | U.S. Pat. No. 4,698,093 EXAMPLE 32 | 60 |
| 64 | CF$_3$ | CO$_2$C$_2$H$_5$ | OC$_2$H$_5$ | CN | CF$_3$ | U.S. Pat. No. 4,698,093 EXAMPLE 25 | 60 |
| 65 | CF$_3$ | CO$_2$C$_2$H$_5$ | OC$_2$H$_5$ | CN | OC$_2$H$_5$ | U.S. Pat. No. 4,609,399 EXAMPLE 24 | 60 |
| 66 | CF$_2$H | CO$_2$CH$_3$ | c-Bu | SC$_2$H$_5$ | CF$_3$ | U.S. Pat. No. 4,789,395 EXAMPLE 76 | 60 |
| 67 | CF$_2$H | CO$_2$CH$_3$ | CH$_2$-[2- (methylthio) -4- pyrimidinyl] | CO$_2$CH$_3$ | CF$_3$ | EXAMPLE 20$^A$ | 60 |
| 68 | CF$_2$H | CO$_2$CH$_3$ | i-Pr | C(SCH$_3$)=NCH$_3$ | CF$_3$ | SEE EX. 40$^A$ | 65 |
| 69 | CF$_2$H | CO$_2$CH$_3$ | i-Bu | C(O)SCH$_3$ | CF$_3$ | U.S. Pat. No. 4,692,184 SEE EX. 140 | 65 |
| 70* | CF$_2$H | CO$_2$CH$_3$ | c-Bu | 1-pyrrolyl | CF$_3$ | EXAMPLE 29$^A$ | 65 |
| 71 | CF$_2$H | CO$_2$CH$_3$ | CH$_2$-c-Pr | N(CH$_3$)$_2$ | CF$_3$ | U.S. Pat. No. 5,037,469 EXAMPLE 7 | 70 |
| 72 | CF$_2$ | CO$_2$C$_2$H$_5$ | CH$_2$SCH$_3$ | CO$_2$C$_2$H$_5$ | CF$_3$ | U.S. Pat. No. 4,692,184 SEE EX. 6 | 70 |
| 73 | CF$_2$H | CO$_2$CH$_3$ | CH$_2$S-i-Pr | CO$_2$C$_2$H$_5$ | CF$_3$ | U.S. Pat. No. 4,692,184 SEE EX. 162 | 70 |
| 74 | CF$_2$H | CO$_2$CH$_3$ | CH=C(C$_2$H$_5$)$_2$ | CO$_2$CH$_3$ | CF$_3$ | SEE CMPD. 3d$^B$ | 70 |

TABLE 1-continued (T-1)

$$\text{pyridine with } R_2, R_3, R_4, R_5, R_6 \text{ substituents}$$

| Compound | $R_2$ | $R_3$ | $R_4$ | $R_5$ | $R_6$ | Procedure Reference | $IC_{50}(\mu m)$ |
|---|---|---|---|---|---|---|---|
| 75* | $CF_3$ | $CO_2CH_3$ | i-Bu | $C(O)NHCH_2$-(4-chlorophenyl) | $CF_2H$ | U.S. Pat. No. 4,692,184 SEE EX. 89 | 70 |
| 76 | $CF_3$ | $CO_2C_2H_5$ | Br | $CO_2C_2H_5$ | $CF_3$ | U.S. Pat. No. 4,698,093 EXAMPLE 104 | 70 |
| 77* | $CF_2H$ | $CO_2CH_3$ | i-Bu | $C(O)C(S)NH_2$ | $CF_3$ | EXAMPLE 30[A] | 70 |
| 78 | $CF_2H$ | $CO_2CH_3$ | Et | $N_3$ | $CF_3$ | U.S. Pat. No. 4,885,026 EXAMPLE 129 | 70 |
| 79* | $CF_2H$ | $CO_2CH_3$ | i-Bu | $CH_2SC(O)N(CH_3)_2$ | $CF_3$ | EXAMPLE 53[A] | 75 |
| 80 | $CF_2H$ | $CO_2CH_3$ | $C(CH_3)_2SCH_3$ | $CO_2C_2H_5$ | $CF_3$ | U.S. Pat. No. 4,692,184 EXAMPLE 170 | 80 |
| 81 | $CF_2H$ | $CO_2CH_3$ | i-Bu | $C(O)$-(2-chloro-5-thiazolyl) | $CF_3$ | U.S. Pat. No. 5,260,262 EXAMPLE 58 | 80 |
| 82 | $CF_3$ | $CO_2C_2H_5$ | 2-thienyl | $CO_2C_2H_5$ | $CF_3$ | U.S. Pat. No. 4,692,184 EXAMPLE 5 | 80 |
| 83 | $CF_2H$ | $CO_2CH_3$ | i-Bu | $CH_2Cl$ | $CF_3$ | U.S. Pat. No. 5,169,432 EXAMPLE 3 | 80 |
| 84 | $CF_3$ | $CO_2CH_3$ | $SCH_3$ | $SCH_3$ | $CF_3$ | U.S. Pat. No. 4,789,395 EXAMPLE 42 | 85 |
| 85* | $CF_3H$ | $CO_2CH_3$ | NH-i-Pr | $C(O)P(O)(OC_2H_5)_2$ | $CF_3$ | EXAMPLE 33[A] | 90 |
| 86 | $CF_3$ | $CO_2$-i-Pr | Et | $CO_2$-i-Pr | $CF_3$ | U.S. Pat. No. 4,692,184 EXAMPLE 60 | 90 |
| 87 | $CF_2H$ | $CO_2CH_3$ | $CH_2$-c-Pr | $CH_2SC_2H_5$ | $CF_3$ | U.S. Pat. No. 5,169,432 EXAMPLE 51 | 90 |
| 88 | $CF_3$ | $CO_2CH_3$ | i-Bu | 2-thiazolyl | $CF_3$ | U.S. Pat. No. 4,988,384 EXAMPLE 44 | 90 |
| 89 | $CF_2H$ | $CO_2CH_3$ | i-Bu | $CH(OH)$-(2-thienyl) | $CF_3$ | U.S. Pat. No. 5,260,262 SEE EX. H | 100 |
| 90 | $CF_3H$ | $CO_2CH_3$ | i-Bu | $C(=NH)SC_2H_5$ | $CF_3$ | SEE EX. 46[A] | 100 |
| 91 | $CF_3H$ | $CO_2CH_3$ | $CH_2I$ | $CO_2CH_3$ | $CF_3$ | U.S. Pat. No. 4,692,184 EXAMPLE 132 | 100 |
| 92* | $CH_2OCH_3$ | $CO_2CH_3$ | Pr | $CO_2CH_3$ | $CH_2OCH_3$ | EXAMPLE 32[A] | 100 |
| 93 | $CF_2H$ | $CO_2CH_3$ | i-Bu | 5-methoxy-2-oxazolyl | $CF_3$ | U.S. Pat. No. 4,988,384 EXAMPLE 33 | 100 |
| 94 | $CF_3$ | $CO_2C_2H_5$ | $SC_2H_5$ | H | $CF_3$ | U.S. Pat. No. 4,655,816 EXAMPLE 25 | 100 |
| 95 | $CF_2H$ | $CO_2CH_3$ | $CH(i-Pr)CO_2CH_3$ | $CO_2CH_3$ | $CF_3$ | CMPD. 7b[B] | 100 |
| 96 | $CH_3$ | OH | $CO_2C_2H_5$ | $CO_2C_2H_5$ | $CH_3$ | CHEM. PHARM. BUL.,14,18 (1966) | 100 |

[A]These examples correspond to the examples contained in the present application.
[B]J. Heterocyclic Chem., 26, 1771 (1989).

TABLE 2

(T-2)

| Compound | $R_2$ | $R_3$ | $R_4$ | $R_5$ | $R_6$ | Procedure Reference | % Transfer @ 100 $\mu m^c$ |
|---|---|---|---|---|---|---|---|
| 97 | $CF_2H$ | $CO_2CH_3$ | i-Bu | 3-methyl-2-oxazolidinyl | $CF_3$ | U.S. Pat. No. 4,988,384 EXAMPLE 14 | 59 |
| 98 | $CF_2H$ | $CO3CH_3$ | i-Pr | 4,5-dihydro-2-oxazolyl | $CF_3$ | U.S. Pat. No. 4,988,384 EXAMPLE 32 | 63 |
| 99 | $CF_2H$ | $CO_2CH_3$ | i-Bu | $C(O)NHBu$ | $CF_3$ | U.S. Pat. No. 4,692,184 SEE EX. 192 | 66 |
| 100 | $CF_2H$ | $CO_2CH_3$ | i-Bu | $NHC(O)CH_2Cl$ | $CF_3$ | U.S. Pat. No. 5,114,469 | 68 |

TABLE 2-continued (T-2)

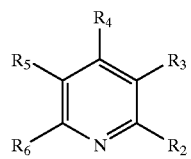

| Compound | R$_2$ | R$_3$ | R$_4$ | R$_5$ | R$_6$ | Procedure Reference | % Transfer @ 100 μm$^c$ |
|---|---|---|---|---|---|---|---|
| 101* | CF$_3$ | CO$_2$C$_2$H$_5$ | OH | CO$_2$-i-Pr | H | SEE EX. 4 | 71 |
| 102 | CH$_3$ | CO$_2$C$_2$H$_5$ | CO$_2$C$_2$H$_5$ | OH | H | EXAMPLE 41$^A$ BIOKHIMYA, 33, 350 (1968) | 72 |
| 103* | CF$_2$H | CO$_2$CH$_3$ | i-Bu | C(S)NH$_2$ | CF$_3$ | SEE EX. 49$^A$ | 73 |
| 104 | CF$_3$ | CO$_2$C$_2$H$_5$ | 3-pyridyl | CO$_2$C$_2$H$_5$ | CF$_3$ | U.S. Pat. No. 4,692,184 EXAMPLE 8 | 74 |
| 105 | CF$_2$H | CO$_2$CH$_3$ | i-Bu | CH(OH)-(4-methyl-2-thiazolyl) | CF$_3$ | U.S. Pat. No. 5,260,262 SEE EX. H | 74 |
| 106 | CH$_3$ | CO$_2$CH$_3$ | i-Bu | CO$_2$CH$_3$ | CH$_3$ | SEE FOOTNOTE E | 74 |
| 107* | CF$_2$H | CO$_2$CH$_3$ | CH$_2$-c-Pr | 1-hydroxy-5-methyl-3-pyrrolidinyl | CF$_3$ | EXAMPLE 42$^A$ | 75 |
| 108 | CF$_3$ | CO$_2$C$_2$H$_5$ | OC$_2$H$_5$ | CONH$_2$ | CF$_3$ | U.S. Pat. No. 4,698,093 EXAMPLE 20 | 76 |
| 109* | CF$_3$ | CO$_2$C$_2$H$_5$ | OH | OPh | H | EXAMPLE 43$^A$ | 76 |
| 110 | CF$_2$H | CO$_2$CH$_3$ | i-Bu | 2-oxazolyl | CF$_3$ | EXAMPLE 44$^A$ | 76 |
| 111* | CF$_2$H | CO$_2$CH$_3$ | i-Bu | S(O)(CH$_2$)$_2$Cl | CF$_3$ | EXAMPLE 45$^A$ | 78 |
| 112 | CF$_2$H | CO$_2$CH$_3$ | CH$_2$-c-Pr | C(=NH)SCH$_3$ | CF$_3$ | EXAMPLE 46$^A$ | 78 |
| 113 | CF$_3$ | CO$_2$C$_2$H$_5$ | 4-pyridyl | CO$_2$C$_2$H$_5$ | CF$_3$ | U.S. Pat. No. 4,692,184 EXAMPLE 9 | 80 |
| 114* | CF$_3$ | CO$_2$C$_2$H$_5$ | OH | OC$_2$H$_5$ | H | EXAMPLE 47$^A$ | 81 |
| 115 | CF$_2$H | CO$_2$CH$_3$ | c-Bu | S(O)C$_2$H$_5$ | CF$_3$ | U.S. Pat. No. 4,789,395 EXAMPLE 74 | 82 |
| 116 | CF$_3$ | CO$_2$CH$_3$ | OH | H | CO$_2$CH$_3$ | J. AGRIC. CHEM. 39, p. 1072 (1991) | 82 |
| 117* | CF$_2$H | CO$_2$CH$_3$ | i-Bu | NHC(O)-[2-chloro-4-(trifluoromethyl)-5-thiazolyl)] | CF$_3$ | EXAMPLE 48$^A$ | 83 |
| 118 | CF$_2$H | CO$_2$CH$_3$ | i-Bu | (1,3-oxathiolan-2-ylidene)amino | CF$_3$ | U.S. Pat. No. 5,129,943 EXAMPLE 41 | 83 |
| 119* | CF$_2$H | CO$_2$CH$_3$ | c-Bu | C(S)NH$_2$ | CF$_3$ | EXAMPLE 49$^A$ | 84 |
| 120 | CF$_2$H | CO$_2$CH$_3$ | Pr | CO$_2$CH$_3$ | CF$_3$ | U.S. Pat. No. 4,692,184 EXAMPLE 67 | 84 |
| 121* | CF$_3$ | CO$_2$C$_2$H$_5$ | O-i-Pr | H | H | EXAMPLE 41$^A$ | 88 |
| 122 | CH$_3$ | CO$_2$CH$_3$ | Pr | CO$_2$CH$_3$ | CH$_3$ | ANN, 246, p.32 (1888) | 88 |
| 123 | CF$_2$H | CO$_2$CH$_3$ | NH-i-Pr | C(=NCH$_3$)SCH$_3$ | CF$_3$ | U.S. Pat. No. 4,698,093 EXAMPLE 225 | 88 |
| 124 | CF$_2$H | CO$_2$CH$_3$ | CH$_2$-c-Pr | 5-oxazolyl | CF$_3$ | U.S. Pat. No. 4,988,284 SEE EX. 92 | 89 |
| 125* | CF$_3$ | CO$_2$C$_2$H$_5$ | OH | CO$_2$C$_2$H$_5$ | H | SEE EX. 41$^A$ | 89 |
| 126 | CF$_3$ | CO$_2$H | S-(4-i-propylphenyl) | CH$_3$ | CF$_3$ | EXAMPLE 50$^A$ | 90 |
| 127* | CF$_3$ | CO$_2$CH$_3$ | O-i-Pr | H | H | SEE EX. 41$^A$ | 90 |
| 128 | OH | CO$_2$C$_2$H$_5$ | H | CO$_2$C$_2$H$_5$ | OH | SEE FOOTNOTE F | 92 |
| 129 | CF$_3$ | CO$_2$CH$_3$ | OP(O)(OC$_2$H$_5$)$_2$ | H | CF$_3$ | U.S. Pat. No. 4,655,816 EXAMPLE 18 | 92 |
| 130 | CH$_3$ | CO$_2$C$_2$H$_5$ | CO$_2$C$_2$H$_5$ | OH | H HCl salt | BIOKHIMYA, 33, 350 (1968) | 94 |
| 131 | CF$_2$H | CO$_2$CH$_3$ | i-Bu | CH(OH)-(3,5-dimethyl-4-isoxazolyl) | CF$_3$ | U.S. Pat. No. 5,260,262 SEE EX. H | 93 |
| 132 | CH$_3$ | CO$_2$CH$_3$ | H | CO$_2$CH$_3$ | CH$_3$ | ANN, 241, p.1 (1882) | 94 |
| 133 | CF$_2$H | CO$_2$CH$_3$ | i-Bu | CH(OH)-(2-thiazolyl) | CF$_3$ | U.S. Pat. No. 5,260,262 SEE EX. H | 95 |
| 134* | CF$_2$H | CO$_2$CH$_3$ | i-Bu | C(O)S(CH$_2$)$_2$NH$_2$ | CF$_3$ | EXAMPLE 51$^B$ | 96 |
| 135 | CF$_3$ | CO$_2$C$_2$H$_5$ | OCH$_3$ | Br | CF$_3$ | U.S. Pat. No. 4,885,026 EXAMPLE 140 | 97 |
| 136* | CF$_3$ | CO$_2$C$_2$H$_5$ | H | CO$_2$C$_2$H$_5$ | CF$_3$ | U.S. Pat. No. 4,692,184 SEE EX. 1 | 97 |

TABLE 2-continued (T-2)

| Compound | $R_2$ | $R_3$ | $R_4$ | $R_5$ | $R_6$ | Procedure Reference | % Transfer @ 100 μm[c] |
|---|---|---|---|---|---|---|---|
| 137 | $CF_2H$ | $CONH_2$ | Et | $CO_2C_2H_5$ | $CF_3$ | U.S. Pat. No. 4,692,184 EXAMPLE 88 | 98 |
| 138 | $CF_3$ | $CO_2CH_3$ | O-i-Pr | $S(O)_2Ph$ | $CF_3$ | U.S. Pat. No. 4,789,395 EXAMPLE 47 | 98 |
| 139 | $CF_2H$ | $CO_2CH_2CN$ | i-Bu | 3,4-dihydro-2 thiazolyl | $CF_3$ | U.S. Pat. No. 4,988,384 EXAMPLE 88 | 98 |
| 140 | $CF_2H$ | $CO_2CH_3$ | i-Bu | CH=NOH | $CF_3$ | U.S. Pat. No. 5,125,961 EXAMPLE C | 99 |
| 141 | $CF_2H$ | $CO_2CH_3$ | i-Bu | 4,5-dihydro-1H-2-imidazoly- | $CF_3$ | U.S. Pat. No. 4,988,384 EXAMPLE 12 | 99 |
| 142 | $CF_2H$ | $CO_2CH_3$ | i-Bu | $N(CH_3)C(O)$-c-Pr | $CF_3$ | U.S. Pat. No. 5,037,469 EXAMPLE J1 | 99.5 |
| 143 | $CF_3$ | $CO_2CH_3$ | OH | H | $CF_3$ | U.S. Pat. No. 4,655,816 EXAMPLE 4 | 99.7 |
| 144 | $CF_2H$ | $CO_2CH_3$ | i-Bu | $CONH_2$ | $CF_3$ | RES. DTSCL., 295, 867(1988) | 94 |
| 145* | $CF_2H$ | $CO_2CH_3$ | i-Bu | $SCH_2C(O)NH_2$ | $CF_3$ | EXAMPLE 23[A] | 64 |
| 146* | $CF_2H$ | $CO_2CH_3$ | i-Bu | $SCH(CH_3)OC_2H_5$ | $CF_3$ | EXAMPLE 23[A] | 67[D] |
| 147* | $CF_2H$ | $CO_2CH_3$ | i-Bu | $SCH(CH_3)OCH_3$ | $CF_3$ | EXAMPLE 23[A] | 15[D] |
| 148* | $CF_2H$ | $CO_2CH_3$ | i-Bu | $S(CH_2)_2F$ | $CF_3$ | EXAMPLE 2[A] | 32[D] |
| 149* | $CF_2H$ | $CO_2CH_3$ | i-Bu | $SC(O)CH_3$ | $CF_3$ | SEE EX. 23[A] | 31[D] |
| 150* | $CF_2H$ | $CO_2CH_3$ | i-Bu | S-(tetrahydro-2-furyl) | $CF_3$ | EXAMPLE 31[A] | 95[D] |

[A]These examples correspond to the examples contained in the present application.
[B]J. Heterocyclic Chem., 26, 1771 (1989).
[C]All compounds in Table 2 exhibited an $IC_{50}$ greater than or equal to 100 μm when tested.
[D]% transfer at 10 μm.
[E]Compound 106 is prepared according to a procedure similar to that disclosed in Ann., 246, p. 32 except using isovaleraldehyde as the reagent.
[F]Compound 128 is prepared according to a procedure similar to that disclosed in Collect. Czech. Chem. Commun., 34, p. 427–441 (1969) except using ethyl cyanoacetate as the reagent instead of methyl cyanoacetate.

TABLE 3

| Compound | X | $Y_1$ | $Y_2$ | $Y_3$ | $Y_4$ | $Y_5$ | mp (° C.) | $IC_{50}$ (μm) |
|---|---|---|---|---|---|---|---|---|
| 151* | S | H | t-Bu | H | t-Bu | H | 102.5–108.5 | 60 |
| 152* | S | Me | H | Me | H | H | 98.5–102.5 | 60 |
| 153* | S | OMe | H | H | H | H | 100–102 | 100 |
| 154* | S | H | OMe | H | H | H | 87–88.5 | 100 |
| 155* | S | t-Bu | H | t-Hu | H | H | 115.5–120.5 | 50 |
| 156* | S | H | H | t-Bu | H | H | 60.5–62.5 | 100 |
| 157* | S | i-Pr | H | H | H | H | — | 60 |
| 158* | S | H | Me | H | Me | H | 96–99 | 100 |
| 159* | S | H | H | SMe | H | H | 112–114 | 80 |
| 160* | S | $CH_2$-(4-fluorophenyl) | H | i-Pr | H | H | 86.5–91 | 60 |
| 161* | S | $CH_2$-(4-fluorophenyl) | H | F | H | H | 105–107 | 70 |
| 162* | S | H | H | Cl | H | H | 94–96.5 | 50 |
| 163* | S | Cl | H | H | Cl | H | 112.5–113.5 | 65 |
| 164* | S | Cl | H | H | H | Cl | 109.5–112.5 | 50 |
| 165* | O | H | OMe | H | H | H | 74–75 | >100[A] |
| 166* | O | $NO_2$ | H | H | H | H | 102.5–105.5 | >100[B] |
| 167* | O | H | t-Bu | H | t-Bu | H | 100–103.5 | 60 |

TABLE 3-continued

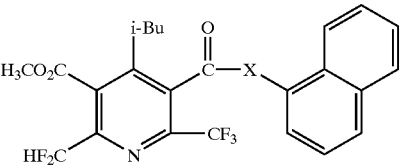

| Compound | X | $Y_1$ | $Y_2$ | $Y_3$ | $Y_4$ | $Y_5$ | mp (°C.) | $IC_{50}$ (μm) |
|---|---|---|---|---|---|---|---|---|
| 168* | O | t-Bu | H | t-Bu | H | H | — | 60 |
| 165* | O | H | H | t-Bu | H | H | — | 70 |
| 170* | O | CH$_2$-(4-fluorophenyl) | H | i-Pr | H | H | 102–104 | 40 |
| 171* | O | CH$_2$-(4-fluorophenyl) | OMe | OHe | OHe | H | 131.5–133.5 | 70 |
| 172* | O | OMe | H | H | H | H | 73–74.5 | >100$^C$ |
| 173* | O | H | H | Cl | H | H | 81.5–82.5 | 45 |
| 174* | O | H | Me | H | Me | H | 90.5–94 | 60 |
| 175* | O | iPr | H | H | H | H | — | >100$^D$ |
| 176* | O | Me | H | NO$_2$ | H | Me | 96–97 | 100 |
| 177* | O | Me | H | Me | H | H | 95–99 | 70 |

$^A$89% CE transferred @ 100 μm.
$^B$84% CE transferred @ 100 μm.
$^C$71% CE transferred @ 100 μm.
$^D$58% CE transferred @ 100 μm.

TABLE 4

| | COMPOUND | Mp (°C.) | $IC_{50}$ (μm) |
|---|---|---|---|
| 178* | 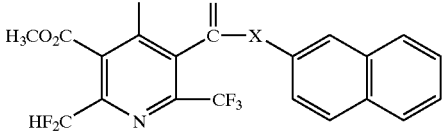 | mp 125–127.5 | $IC_{50}$ = 70 μm |
| 179* | 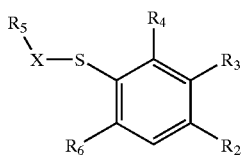 | mp 110–115 | $IC_{50}$ = 60 μm |

TABLE 5

(T-5)

R$_5$X—S—[phenyl with R$_4$, R$_3$, R$_2$, R$_6$]

| Compound | R$_2$ | R$_3$ | R$_4$ | R$_5$ | R$_6$ | X | $IC_{50}$ |
|---|---|---|---|---|---|---|---|
| 180* | CF$_2$H | CO$_2$CH$_3$ | i-Bu | 4-t-butylphenyl | CF$_3$ | S | 0.45 |
| 181* | CF$_2$H | CO$_2$CH$_3$ | i-Bu | 2-(difluoromethyl)-3-carbomethoxy-4-i-butyl-6-(trifluoromethyl)-5-pyridyl | CF$_3$ | S | 1.5 |
| 182* | CF$_2$H | CO$_2$CH$_3$ | i-Bu | 2-(difluoromethyl)-3-carbomethoxy-4-i-butyl-6-(trifluoromethyl)-5-pyridyl | CF$_3$ | CH$_2$ | 19 |

TABLE 5-continued

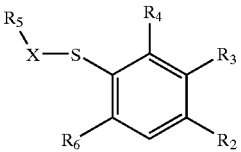

(T-5)

| Compound | $R_2$ | $R_3$ | $R_4$ | $R_5$ | $R_6$ | X | $IC_{50}$ |
|---|---|---|---|---|---|---|---|
| 183* | $CF_2H$ | $CO_2CH_3$ | i-Bu | 2-(difluoromethyl)-3-carbomethoxy-4-i-butyl-6-(trifluoromethyl)-5-pyridyl | $CF_3$ | C(O) | 50 |

TABLE 6

(T-6)

| Compound | R | $IC_{50}$ ($\mu$m) |
|---|---|---|
| 184* | 3-bromophenyl | 30 |
| 185* | 4-chlorophenyl | 10 |
| 186* | 2,3,5,6-tetrafluorophenyl | 50 |
| 187* | 3,5-di-t-butylphenyl | 40 |
| 188* | 2-(1-methyl imidazolyl) | >100[A] |
| 189* | 5-(1-methyltetrazolyl) | >100[A] |
| 190* | 2-(5-nitrobenzoimidazolyl) | 25 |
| 191* | 4-(trifluoromethoxy)phenyl | 10 |
| 192* | 2-quinolinyl | 40 |
| 193* | 4-bromophenyl | 20 |
| 194* | pentafluorophenyl | 30 |
| 195* | 2,5-dichlorophenyl | 50 |
| 196* | 2,3,5,6-tetrafluoro-4-(trifluoromethyl)phenyl | 20 |
| 197* | 2-(4-methylpyrimidinyl) | 60 |
| 198* | 4-nitrophenyl | 7 |
| 199* | 4-methoxyphenyl | 20 |
| 200* | 2-chlorophenyl | 40 |
| 201* | 2,6-dichlorophenyl | 30 |
| 202* | 8-quinolinyl | 80 |
| 203* | 2-pyrimidinyl | 70 |
| 204* | 4-(acetylamino)phenyl | >100[B] |
| 205* | 2-benzoxazolyl | 20 |
| 206* | 4-bromo-2-(trifluoromethoxy)phenyl | 50 |
| 207* | 3-aminophenyl | 100 |
| 208* | 2-methoxyphenyl | 60 |
| 209* | 2-(5-methylbenzimidazolyl) | 10 |
| 210* | benzoimidazol-2-yl | 20 |
| 211* | 3-methoxyphenyl | 45 |
| 212* | 2-benzothiazolyl | 15 |
| 213* | 3-chlorophenyl | 15 |
| 214* | 3,4-dichlorophenyl | 2 |
| 215* | 2-naphthyl | 2 |
| 216* | 2-pyridyl | 40 |
| 217* | 2-bromophenyl | 50 |
| 218* | [3-(carbomethoxy)-2-(difluoromethyl)-4-isobutyl-6-(trifluoromethyl)-5-pyridyl]methyl | 30 |

[A]90% CE transferred @ 100 $\mu$m.
[B]80% CE transferred @ 100 $\mu$m.

TABLE 7

(T-7)

| Compound | R | $IC_{50}$ ($\mu$m) |
|---|---|---|
| 219 | phenyl | 25 |
| 220 | 4-chlorophenyl | 20 |
| 221 | 4-methoxyphenyl | 40 |
| 222 | 3,4-dibenzyloxyphenyl | 15 |
| 223 | 2-nitrophenyl | 50 |
| 224 | 4-benzyloxyphenyl | 25 |
| 225 | 4-biphenyl | 10 |
| 226* | 2-chloro-3,4-methylenedioxyphenyl | 60 |
| 227 | 9-anthryl | 30 |
| 228 | 3,5-bis(trifluoromethyl)phenyl | 50 |
| 229 | 3-bromophenyl | 50 |
| 230 | 3-nitrophenyl | 50 |
| 231 | 3-methoxyphenyl | 50 |
| 232 | 4-t-butyiphenyl | 35 |
| 233* | 2-pyridyl | 60 |
| 234 | 2,4-bis(trifluoromethyl)phenyl | 20 |
| 235 | 4-(trifluoromethoxy)phenyl | 30 |
| 236 | 3,4-dichlorophenyl | 40 |
| 237 | 2,4-dichlorophenyl | 30 |
| 238 | 1-naphthyl | 45 |
| 239 | 2-bromophenyl | 45 |
| 240 | 2,6-dichlorophenyl | 50 |
| 241* | 2-quinolinyl | 50 |
| 242 | 3-phenoxyphenyl | 20 |
| 243 | 3,5-dichlorophenyl | 50 |
| 244 | pentafluorophenyl | 50 |
| 245* | 1,2,3,4-tetrahydro-1,1,4,4-teoramethyl-6-naphthyl | 30 |
| 246* | 8-(6-chloro-1,3-benzodioxanyl) | 30 |

TABLE 8

| Compound Number | Structure | IC$_{50}$ ($\mu$M) |
| --- | --- | --- |
| 247 | (structure) | 5 |
| 248 | (structure) | 77 |
| 249 | (structure) | 5 |
| 250 | (structure) | 40 |
| 251 | (structure) | 7 |

TABLE 8-continued
| Compound Number | Structure | IC$_{50}$ ($\mu$M) |
|---|---|---|
| 252 | 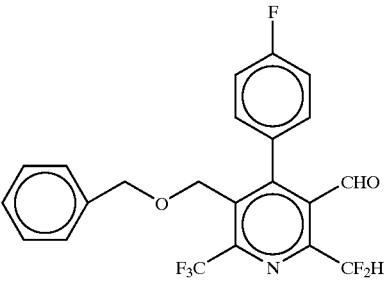 | 4.5 |
| 253 | 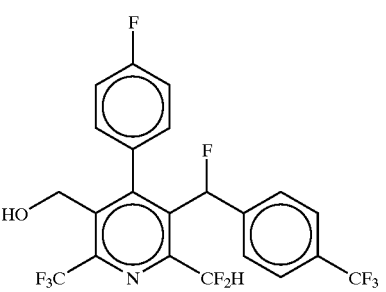 | 19 |
| 254 | 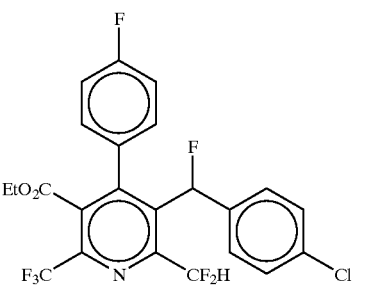 | 55 |
| 255 | 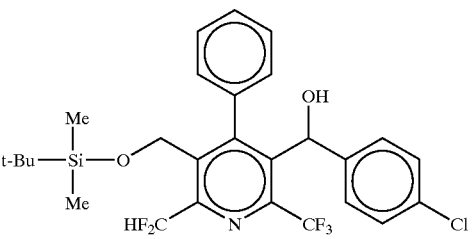 | |
| 256 | 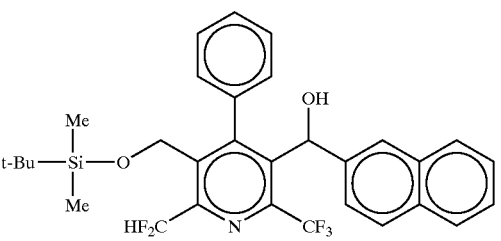 | |

TABLE 8-continued

| Compound Number | Structure | IC$_{50}$ ($\mu$M) |
|---|---|---|
| 257 | 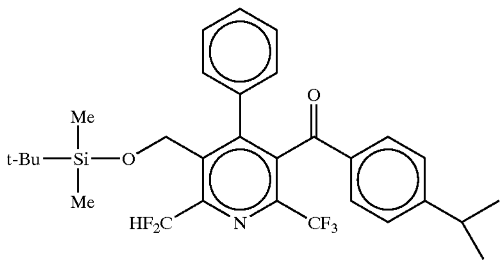 | |
| 258 | 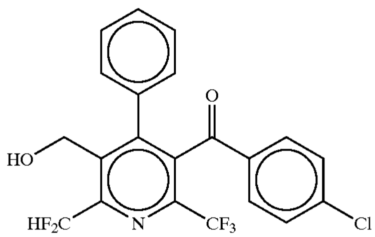 | 15 |
| 259 | 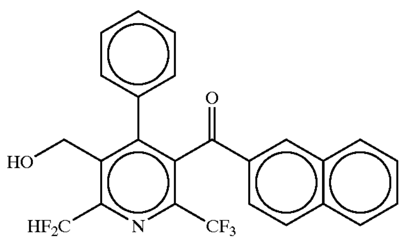 | 60 |
| 260 | 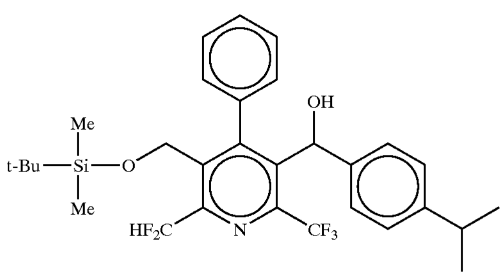 | |
| 261 | 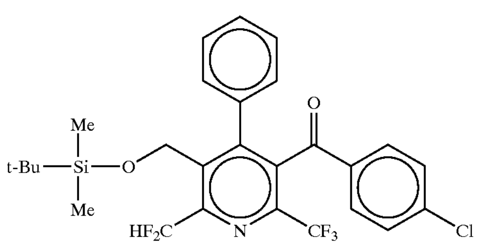 | |
| 262 | 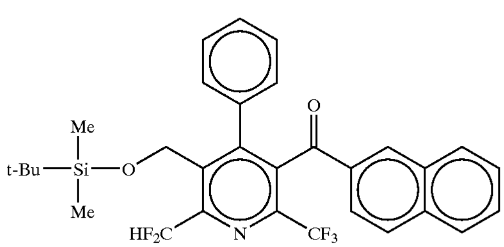 | |

TABLE 8-continued

| Compound Number | Structure | IC$_{50}$ ($\mu$M) |
|---|---|---|
| 263 | 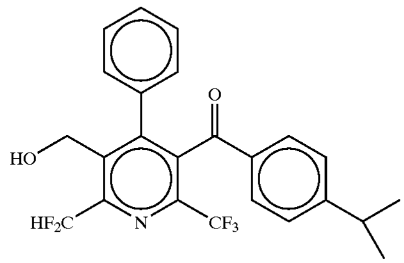 | 40 |
| 264 | 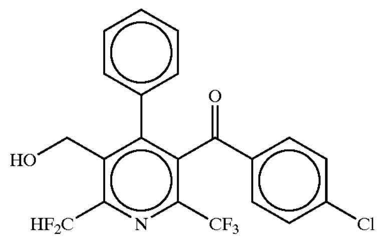 | 30 |
| 265 | 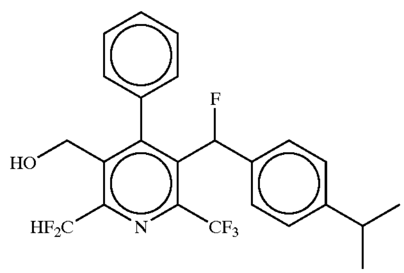 | 60 |
| 266 | 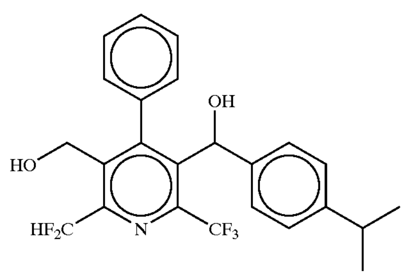 | >100 |
| 267 | 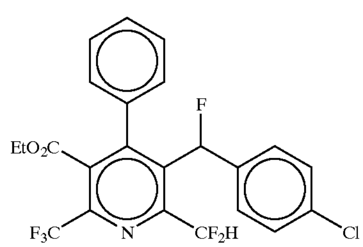 | 70 |
| 268 | 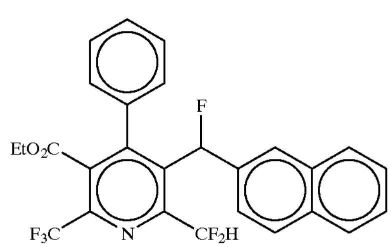 | 70 |

TABLE 8-continued

| Compound Number | Structure | IC$_{50}$ ($\mu$M) |
|---|---|---|
| 269 | 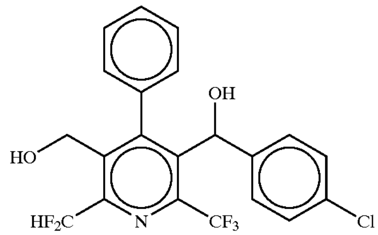 | >100 |
| 270 | 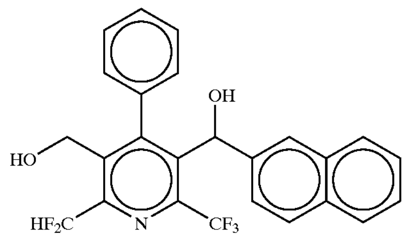 | >100 |
| 271 | 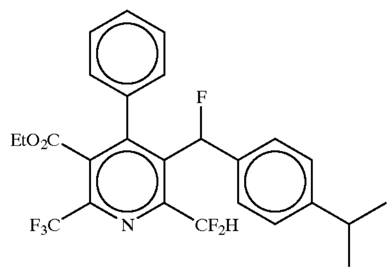 | 70 |
| 272 | 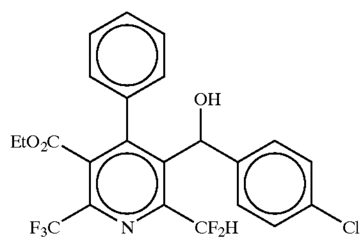 | 90 |
| 273 | 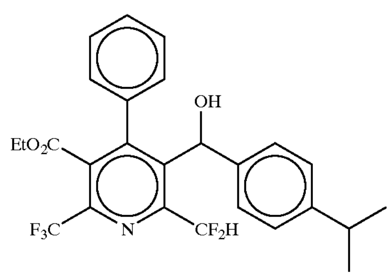 | 100 |
| 274 | 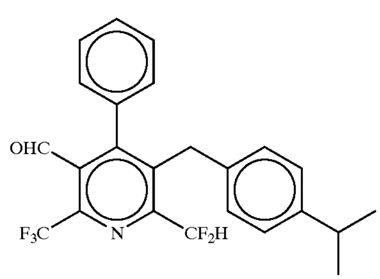 | 8 |

TABLE 8-continued

| Compound Number | Structure | IC$_{50}$ ($\mu$M) |
|---|---|---|
| 275 | 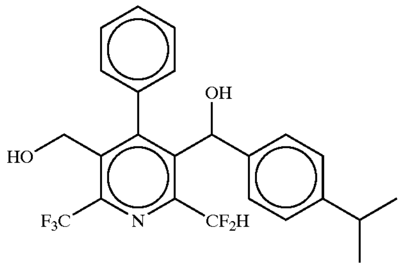 | >100 |
| 276 | 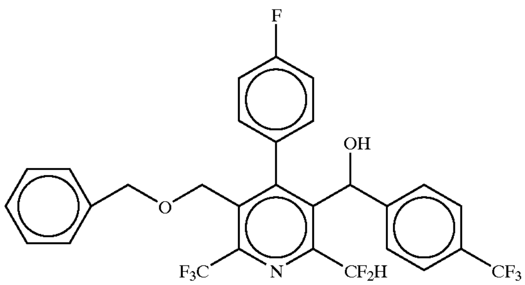 | >100 |
| 277 | 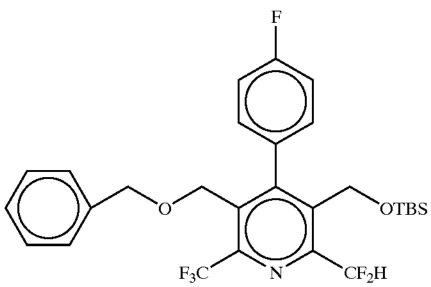 | |
| 278 | 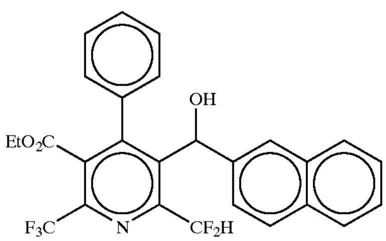 | 80 |
| 279 | 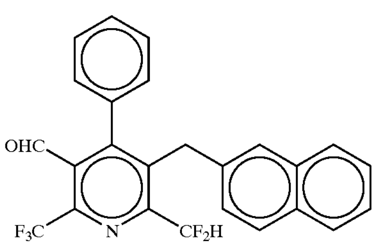 | 15 |
| 280 | 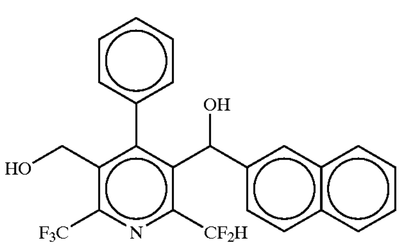 | >100 |

TABLE 8-continued
| Compound Number | Structure | IC$_{50}$ ($\mu$M) |
|---|---|---|
| 281 | 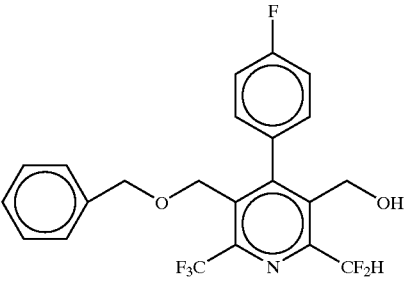 | >100 |
| 282 | 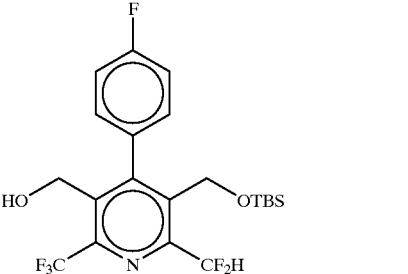 | |
| 283 | 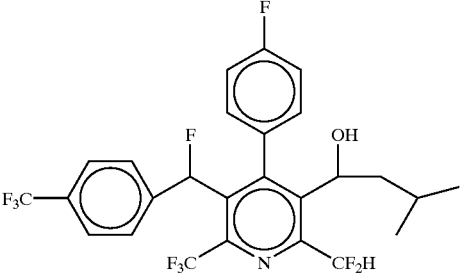 | 38.7 |
| 284 | 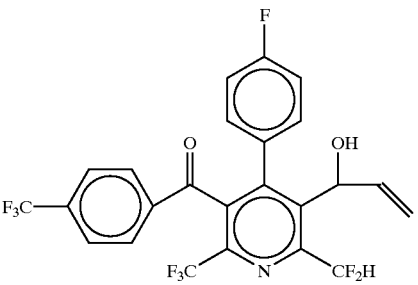 | 22.7 |
| 285 | 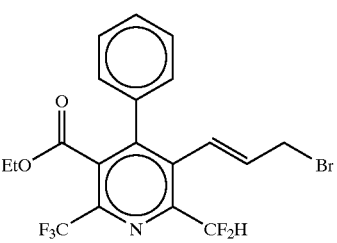 | |

TABLE 8-continued

| Compound Number | Structure | IC$_{50}$ ($\mu$M) |
| --- | --- | --- |
| 286 | (structure) | 11.7 |
| 287 | (structure) | |
| 288 | (structure) | 19 |
| 289 | (structure) | 55.3 |
| 290 | (structure) | 12.2 |
| 291 | (structure) | |

TABLE 8-continued

| Compound Number | Structure | IC$_{50}$ ($\mu$M) |
|---|---|---|
| 292 | 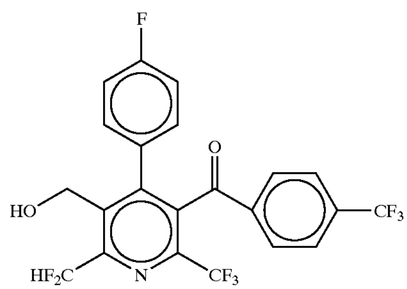 | 16.2 |
| 293 | 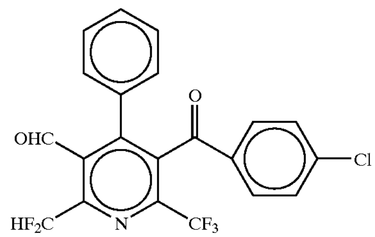 | 10.2 |
| 294 | 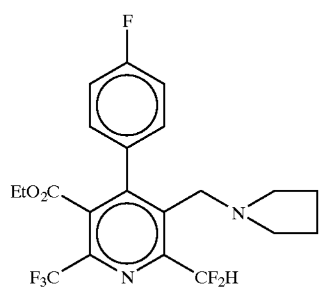 | 40 |
| 295 | 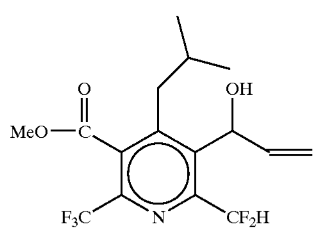 | >100 |
| 296 | 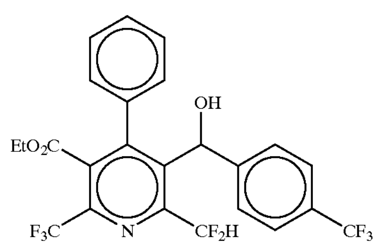 | >100 |
| 297 | 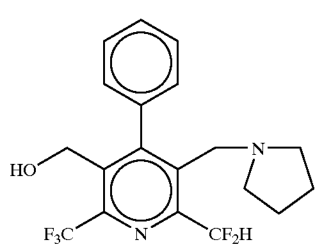 | >100 |

In yet another embodiment, the method comprises the administration of a therapeutically effective amount of the compound of Formula IA wherein:

$R_2$ is selected from the group consisting of alkyl and fluorinated alkyl;

$R_3$ is selected from the group consisting of —$CO_2R_7$, wherein $R_7$ is selected from the group consisting of hydrogen and alkyl;

$R_4$ is selected from the group consisting of alkyl, cycloalkyl, arylcarbonyloxy, thio, arylthio, and heterocyclylthio, $R_5$ is selected from the group consisting of alkyl, heterocyclyl, arylthioalkyl, heteroarylthioalkyl,

wherein $R_{14}$ is alkyl;

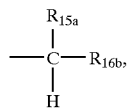

wherein $R_{15b}$ is hydroxy, and $R_{16b}$ is heteroaryl;

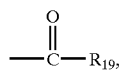

wherein $R_{19}$ is —$SR_{20}$, and $R_{20}$ is alkyl;

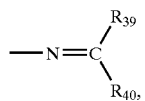

wherein $R_{39}$ is alkoxy, and $R_{40}$ is haloalkyl;

—N=$R_{41}$, wherein $R_{41}$ is heterocyclylidenyl;

—N=S=O;

—$SR_{45}$, wherein $R_{45}$ is selected from the group consisting of hydrogen, —$SR_{46}$, and —$CH_2R_{47}$, wherein $R_{46}$ is selected from the group consisting of aryl and heteroaryl, and $R_{47}$ is selected from the group consisting of aryl and heteroaryl; and

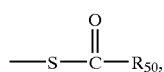

wherein $R_{50}$ is selected from the group consisting of alkyl and alkoxy;

$R_6$ is selected from the group consisting of alkyl and fluorinated alkyl;

or a pharmaceutically acceptable salt or tautomer thereof; provided that:

when $R_2$ is trifluoromethyl, $R_3$ is $CO_2CH_3$, $R_4$ is isobutyl, and $R_5$ is —$CO_2CH_3$, then $R_6$ is selected from the group consisting of alkyl comprising at least two carbon atoms and fluorinated alkyl.

In yet another embodiment, the method comprises the administration of a therapeutically effective amount of the compound of Formula IA which is selected from the compounds disclosed below:

Methyl 5-[(4-t-Butylphenyl)thiomethyl]-2-(difluoromethyl)-4-(2-methylpropyl))-6-(trifluoromethyl)-3-pyridinecarboxylate (Compound 180);

Methyl 2-(Difluoromethyl)-4-(2-methylpropyl)-5-(palmitoylthio)-6-(trifluoromethyl)-3-pyridinecarboxylate (Compound 5);

Methyl 2-(Difluoromethyl)-5-(methoxycarbonylthio)-4-(2-methylpropyl)-6-(trifluoromethyl)-3-pyridinecarboxylate (Compound 6);

Diethyl 2,6-Bis(trifluoromethyl)-4-(trimethylsilyl)-3,5-pyridinedicarboxylate (Compound 31);

Methyl 2-(Difluoromethyl)-4-(2-methylpropyl)-5-(methylthiomethylthio)-6-(trifluoromethyl)-3-pyridinecarboxylate (Compound 33);

Methyl 5-(1-Bromo-2-methoxyethenyl)-4-(cyclopropylmethyl)-2-(difluoromethyl)-6-(trifluoromethyl)-3-pyridinecarboxylate (Compound 35);

Methyl 5-(Chloroethylthio)-2-(difluoromethyl)-4-(2-methylpropyl)-6-(trifluoromethyl)-3-pyridinecarboxylate (Compound 44);

Methyl 4-(i-Propoxy)-5-{[3-(methoxycarbonyl)-4-(i-propoxy-)-6-(trifluoromethyl)-5-pyridyl]carbonyl}-6-(trifluoromethyl)-3-pyridinecarboxylate (Compound 54);

Methyl 2-(Difluoromethyl)-4-cyclobutyl-5-(1-pyrrolyl)-6-(trifluoromethyl)-3-pyridinecarboxylate (Compound 70);

Methyl 2-(Difluoromethyl)-4-(2-methylpropyl)-5-(aminothionocarbonyl)-6-(trifluoromethyl)-3-pyridinecarboxylate (Compound 77);

Methyl 2-(Difluoromethyl)-4-(2-methylpropyl)-5-{[(dimethylamino)carbonyl]thiomethyl}-6-(trifluoromethyl)-3-pyridinecarboxylate (Compound 79);

Methyl 2-(Difluoromethyl)-5-[(diethylphosphono)carbonyl]-4-(i-propylamino)-6-(trifluoromethyl)-3-pyridinecarboxylate (Compound 85);

Dimethyl 2,6-Bis(methoxymethyl)-4-propyl-3,5-pyridinecarboxylate (Compound 92);

Methyl 5-[(Aminocarbonyl)methylthio]-2-(difluoromethyl)-4-(2-methylpropyl-6-(trifluoromethyl)-3-pyridinecarboxylate (Compound 145);

Methyl 2-(Difluoromethyl)-5-(1-ethoxyethylthio)-4-(2-methylpropyl)-6-(trifluoromethyl)-3-pyridinecarboxylate (Compound 146);

Methyl 2-(Difluoromethyl)-4-(2-methylpropyl)-5-(1-methoxyethylthio)-6-(trifluoromethyl)-3-pyridinecarboxylate (Compound 147);

Methyl 2-(Difluoromethyl)-5-(2-fluoroethylthio)4-(2-methylpropyl)-6-(trifluoromethyl)-3-pyridinecarboxylate (Compound 148);

Methyl 5-(Acetylthio)-2-(difluoromethyl)-4-(2-methylpropyl)-6-(trifluoromethyl)-3-pyridinecarboxylate (Compound 149);

Methyl 2-(Difluoromethyl)-4-(2-methylpropyl)-5-(2-tetrhydrofurylthio)-6-(trifluoromethyl)-3-pyridinecarboxylate (Compound 150);

Methyl 2-(Difluoromethyl)-5-{[(3,5-di-t-butylphenyl)thio]carbonyl}-4-(2-methylpropyl)-6-(trifluoromethyl)-3-pyridinecarboxylate (Compound 151);

Methyl 2-(Difluoromethyl)-5-{[(2,4-dimethylphenyl)thio]carbonyl}-4-(2-methylpropyl)-6-(trifluoromethyl)-3-pyridinecarboxylate (Compound 152);

Methyl 2-(Difluoromethyl)-4-(2-methylpropyl)-5-{[(2-methoxyphenyl)thio]carbonyl}-6-(trifluoromethyl)-3-pyridinecarboxylate (Compound 153);

Methyl 2-(Difluoromethyl)-4-(2-methylpropyl)-5-{[(3-methoxyphenyl)thio]carbonyl}-6-(trifluoromethyl)-3-pyridinecarboxylate (Compound 154);

Methyl 2-(Difluoromethyl)-5-{[(2,4-di-t-butylphenyl)thio]carbonyl}-4-(2-methylpropyl)-6-(trifluoromethyl)-3-pyridinecarboxylate (Compound 155);

Methyl 5-{[(4-t-Butylphenyl)thio]carbonyl}-2-(difluoromethyl)-4-(2-methylpropyl)-6-(trifluoromethyl)-3-pyridinecarboxylate (Compound 156);

Methyl 2-(Difluoromethyl)-4-(2-methylpropyl)-5-{[(2-isopropylphenyl)thio]carbonyl}-6-(trifluoromethyl)-3-pyridinecarboxylate (Compound 157);

Methyl 2-(Difluoromethyl)-5-{[(3,5-dimethylphenyl)thio]carbonyl}-4-(2-methylpropyl)-6-(trifluoromethyl)-3-pyridinecarboxylate (Compound 158);

Methyl 2-(Difluoromethyl)-4-(2-methylpropyl)-5-{[(4-methylthiophenyl)thio]carbonyl}-6-(trifluoromethyl)-3-pyridinecarboxylate (Compound 159);

Methyl 2-(Difluoromethyl)-4-(2-methylpropyl)-5-{[(2-(4-fluorobenzyl)-4-isopropylphenyl)thio]carbonyl}-6-(trifluoromethyl)-3-pyridinecarboxylate (Compound 160);

Methyl 2-(Difluoromethyl)-4-(2-methylpropyl)-5-{[(2-(4-fluorobenzyl)-4-fluorophenyl)thio]carbonyl}-6-(trifluoromethyl)-3-pyridinecarboxylate (Compound 161);

Methyl 5-{[(4-chlorophenyl)thio]carbonyl}-2-(difluoromethyl)-4-(2-methylpropyl)-6-(trifluoromethyl)-3-pyridinecarboxylate (Compound 162);

Methyl 5-{[(2,5-Dichlorophenyl)thio]carbonyl}-2-(difluoromethyl)-4-(2-methylpropyl)-6-(trifluoromethyl)-3-pyridinecarboxylate (Compound 163);

Methyl 5-{[(2,6-Dichlorophenyl)thio]carbonyl}-2-(difluoromethyl)-4-(2-methylpropyl)-6-(trifluoromethyl)-3-pyridinecarboxylate (Compound 164);

Methyl 2-(Difluoromethyl)-4-(2-methylpropyl)-5-{[(2-naphthyl)thio]carbonyl}-6-(trifluoromethyl)-3-pyridinecarboxylate (Compound 178);

Methyl 2-(Difluoromethyl)-4-(2-methylpropyl)-5-{[(1-naphthyl)thio]carbonyl}-6-(trifluoromethyl)-3-pyridinecarboxylate (Compound 179);

3-Methyl 5-(3-Methoxyphenyl) 2-(Difluoromethyl)-4-(2-methylpropyl)-6-(trifluoromethyl)-3,5-pyridicarboxylate (Compound 165);

3-Methyl 5-(2-Nitrophenyl) 2-(Difluoromethyl)-4-(2-methylpropyl)-6-(trifluoromethyl)-3,5-pyridicarboxylate (Compound 166);

3-Methyl 5-(3,5-Di-t-butylphenyl) 2-(Difluoromethyl)-4-(2-methylpropyl)-6-(trifluoromethyl)-3,5-pyridicarboxylate (Compound 167);

3-Methyl 5-(2,4-Di-t-butylphenyl) 2-(Difluoromethyl)-4-(2-methylpropyl)-6-(trifluoromethyl)-3,5-pyridicarboxylate (Compound 168);

3-Methyl 5-(4-t-Butylphenyl) 2-(Difluoromethyl)-4-(2-methylpropyl)-6-(trifluoromethyl)-3,5-pyridicarboxylate (Compound 169);

3-Methyl 5-[2-(4-Fluorobenzyl)-4-isopropylphenyl]2-(Difluoromethyl)-4-(2-methylpropyl)-6-(trifluoromethyl)-3,5-pyridicarboxylate (Compound 170);

3-Methyl 5-[2-(4-Fluorobenzyl)-3,4,5-(trimethoxy)phenyl]2-(Difluoromethyl)-4-(2-methylpropyl)-6-(trifluoromethyl)-3,5-pyridicarboxylate (Compound 171);

3-Methyl 5-(2-Methoxyphenyl) 2-(Difluoromethyl)-4-(2-methylpropyl)-6-(trifluoromethyl)-3,5-pyridicarboxylate (Compound 172);

3-Methyl 5-(4-Chlorophenyl) 2-(Difluoromethyl)-4-(2-methylpropyl)-6-(trifluoromethyl)-3,5-pyridicarboxylate (Compound 173);

3-Methyl 5-(3,5-Dimethylphenyl) 2-(Difluoromethyl)-4-(2-methylpropyl)-6-(trifluoromethyl)-3,5-pyridicarboxylate (Compound 174);

3-Methyl 5-(2-Isopropylphenyl) 2-(Difluoromethyl)-4-(2-methylpropyl)-6-(trifluoromethyl)-3,5-pyridicarboxylate (Compound 175);

3-Methyl 5-(2,6-Dimethyl-4-nitrophenyl) 2-(Difluoromethyl)-4-(2-methylpropyl)-6-(trifluoromethyl)-3,5-pyridicarboxylate (Compound 176);

3-Methyl 5-(2,4-Dimethylphenyl) 2-(Difluoromethyl)-4-(2-methylpropyl)-6-(trifluoromethyl)-3,5-pyridicarboxylate (Compound 177);

Methyl 5-(4-t-Butylphenyldithio)-2-(difluoromethyl)-4-(2-methylpropyl)-6-(trifluoromethyl)-3-pyridinecarboxylate (Compound 180);

Dimethyl 5,5'-Dithiobis[2-(Difluoromethyl)-4-(2-methylpropyl)-6-(trifluoromethyl)-3-pyridinecarboxylate](Compound 181);

Methyl 5-{[2-(Difluoromethyl)-4-(2-methylpropyl)-3-(methoxycarbonyl)-6-(trifluoromethyl)-5-pyridyl]methylthio}-2-(difluoromethyl)-4-(2-methylpropyl)-6-(trifluoromethyl)-3-pyridinecarboxylate (Compound 182);

Methyl 5-{[2-(Difluoromethyl)-4-(2-methylpropyl)-3-(methoxycarbonyl)-6-(trifluoromethyl)-5-pyridyl]carbonylthio}-2-(difluoromethyl)-4-(2-methylpropyl)-6-(trifluoromethyl)-3-pyridinecarboxylate (Compound 183);

Methyl 5-[(3-Bromophenyl)thiomethyl]-2-(difluoromethyl)-4-(2-methylpropyl)-6-(trifluoromethyl)-3-pyridinecarboxylate (Compound 184);

Methyl 5-[(4-Chlorophenyl)thiomethyl]-2-(difluoromethyl)-4-(2-methylpropyl)-6-(trifluoromethyl)-3-pyridinecarboxylate (Compound 185);

Methyl 5-[(2,3,5,6-Tetrafluorophenyl)thiomethyl]-2-(difluoromethyl)-4-(2-methylpropyl)-6-(trifluoromethyl)-3-pyridinecarboxylate (Compound 186);

Methyl 5-[(3,5-Di-t-butylphenyl)thiomethyl]-2-(difluoromethyl)-4-(2-methylpropyl)-6-(trifluoromethyl)-3-pyridinecarboxylate (Compound 187);

Methyl 5-[(1-Methylimidazol-2-yl)thiomethyl]-2-(difluoromethyl)-4-(2-methylpropyl)-6-(trifluoromethyl)-3-pyridinecarboxylate (Compound 188);

Methyl 5-[(1-Methyltetrazol-5-yl)thiomethyl]-2-(difluoromethyl)-4-(2-methylpropyl)-6-(trifluoromethyl)-3-pyridinecarboxylate (Compound 189);

Methyl 5-[(5-Nitrobenzimidazol-2-yl)thiomethyl]-2-(difluoromethyl)-4-(2-methylpropyl)-6-(trifluoromethyl)-3-pyridinecarboxylate (Compound 190);

Methyl 5-[(4-(Trifluoromethoxy)phenyl))thiomethyl]-2-(difluoromethyl)-4-(2-methylpropyl)-6-(trifluoromethyl)-3-pyridinecarboxylate (Compound 191);

Methyl 5-[(Quinolin-2-yl)thiomethyl]-2-(difluoromethyl)-4-(2-methylpropyl)-6-(trifluoromethyl)-3-pyridinecarboxylate (Compound 192);

Methyl 5-[(4-Bromophenyl)thiomethyl]-2-(difluoromethyl)-4-(2-methylpropyl)-6-(trifluoromethyl)-3-pyridinecarboxylate (Compound 193);

Methyl 5-[(Pentafluorophenyl)thiomethyl]-2-(difluoromethyl)-4-(2-methylpropyl)-6-(trifluoromethyl)-3-pyridinecarboxylate (Compound 194);

Methyl 5-[(2,5-Dichlorophenyl)thiomethyl]-2-(difluoromethyl)-4-(2-methylpropyl)-6-(trifluoromethyl)-3-pyridinecarboxylate (Compound 195);

Methyl 5-[(2,3,5,6-Tetrafluoro-4-(trifluoromethyl)phenyl)thiomethyl]-2-(difluoromethyl)-4-(2-methylpropyl)-6-(trifluoromethyl)-3-pyridinecarboxylate (Compound 196);

Methyl 5-[(4-Methylpyrimidin-2-yl)thiomethyl]-2-(difluoromethyl)-4-(2-methylpropyl)-6-(trifluoromethyl)-3-pyridinecarboxylate (Compound 197);

Methyl 5-[(4-Nitrophenyl)thiomethyl]-2-(difluoromethyl)-4-(2-methylpropyl)-6-(trifluoromethyl)-3-pyridinecarboxylate (Compound 198);

Methyl 5-[(4-Methoxyphenyl)thiomethyl]-2-(difluoromethyl)-4-(2-methylpropyl)-6-(trifluoromethyl)-3-pyridinecarboxylate (Compound 199);

Methyl 5-[(2-Chlorophenyl)thiomethyl]-2-(difluoromethyl)-4-(2-methylpropyl)-6-(trifluoromethyl)-3-pyridinecarboxylate (Compound 200);

Methyl 5-[(2,6-Dichlorophenyl)thiomethyl]-2-(difluoromethyl)-4-(2-methylpropyl)-6-(trifluoromethyl)-3-pyridinecarboxylate (Compound 201);

Methyl 5-[(Quinolin-8-yl)thiomethyl]-2-(difluoromethyl)-4-(2-methylpropyl)-6-(trifluoromethyl)-3-pyridinecarboxylate (Compound 202);

Methyl 5-[(Pyrimidin-2-yl)thiomethyl]-2-(difluoromethyl)-4-(2-methylpropyl)-6-(trifluoromethyl)-3-pyridinecarboxylate (Compound 203);

Methyl 5-[(4-(Acetylamino)phenyl)thiomethyl]-2-(difluoromethyl)-4-(2-methylpropyl)-6-(trifluoromethyl)-3-pyridinecarboxylate (Compound 204);

Methyl 5-[(Benzoxazol-2-yl)thiomethyl]-2-(difluoromethyl)-4-(2-methylpropyl)-6-(trifluoromethyl)-3-pyridinecarboxylate (Compound 205);

Methyl 5-[(4-Bromo-2-(trifluoromethoxy)phenyl)thiomethyl]-2-(difluoromethyl)-4-(2-methylpropyl)-6-(trifluoromethyl)-3-pyridinecarboxylate (Compound 206);

Methyl 5-[(3-Aminophenyl)thiomethyl)-2-(difluoromethyl)-4-(2-methylpropyl)-6-(trifluoromethyl)-3-pyridinecarboxylate (Compound 207);

Methyl 5-[(2-Methoxyphenyl)thiomethyl]-2-(difluoromethyl)-4-(2-methylpropyl)-6-(trifluoromethyl)-3-pyridinecarboxylate (Compound 208);

Methyl 5-[(5-Methylbenzimidazol-2-yl)thiomethyl]-2-(difluoromethyl)-4-(2-methylpropyl)-6-(trifluoromethyl)-3-pyridinecarboxylate (Compound 209);

Methyl 5-[(Benzimidazol-2-yl)thiomethyl]-2-(difluoromethyl)-4-(2-methylpropyl)-6-(trifluoromethyl)-3-pyridinecarboxylate (Compound 210);

Methyl 5-[(3-Methoxyphenyl)thiomethyl]-2-(difluoromethyl)-4-(2-methylpropyl)-6-(trifluoromethyl)-3-pyridinecarboxylate (Compound 211);

Methyl 5-[(Benzothiazol-2-yl)thiomethyl]-2-(difluoromethyl)-4-(2-methylpropyl)-6-(trifluoromethyl)-3-pyridinecarboxylate (Compound 212);

Methyl 5-[(3-Chlorophenyl)thiomethyl]-2-(difluoromethyl)-4-(2-methylpropyl)-6-(trifluoromethyl)-3-pyridinecarboxylate (Compound 213);

Methyl 5-[(3,4-Dichlorophenyl)thiomethyl]-2-(difluoromethyl)-4-(2-methylpropyl)-6-(trifluoromethyl)-3-pyridinecarboxylate (Compound 214);

Methyl 5-[(2-Naphthyl)thiomethyl]-2-(difluoromethyl)-4-(2-methylpropyl)-6-(trifluoromethyl)-3-pyridinecarboxylate (Compound 215);

Methyl 5-[(2-Pyridyl)thiomethyl]-2-(difluoromethyl)-4-(2-methylpropyl)-6-(trifluoromethyl)-3-pyridinecarboxylate (Compound 216);

Methyl 5-[(2-bromophenyl)thiomethyl]-2-(difluoromethyl)-4-(2-methylpropyl)-6-(trifluoromethyl)-3-pyridinecarboxylate (Compound 217);

Bis{3-(carbomethoxy)-2-(difluoromethyl)-4-(2-methylpropyl)-6-(trifluoromethyl)-5-pyridyl]methyl Sulfide (Compound 218);

Methyl 5-[(2-Chloro-3,4-methylenedioxyphenyl)methylthio]-2-(difluoromethyl)-4-(2-methylpropyl)-6-(trifluoromethyl)-3-pyridinecarboxylate (Compound 226);

Methyl 5-[(2-pyridyl)methylthio]-2-(difluoromethyl)-4-(2-methylpropyl)-6-(trifluoromethyl)-3-pyridinecarboxylate (Compound 233);

Methyl 5-[(2-quinolinyl)methylthio]-2-(difluoromethyl)-4-(2-methylpropyl)-6-(trifluoromethyl)-3-pyridinecarboxylate (Compound 241);

Methyl 5-[(1,2,3,4-tetrahydro-1,1,4,4-tetramethyl-6-naphthyl)methylthio]-2-(difluoromethyl)-4-(2-methylpropyl)-6-(trifluoromethyl)-3-pyridinecarboxylate (Compound 245);

Methyl 5[(6-chloro-1,3-benzodioxan-8-yl)methylthio]-2-(difluoromethyl)-4-(2-methylpropyl)-6-(trifluoromethyl)-3-pyridinecarboxylate (Compound 246);

Diethyl 5,5'-(Carbonyldiimino)bis[6(difluoromethyl)-4-ethyl-2-(trifluoromethyl)-3-pyridinecarboxylate (Compound 48);

Methyl 2-(Difluoromethyl)-4-(2-methylpropyl)-5-{[(dimethylamino)thiono]thiomethyl}-6-(trifluoromethyl)-3-pyridinecarboxylate (Compound 43);

2-(Difluoromethyl)-5-hydroxymethyl-4-phenyl-6-(trifluoromethyl)-3-{[4-(trifluoromethyl)phenyl]hydroxymethyl}pyridine;

2-(Difluoromethyl)-5-hydroxymethyl-4-phenyl-6-(trifluoromethyl)-3-{[4-(trifluoromethyl)phenyl]carbonyl}pyridine;

2-(Difluoromethyl)-5-hydroxymethyl-4-(4-fluorophenyl)-6-(trifluoromethyl)-3-{[4-(trifluoromethyl)phenyl]hydroxymethyl}pyridine;

2-(Difluoromethyl)-5-hydroxymethyl-4-(4-fluorophenyl)-6-(trifluoromethyl)-3-{[4-(trifluoromethyl)phenyl]carbonyl}pyridine;

2-(Difluoromethyl)-5-hydroxymethyl-4-(4-fluorophenyl)-6-(trifluoromethyl)-3-{[4-(trifluoromethyl)phenyl]fluoromethyl}pyridine;

2-(Difluoromethyl)-5-hydroxymethyl-4-(4-fluorophenyl)-6-(trifluoromethyl)-3-{[4-(trifluoromethyl)phenyl]fluoromethyl}pyridine;

2-(Difluoromethyl)-5-hydroxymethyl-4-(4-fluorophenyl)-6-(trifluoromethyl)-3-(2-naphthylfluoromethyl)pyridine;

2-(Difluoromethyl)-5-hydroxymethyl-4-(4-fluorophenyl)-6-(trifluoromethyl)-3-{[4-(trifluoromethyl)phenyl]mercaptomethyl}pyridine;

2-(Difluoromethyl)-5-hydroxymethyl-4-phenyl-6-(trifluoromethyl)-3-{[4-(trifluoromethyl)phenyl]mercaptomethyl}pyridine;

2-(Cyclopentyl)-5-hydroxymethyl-4-(4-fluorophenyl)-6-(trifluoromethyl)-3-{[4-(trifluoromethyl)phenyl]carbonyl}pyridine;

2-(1-Pyrrolidinyl)-5-hydroxymethyl-4-(4-fluorophenyl)-6-(trifluoromethyl)-3-{[4-(trifluoromethyl)phenyl]carbonyl}pyridine;

2-(1-Pyrrolidinyl)-5-hydroxymethyl-4-(4-fluorophenyl)-6-(trifluoromethyl)-3-{[4-(trifluoromethyl)phenyl]hydroxymethyl}pyridine; and 2-(1-Pyrrolidinyl)-5-hydroxymethyl-4-(4-fluorophenyl)-6-(trifluoromethyl)-3-{[4-(trifluoromethyl)phenyl]fluoromethyl}pyridine.

In yet another embodiment, the method comprises the administration of a therapeutically effective amount of the compound of Formula IA which is selected from the compounds disclosed below:

Methyl 5-(4-t-Butylphenyldithio)-2-(difluoromethyl)-4-(2-methylpropyl)-6-(trifluoromethyl)-3-pyridinecarboxylate;

Dimethyl 5,5'-Dithiobis[2-(difluoromethyl)-4-(2-methylpropyl)-6-(trifluoromethyl)-3-pyridinecarboxylate;

Methyl 5-[(3,4-Dichlorophenyl)thiomethyl]-2-(difluoromethyl)-4-(2-methylpropyl)-6-(trifluoromethyl)-3-pyridinecarboxylate;

Methyl 2-(Difluoromethyl)-5-isothiocyanato-4-(2-methylpropyl)-6-(trifluoromethyl)-3-pyridinecarboxylate;

Methyl 5-[(2-Naphthyl)thiomethyl]-2-(difluoromethyl)-4-(2-methylpropyl)-6-(trifluoromethyl)-3-pyridinecarboxylate;

Methyl 2-(difluoromethyl)-5-mercapto-4-(2-methylpropyl)-6-(trifluoromethyl)-3-pyridinecarboxylate;

5-Ethyl 3-Methyl 2-(difluoromethyl)-4-[(4,5-dihydro-2-thiazolyl)thio]-6-(trifluoromethyl)-3,5-pyridinedicarboxylate;

Methyl 5-[(4-Nitrophenyl)thiomethyl]-2-(difluoromethyl)-4-(2-methylpropyl)-6-(trifluoromethyl)-3-pyridinecarboxylate;

Methyl 2-(Difluoromethyl)-4-(2-methylpropyl)-5-(palmitoylthio)-6-(trifluoromethyl)-3-pyridinecarboxylate;

Methyl 2-(Difluoromethyl)-5-(methoxycarbonylthio)-4-(2-methylpropyl)-6-(trifluoromethyl)-3-pyridinecarboxylate;

Methyl 5-[(4-t-Butylphenyl)thiomethyl]-2-(difluoromethyl)-4-(2-methylpropyl))-6-(trifluoromethyl)-3-pyridinecarboxylate;

Methyl 2-(Difluoromethyl)-5-[(1,4-dithian-2-ylidene)amino]-4-(2-methylpropyl)-6-(trifluoromethyl)-3-pyridinecarboxylate;

Methyl 5-[(4-(Trifluoromethoxy)phenyl))thiomethyl]-2-(difluoromethyl)-4-(2-methylpropyl)-6-(trifluoromethyl)-3-pyridinecarboxylate;

Methyl 5-[(4-Chlorophenyl)thiomethyl]-2-(difluoromethyl)-4-(2-methylpropyl)-6-(trifluoromethyl)-3-pyridinecarboxylate;

Methyl 5-[(5-Methylbenzimidazol-2-yl)thiomethyl]-2-(difluoromethyl)-4-(2-methylpropyl)-6-(trifluoromethyl)-3-pyridinecarboxylate;

Methyl 5-[(Benzothiazol-2-yl)thiomethyl]-2-(difluoromethyl)-4-(2-methylpropyl)-6-(trifluoromethyl)-3-pyridinecarboxylate;

Methyl 5-[(3-Chlorophenyl)thiomethyl]-2-(difluoromethyl)-4-(2-methylpropyl)-6-(trifluoromethyl)-3-pyridinecarboxylate;

Methyl 5-{[3-(Carbomethoxy)-2-(difluoromethyl)-4-isobutyl-6-(trifluoromethyl)-5-pyridyl]thiomethyl}-2-(difluoromethyl)-4-isobutyl-6-(trifluoromethyl)-3-pyridinecarboxylate;

Di-t-Butyl 2-(difluoromethyl)-4-(2-methylpropyl)-6-(trifluoromethyl)-3,5-pyridinedicarboxylate;

Methyl 5-[(4-Bromophenyl)thiomethyl]-2-(difluoromethyl)-4-(2-methylpropyl)-6-(trifluoromethyl)-3-pyridinecarboxylate;

Methyl 5-[(2,3,5,6-Tetrafluoro-4-(trifluoromethyl)phenyl)thiomethyl]-2-(difluoromethyl)-4-(2-methylpropyl)-6-(trifluoromethyl)-3-pyridinecarboxylate;

Methyl 5-[(4-Methoxyphenyl)thiomethyl]-2-(difluoromethyl)-4-(2-methylpropyl)-6-(trifluoromethyl)-3-pyridinecarboxylate;

Methyl 5-[(Benzoxazol-2-yl)thiomethyl]-2-(difluoromethyl)-4-(2-methylpropyl)-6-(trifluoromethyl)-3-pyridinecarboxylate;

Methyl 5-[(Benzimidazol-2-yl)thiomethyl]-2-(difluoromethyl)-4-(2-methylpropyl)-6-(trifluoromethyl)-3-pyridinecarboxylate;

Methyl 2-(Difluoromethyl)-4-(2-methylpropyl)-5-(4,5-dihydro-2-thiazoyl)-6-(trifluoromethyl)-3-pyridinecarboxylate;

Ethyl 2,6-Bis(trifluoromethyl)-5-methyl-4-[4-(trifluoromethylphenyl)carbonyloxy]-3-pyridinecarboxylate;

Methyl 2-(Difluoromethyl)-5-[(i-propylthio)carbonyl]-4-(cyclobutyl)-6-(trifluoromethyl)-3-pyridinecarboxylate;

Methyl 4-(4-i-Propylphenylthio)-5-methyl-6-(trifluoromethyl)-3-pyridinecarboxylate;

Methyl 5-[(5-Nitrobenzimidazol-2-yl)thiomethyl]-2-(difluoromethyl)-4-(2-methylpropyl)-6-(trifluoromethyl)-3-pyridinecarboxylate; and In yet another embodiment, the method comprises the administration of a therapeutically effective amount of the compound of Formula IA which is Dimethyl 5,5'-dithiobis [2-difluoromethyl)-4-(2-methylpropyl)-6-(trifluoromethyl)-3-pyridinecarboxylate].

In still another embodiment, the method comprises the administration of a therapeutically effective amount of the compound of Formula IB:

(IB)

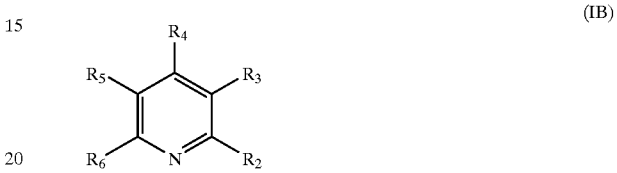

wherein:

$R_2$ and $R_6$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of $R_2$ and $R_6$ is fluorinated alkyl, chlorofluorinated alkyl or alkoxyalkyl;

$R_3$ is selected from the group consisting of hydroxy, amido, arylcarbonyl, heteroarylcarbonyl, hydroxymethyl

—CHO,

—$CO_2R_7$, wherein $R_7$ is selected from the group consisting of hydrogen, alkyl and cyanoalkyl; and

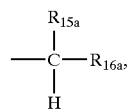

wherein $R_{15a}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy and heterocyclyloxy, and $R_{16a}$ is selected from the group consisting of alkyl, haloalkyl, alkenyl, haloalkenyl, alkynyl, haloalkynyl, aryl, heteroaryl, and heterocyclyl, arylalkoxy, trialkylsilyloxy;

$R_4$ is selected from the group consisting of hydrogen, hydroxy, halogen, alkyl, alkenyl, alkynyl, cycloalkyl, cycloalkenyl, haloalkyl, haloalkenyl, haloalkynyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkoxy, alkenoxy, alkynoxy, aryloxy, heteroaryloxy, heterocyclyloxy, alkanoyloxy, alkenoyloxy, alkynoyloxy, aryloyloxy, heteroaroyloxy, heterocyclyloyloxy, alkoxycarbonyl, alkenoxycarbonyl, alkynoxycarbonyl, aryloxycarbonyl, heteroaryloxycarbonyl, heterocyclyloxycarbonyl, thio, alkylthio, alkenylthio, alkynylthio, arylthio, heteroarylthio, heterocyclylthio, cycloalkylthio, cycloalkenylthio, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkylamino, alkenylamino, alkynylamino, arylamino, heteroarylamino, heterocyclylamino, aryldialkylamino, diarylamino, diheteroarylamino, alkylarylamino, alkylheteroarylamino, arylheteroarylamino, trialkylsilyl, trialkenylsilyl, triarylsilyl, —OC(O)N($R_{8a}R_{8b}$), wherein $R_{8a}$ and $R_{8b}$ are independently selected from the group consisting of alkyl, alkenyl, alkynyl, aryl, heteroaryl and heterocyclyl, —$SO_2R_9$, wherein $R_9$ is selected from the group consisting of hydroxy, alkyl, alkenyl, alkynyl, aryl, heteroaryl and heterocyclyl, —OP(O)($OR_{10a}$)($OR_{10b}$), wherein $R_{10a}$ and $R_{10b}$ are independently selected from the group consisting of hydrogen, hydroxy, alkyl, alkenyl, alkynyl, aryl, heteroaryl and heterocyclyl, and —OP(S)($OR_{11a}$)($OR_{11b}$), wherein $R_{11a}$ and $R_{11b}$ are independently selected from the group consisting of alkyl, alkenyl, alkynyl, aryl, heteroaryl and heterocyclyl;

$R_5$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, alkoxy, alkenoxy, alkynoxy, aryloxy, heteroaryloxy, heterocyclyloxy, alkylcarbonyloxyalkyl, alkenylcarbonyloxyalkyl, alkynylcarbonyloxyalkyl, arylcarbonyloxyalkyl, heteroarylcarbonyloxyalkyl, heterocyclylcarbonyloxyalkyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, cycloalkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkoxyalkyl, alkenoxyalkyl, alkynoxyalkyl, aryloxyalkyl, heteroaryloxyalkyl, heterocyclyloxyalkyl, alkoxyalkenyl, alkenoxyalkenyl, alkynoxyalkenyl, aryloxyalkenyl, heteroaryloxyalkenyl, heterocyclyloxyalkenyl, cyano, hydroxymethyl,

—$CO_2R_{14}$, wherein $R_{14}$ is selected from the group consisting of alkyl, alkenyl, alkynyl, aryl, heteroaryl and heterocyclyl;

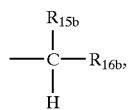

wherein $R_{15b}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy, heterocyclyloxy, aroyloxy, and alkylsulfonyloxy, and $R_{16b}$ is selected from the group consisting of alkyl, alkenyl, alkynyl, aryl, heteroaryl, heterocyclyl, arylalkoxy, and trialkylsilyloxy;

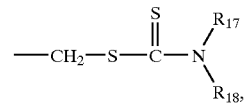

wherein $R_{17}$ and $R_{18}$ are independently selected from the group consisting of alkyl, cycloalkyl, alkenyl, alkynyl, aryl, heteroaryl and heterocyclyl;

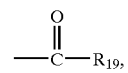

wherein $R_{19}$ is selected from the group consisting of alkyl, cycloalkyl, alkenyl, alkynyl, aryl, heteroaryl, heterocyclyl, —$SR_{20}$, —$OR_{21}$, and —$R_{22}CO_2R_{23}$, wherein $R_{20}$ is selected from the group consisting of alkyl, alkenyl, alkynyl, aryl, heteroaryl, heterocyclyl, aminoalkyl, aminoalkenyl, aminoalkynyl, aminoaryl, aminoheteroaryl, aminoheterocyclyl, alkylheteroarylamino, arylheteroarylamino, $R_{21}$ is selected from the group consisting of alkyl, alkenyl, alkynyl, aryl, heteroaryl, and heterocyclyl, $R_{22}$ is selected from the group consisting of alkylene or arylene, and $R_{23}$ is selected from the group consisting of alkyl, alkenyl, alkynyl, aryl, heteroaryl, and heterocyclyl;

wherein $R_{24}$ is selected from the group consisting of hydrogen, alkyl, cycloalkyl, alkenyl, alkynyl, aryl, heteroaryl, heterocyclyl, aralkyl, aralkenyl, and aralkynyl;

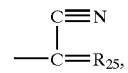

wherein $R_{25}$ is heterocyclylidenyl;

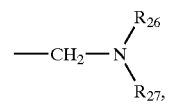

wherein $R_{26}$ and $R_{27}$ are independently selected from the group consisting of hydrogen, alkyl, cycloalkyl, alkenyl, alkynyl, aryl, heteroaryl, and heterocyclyl;

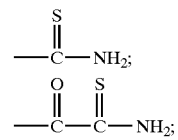

-continued $$-CH_2-S-\overset{\overset{O}{\|}}{C}-N\overset{R_{28}}{\underset{R_{29}}{\diagup}},$$

wherein $R_{28}$ and $R_{29}$ are independently selected from the group consisting of hydrogen, alkyl, cycloalkyl, alkenyl, alkynyl, aryl, heteroaryl, and heterocyclyl;

$$-\overset{\overset{O}{\|}}{C}-\overset{\overset{O}{\|}}{\underset{R_{31}}{P}}-R_{30},$$

wherein $R_{30}$ and $R_{31}$ are independently alkoxy, alkenoxy, alkynoxy, aryloxy, heteroaryloxy, and heterocyclyloxy; and $$-\overset{\overset{NR_{32}}{\|}}{C}-S-R_{33},$$

wherein $R_{32}$ and $R_{33}$ are independently selected from the group consisting of hydrogen, alkyl, cycloalkyl, alkenyl, alkynyl, aryl, heteroaryl, and heterocyclyl;

$$-\overset{\overset{H}{|}}{C}=N-OH;$$

$$-C\equiv C-Si(R_{36})_3,$$

wherein $R_{36}$ is selected from the group consisting of alkyl, alkenyl, aryl, heteroaryl and heterocyclyl;

$$-N\overset{R_{37}}{\underset{R_{38}}{\diagup}},$$

wherein $R_{37}$ and $R_{38}$ are independently selected from the group consisting of hydrogen, alkyl, cycloalkyl, alkenyl, alkynyl, aryl, heteroaryl, and heterocyclyl;

$$-N=C\overset{R_{39}}{\underset{R_{40}}{\diagup}},$$

wherein $R_{39}$ is selected from the group consisting of hydrogen, alkoxy, alkenoxy, alkynoxy, aryloxy, heteroaryloxy, heterocyclyloxy, alkylthio, alkenylthio, alkynylthio, arylthio, heteroarylthio and heterocyclylthio, and $R_{40}$ is selected from the group consisting of haloalkyl, haloalkenyl, haloalkynyl, haloaryl, haloheteroaryl, haloheterocyclyl, cycloalkyl, cycloalkenyl, heterocyclylalkoxy, heterocyclylalkenoxy, heterocyclylalkynoxy, alkylthio, alkenylthio, alkynylthio, arylthio, heteroarylthio and heterocyclylthio;

$$-N=R_{41},$$

wherein $R_{41}$ is heterocyclylidenyl;

$$-NR_{42}-\overset{\overset{O}{\|}}{C}-R_{43},$$

wherein $R_{42}$ is selected from the group consisting of hydrogen, alkyl, alkenyl, alkynyl, aryl, heteroaryl, and heterocyclyl, and $R_{43}$ is selected from the group consisting of hydrogen, alkyl, alkenyl, alkynyl, aryl, heteroaryl, heterocyclyl, cycloalkyl, cycloalkenyl, haloalkyl, haloalkenyl, haloalkynyl, haloaryl, haloheteroaryl, and haloheterocyclyl;

$$-NH-\overset{\overset{O}{\|}}{C}-NH-R_{44},$$

wherein $R_{44}$ is selected from the group consisting of hydrogen, alkyl, cycloalkyl, alkenyl, alkynyl, aryl, heteroaryl and heterocyclyl;

—N=S=O;

—N=C=S;

—N=C=O;

—$N_3$;

—$SR_{45}$, wherein $R_{45}$ is selected from the group consisting of hydrogen, alkyl, alkenyl, alkynyl, aryl, heteroaryl, heterocyclyl, haloalkyl, haloalkenyl, haloalkynyl, haloaryl, haloheteroaryl, haloheterocyclyl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, aminocarbonylalkyl, aminocarbonylalkenyl, aminocarbonylalkynyl, aminocarbonylaryl, aminocarbonylheteroaryl, and aminocarbonylheterocyclyl, —$SR_{46}$, and —$CH_2R_{47}$, wherein $R_{46}$ is selected from the group consisting of alkyl, alkenyl, alkynyl, aryl, heteroaryl and heterocyclyl, and $R_{47}$ is selected from the group consisting of hydrogen, alkyl, alkenyl, alkynyl, aryl, heteroaryl and heterocyclyl; and $$-S-CH\overset{R_{48}}{\underset{R_{49}}{\diagup}},$$

wherein $R_{48}$ is selected from the group consisting of hydrogen, alkyl, cycloalkyl, alkenyl, alkynyl, aryl, heteroaryl and heterocyclyl, and $R_{49}$ is selected from the group consisting of alkoxy, alkenoxy, alkynoxy, aryloxy, heteroaryloxy, heterocyclyloxy, haloalkyl, haloalkenyl, haloalkynyl, haloaryl, haloheteroaryl and haloheterocyclyl;

$$-S-\overset{O}{\underset{\|}{C}}-R_{50},$$

wherein $R_{50}$ is selected from the group consisting of hydrogen, alkyl, cycloalkyl, alkenyl, alkynyl, aryl, heteroaryl, heterocyclyl, alkoxy, alkenoxy, alkynoxy, aryloxy, heteroaryloxy and heterocyclyloxy;

$$-\overset{O}{\underset{\|}{S}}-R_{51},$$

wherein $R_{51}$ is selected from the group consisting of alkyl, alkenyl, alkynyl, aryl, heteroaryl, heterocyclyl, haloalkyl, haloalkenyl, haloalkynyl, haloaryl, haloheteroaryl and haloheterocyclyl; and $$-\overset{O}{\underset{\underset{O}{\|}}{\overset{\|}{S}}}-R_{53},$$

wherein $R_{53}$ is selected from the group consisting of alkyl, alkenyl, alkynyl, aryl, heteroaryl and heterocyclyl;

or a pharmaceutically acceptable salt or tautomer thereof, provided that when $R_5$ is selected from the group consisting of heterocyclylalkyl and heterocyclylalkenyl, the heterocyclyl radical of the corresponding heterocyclylalkyl or heterocyclylalkenyl is other than a δ-lactone; and provided that when $R_4$ is aryl, heteroaryl or heterocyclyl, and one of $R_2$ and $R_6$ is trifluoromethyl, then the other of $R_2$ and $R_6$ is difluoromethyl.

Novel Compounds

The present invention also relates to a class of novel substituted pyridines which are beneficial in the therapeutic and prophylactic treatment of CTEP-mediated disorders (such as coronary artery disease) as given in Formula IIA:

(IIA)

wherein:

$R_2$ and $R_6$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of $R_2$ and $R_6$ is fluorinated alkyl, chlorofluorinated alkyl or alkoxyalkyl;

$R_3$ is selected from the group consisting of arylcarbonyl, heteroarylcarbonyl, hydroxymethyl, arylalkoxyalkyl, trialkylsilyloxyalkyl,

—CHO,

—$CO_2R_7$, wherein $R_7$ is selected from the group consisting of hydrogen and alkyl (preferably methyl or ethyl); and $$-\underset{H}{\overset{R_{15a}}{\underset{|}{C}}}-R_{16a},$$

wherein $R_{15a}$ is selected from the group consisting of hydroxy, halogen, alkylthio and alkoxy, and $R_{16a}$ is selected from the group consisting of alkyl, haloalkyl, alkenyl, aryl and heteroaryl;

$R_4$ is selected from the group consisting of hydrogen, hydroxy, alkyl, aryl, cycloalkyl, cycloalkylalkyl, heteroarylalkyl, alkoxy, thio, trialkylsilyl, alkylamino, and —OC(O)N($R_8$)$_2$, wherein $R_8$ is aryl;

$R_5$ is selected from the group consisting of hydrogen, alkyl, haloalkyl, alkenyl, haloalkenyl, alkynyl, haloalkynyl, aralkyl, alkoxy, aryloxy, cycloalkylthioalkyl, arylthioalkyl, heteroarylthioalkyl, alkoxyalkenyl, arylcarbonyloxyalkyl, pyrrolyl, substituted pyrrolidinyl, hydroxymethyl, arylalkoxyalkyl, and trialkylsilyloxyalkyl,

—$CO_2R_{14}$, wherein $R_{14}$ is alkyl;

$$-\underset{H}{\overset{R_{15b}}{\underset{|}{C}}}-R_{16b},$$

wherein $R_{15b}$ is selected from the group consisting of hydroxy, halogen, alkoxy, and alkylthio, aroyloxy, and alkylsulfonyloxy, and $R_{16b}$ is selected from the group consisting of alkyl, alkenyl, aryl, and heteroaryl;

$$-CH_2-S-\overset{S}{\underset{\|}{C}}-N\overset{R_{17}}{\underset{R_{18},}{\diagdown}}$$

wherein $R_{17}$ and $R_{18}$ are independently alkyl;

$$-\overset{O}{\underset{\|}{C}}-R_{19},$$

wherein $R_{19}$ is aryl, heteroaryl, —$SR_{20}$, and —$OR_{21}$, wherein $R_{20}$ is selected from the group consisting of aryl, heteroaryl and aminoalkyl, and $R_{21}$ is selected from the group consisting of aryl and heteroaryl;

$$-\overset{O}{\underset{\|}{C}}-NH-R_{24},$$

wherein $R_{24}$ is aralkyl (preferably halo-substituted aralkyl);

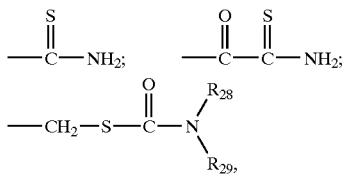

wherein $R_{28}$ and $R_{29}$ are independently alkyl;

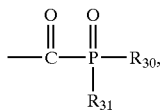

wherein $R_{30}$ and $R_{31}$ are independently alkoxy;

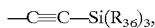

wherein $R_{36}$ is alkyl;

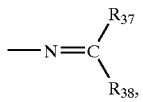

wherein $R_{37}$ is selected from the group consisting of hydrogen, alkoxy, and alkylthio, and $R_{38}$ is selected from the group consisting of haloalkyl, cycloalkyl, heterocyclylalkoxy, and alkylthio;

provided that when $R_{37}$ is hydrogen, then $R_{38}$ is selected from the group consisting of haloalkyl, cycloalkyl, and heterocyclylalkoxy;

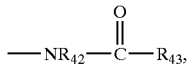

wherein $R_{42}$ is selected from the group consisting of hydrogen and alkyl, and $R_{43}$ is substituted heteroaryl;

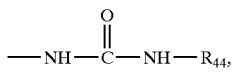

wherein $R_{44}$ is selected from the group consisting of aryl and heteroaryl;

wherein $R_{45}$ is selected from the group consisting of haloalkyl, heterocyclyl, alkylthioalkyl, aminocarbonylalkyl, —$SR_{46}$, and —$CH_2R_{47}$, wherein $R_{46}$ is selected from the group consisting of aryl (preferably substituted aryl) and heteroaryl (preferably substituted pyridyl), and $R_{47}$ is selected from the group consisting of methylenedioxyphenyl, pyridyl, quinolinyl, tetrahydronaphthyl and benzodioxanyl;

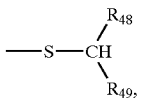

wherein $R_{48}$ is selected from the group consisting of hydrogen and alkyl, and $R_{49}$ is selected from the group consisting of alkoxy and haloalkyl;

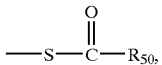

wherein $R_{50}$ is selected from the group consisting of alkyl, alkoxy, and heteroaryl (preferably substituted heteroaryl); and

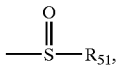

wherein $R_{51}$ is haloalkyl;

or a pharmaceutically acceptable salt or tautomer thereof, provided that:

when $R_2$ is selected from the group consisting of difluoromethyl and trifluoromethyl, $R_3$ is selected from the group consisting of —$CO_2H$, —$CO_2CH_3$ and —$CO_2C_2H_5$, $R_5$ is hydrogen, and $R_6$ is selected from the group consisting of hydrogen and trifluoromethyl, then $R_4$ is selected from the group consisting of cycloalkyl, cycloalkylalkyl, heteroarylalkyl, aralkenyl, alkoxy, thio, trialkylsilyl, alkylamino, and —$OC(O)N(R_8)_2$, wherein $R_8$ is aryl; provided further that when $R_2$, $R_3$ and $R_5$ are as defined above, and $R_4$ is alkoxy, then $R_6$ is hydrogen;

when $R_2$ is selected from the group consisting of fluorinated methyl and chlorofluorinated methyl, $R_3$ is selected from the group consisting of hydroxymethyl and $CO_2R_7$, $R_5$ is selected from the group consisting of hydroxymethyl and $CO_2R_{14}$, $R_6$ is selected from the group consisting of fluorinated methyl and chlorofluorinated methyl, and $R_7$ and $R_{14}$ are independently alkyl, then $R_4$ is selected from the group consisting of hydrogen, thio, trialkylsilyl, and —$OC(O)N(R_8)_2$, wherein $R_8$ is aryl;

when $R_2$ is difluoromethyl, $R_3$ is —$CO_2C_2H_5$, $R_4$ is hydrogen, $R_5$ is —$CO_2C_2H_5$, then $R_6$ is selected from the group consisting of monofluoroalkyl, difluoroalkyl and alkoxyalkyl;

when $R_2$ is trifluoromethyl, $R_3$ is —$CO_2R_7$, $R_5$ is methyl, $R_6$ is selected from the group consisting of fluorinated methyl, fluorinated ethyl and chlorofluorinated methyl, and $R_7$ is selected from the group consisting of hydrogen and alkyl, then $R_4$ is selected from the group consisting of hydrogen, alkyl, cycloalkyl, cycloalkylalkyl, heteroarylalkyl, thio, trialkylsilyl, and —$OC(O)N(R_8)_2$, wherein $R_8$ is aryl; and when $R_4$ is selected from the group consisting of alkyl, cycloalkyl and cycloalkylalkyl, $R_3$ is —$CO_2R_7$, and $R_7$ is alkyl, then $R_5$ is other than arylcarbonyl, heteroarylcarbonyl or

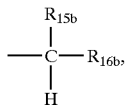

wherein $R_{16b}$ is alkyl when $R_{15b}$ is selected from the group consisting of hydroxy, halogen, alkylthio and alkoxy, or wherein $R_{16b}$ is aryl or heteroaryl when $R_{15b}$ is hydroxy;

when $R_4$ is selected from the group consisting of alkyl, cycloalkyl and cycloalkylalkyl, $R_5$ is —$CO_2R_{14}$, and $R_{14}$ is alkyl, then $R_3$ is other than arylcarbonyl, heteroarylcarbonyl or

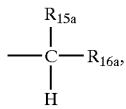

wherein $R_{16a}$ is alkyl when $R_{15a}$ is selected from the group consisting of hydroxy, halogen, alkylthio and alkoxy, or wherein $R_{16a}$ is aryl or heteroaryl when $R_{15a}$ is hydroxy; and when $R_2$ and $R_6$ are independently selected from fluorinated methyl and chlorofluorinated methyl, $R_3$ is $CO_2R_7$, $R_5$ is hydroxy, alkoxy or aryloxy, then $R_4$ is selected from the group consisting of aryl, cycloalkyl, cycloalkylalkyl, heteroarylalkyl, thio, trialkylsilyl, alkylamino, and —OC(O)N($R_8$)$_2$, wherein $R_8$ is aryl; and when $R_4$ is aryl and one of $R_2$ and $R_6$ is trifluoromethyl, then the other of $R_2$ and $R_6$ is difluoromethyl.

In one embodiment, the novel compounds comprise a compound of Formula IIA as described above wherein:
$R_2$ is fluorinated methyl; and
$R_3$ is —$CO_2R_7$, wherein $R_7$ is selected from the group consisting of hydrogen, methyl and ethyl.

The compounds of Formula IIA are capable of inhibiting the activity of cholesteryl ester transfer protein (CETP), and thus could be used in the manufacture of a medicament or a method for the prophylactic or therapeutic treatment of diseases mediated by CETP, such as coronary artery disease, peripheral vascular disease, hyperlipidemia, hypercholesterolemia, and other diseases attributable to either high LDL and low HDL or a combination of both. The compounds of Formula IIA would be also useful in prevention of cerebral vascular accident (CVA) or stroke.

In another embodiment, the novel compounds comprise a compound of Formula IIA wherein:
$R_2$ is fluorinated alkyl;
$R_3$ is —$CO_2R_7$, wherein $R_7$ is selected from the group consisting of hydrogen and alkyl;
$R_4$ is selected from the group consisting of alkyl and cycloalkyl;
$R_5$ is selected from the group consisting of:
1-pyrrolyl;

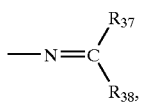

wherein $R_{37}$ is selected from the group consisting of hydrogen, alkoxy, and alkylthio, and
$R_{38}$ is selected from the group consisting of haloalkyl, cycloalkyl, heterocyclylalkoxy, and alkylthio;
provided that when $R_{37}$ is hydrogen, then $R_{38}$ is selected from the group consisting of haloalkyl, cycloalkyl, and heterocyclylalkoxy;

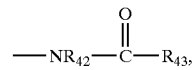

wherein $R_{42}$ is selected from the group consisting of hydrogen and alkyl, and
$R_{43}$ is substituted heteroaryl;

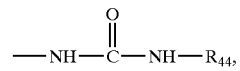

wherein $R_{44}$ is pyridyl; and
$R_6$ is fluorinated alkyl;
or a pharmaceutically acceptable salt or tautomer thereof.

In yet another embodiment, the novel compounds comprise a compound of Formula IIA wherein:
$R_2$ is fluorinated alkyl;
$R_3$ is —$CO_2R_7$, wherein $R_7$ is selected from the group consisting of hydrogen and alkyl;
$R_4$ is alkyl;
$R_5$ is selected from the group consisting of:

—$SR_{45}$ wherein $R_{45}$ is selected from the group consisting of haloalkyl, heterocyclyl, aralkyl, heteroaralkyl, alkylthioalkyl, aminocarbonylalkyl, —$SR_{46}$, and —$CH_2R_{47}$,
wherein $R_{46}$ is selected from the group consisting of aryl (preferably substituted aryl) and heteroaryl (preferably substituted pyridyl), and
$R_{47}$ is selected from the group consisting of methylenedioxyphenyl, pyridyl, quinolinyl, tetrahydronaphthyl and benzodioxanyl; and

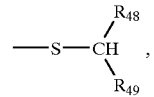

wherein $R_{48}$ is selected from the group consisting of hydrogen and alkyl, and
$R_{49}$ is selected from the group consisting of alkoxy and haloalkyl;

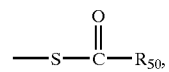

wherein $R_{50}$ is selected from the group consisting of alkyl, alkoxy, and heteroaryl (preferably substituted heteroaryl);

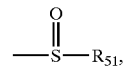

wherein $R_{51}$ is haloalkyl; and
$R_6$ is fluorinated alkyl;
or a pharmaceutically acceptable salt or tautomer thereof.

In yet another embodiment, the novel compounds comprise a compound of Formula IIA wherein:

$R_2$ is fluorinated alkyl;

$R_3$ is —$CO_2R_7$, wherein $R_7$ is selected from the group consisting of hydrogen and alkyl;

$R_4$ is hydroxy, alkoxy, —OC(O)N($R_8$)$_2$, or —OP(O)(O$R_{10}$)$_2$, wherein $R_8$ is aryl and $R_{10}$ is alkyl;

$R_5$ is selected from the group consisting of hydrogen, alkoxy and aryloxy; and $R_6$ is selected from the group consisting of hydrogen and fluorinated alkyl;

or a pharmaceutically acceptable salt or tautomer thereof;

provided that when $R_2$ is trifluoromethyl, $R_3$ is selected from the group consisting of —$CO_2CH_3$ and —$CO_2C_2H_5$, $R_5$ is hydrogen, and $R_6$ is selected from the group consisting of hydrogen and trifluoromethyl, then $R_4$ is selected from the group consisting of alkoxy, —OC(O)N($R_8$)$_2$, or —OP(O)(O$R_{10}$)$_2$, wherein $R_8$ is aryl and $R_{10}$ is alkyl; provided further that when $R_2$, $R_3$ and $R_5$ are as defined above, and $R_4$ is alkoxy, then $R_6$ is hydrogen.

In yet another preferred embodiment, the novel compounds comprise a compound of Formula IIA wherein:

$R_2$ is fluorinated alkyl;

$R_3$ is —$CO_2R_7$, wherein $R_7$ is selected from the group consisting of hydrogen and alkyl;

$R_4$ is selected from the group consisting of alkyl, alkoxy, cycloalkyl, cycloalkylalkyl, arylthio (preferably substituted arylthio), and alkylamino; and $R_5$ is selected from the group consisting of alkyl, arylcarbonyloxyalkyl, arylthioalkyl, heteroarylthioalkyl, alkoxyalkenyl (preferably halo-substituted alkoxyalkenyl and more preferably bromo-substituted alkoxyalkenyl), substituted pyrrolidinyl,

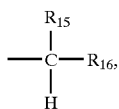

wherein $R_{15}$ is alkoxy, and $R_{16}$ is heteroaryl;

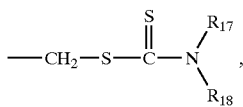

wherein $R_{17}$ and $R_{18}$ are independently alkyl;

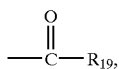

wherein $R_{19}$ is selected from the group consisting of pyridyl, —S$R_{20}$, and —O$R_{21}$, wherein $R_{20}$ is selected from the group consisting of aryl, heteroaryl and aminoalkyl, and $R_{21}$ is selected from the group consisting of aryl and heteroaryl;

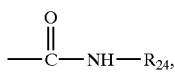

wherein $R_{24}$ is aralkyl (preferably halo-substituted aralkyl);

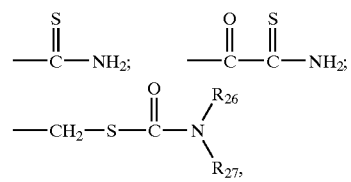

wherein $R_{26}$ and $R_{27}$ are independently alkyl;

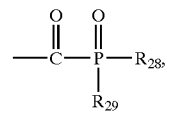

wherein $R_{28}$ and $R_{29}$ are independently alkoxy; and

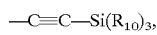

wherein $R_{10}$ is alkyl; and $R_6$ is selected from the group consisting of hydrogen and fluorinated alkyl;

or a pharmaceutically acceptable salt or tautomer thereof;

provided that:

when $R_2$ is trifluoromethyl, $R_3$ is —$CO_2C_2H_5$, $R_4$ is isopropoxy, $R_5$ is methyl, then $R_6$ is hydrogen; and when $R_5$ is alkyl, then $R_4$ is selected from the group consisting of cycloalkyl, cycloalkylalkyl, arylthio, and alkylamino.

In yet another embodiment, the novel compounds comprise a compound of Formula IIA wherein:

$R_2$ is selected from the group consisting of fluorinated alkyl and alkoxyalkyl;

$R_3$ is —$CO_2R_7$, wherein $R_7$ is selected from the group consisting of hydrogen and alkyl;

$R_4$ is selected from the group consisting of hydrogen, hydroxy, alkyl, heteroarylalkyl, thio, and trialkylsilyl;

$R_5$ is $CO_2R_{14}$, wherein $R_{14}$ is alkyl; and $R_6$ is selected from the group consisting of hydrogen, fluorinated alkyl, and alkoxyalkyl;

or a pharmaceutically acceptable salt or tautomer thereof;

provided that when $R_2$ is difluoromethyl, $R_3$ is —$CO_2C_2H_5$, $R_4$ is hydrogen, $R_5$ is $CO_2C_2H_5$, then $R_6$ is selected from the group consisting of hydrogen, monofluoroalkyl, and difluoroalkyl.

In yet another embodiment, the novel compounds are compounds of Formula IIA wherein:

$R_2$ is selected from the group consisting of alkyl and fluorinated alkyl;

$R_3$ is selected from the group consisting of —$CO_2R_7$, wherein $R_7$ is selected from the group consisting of hydrogen and alkyl;

$R_4$ is selected from the group consisting of alkyl and thio;

$R_5$ is selected from the group consisting of heterocyclyl, arylthioalkyl, heteroarylthioalkyl,

wherein $R_{14}$ is alkyl;

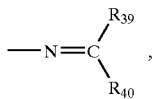

wherein $R_{39}$ is alkoxy, and
$R_{40}$ is haloalkyl;

—$SR_{45}$, wherein $R_{45}$ is selected from the group consisting of hydrogen, —$SR_{46}$, and —$CH_2R_{47}$,
wherein $R_{46}$ is selected from the group consisting of aryl and heteroaryl, and
$R_{47}$ is selected from the group consisting of methylenedioxyphenyl, pyridyl, quinolinyl, naphthyl and benzodioxanyl; and

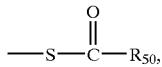

wherein $R_{50}$ is selected from the group consisting of alkyl and alkoxy; and
$R_6$ is selected from the group consisting of alkyl and fluorinated alkyl;
or a pharmaceutically acceptable salt or tautomer thereof, provided that when $R_2$ is trifluoromethyl, $R_3$ is $CO_2CH_3$, $R_4$ is isobutyl, and $R_5$ is $CO_2CH_3$, then $R_6$ is selected from the group consisting of alkyl comprising at least two carbon atoms and fluorinated alkyl.

In yet another embodiment, the novel compounds of Formula IIA are selected from the compounds listed below:

Methyl 5-[(4-t-Butylphenyl)thiomethyl]-2-(difluoromethyl)-4-(2-methylpropyl))-6-(trifluoromethyl)-3-pyridinecarboxylate (Compound 180);

Methyl 2-(Difluoromethyl)-4-(2-methylpropyl)-5-(palmitoylthio)-6-(trifluoromethyl)-3-pyridinecarboxylate (Compound 5);

Methyl 2-(Difluoromethyl)-5-(methoxycarbonylthio)-4-(2-methylpropyl)-6-(trifluoromethyl)-3-pyridinecarboxylate (Compound 6);

Diethyl 2,6-Bis(trifluoromethyl)-4-(trimethylsilyl)-3,5-pyridinedicarboxylate (Compound 31);

Methyl 2-(Difluoromethyl)-4-(2-methylpropyl)-5-(methylthiomethylthio)-6-(trifluoromethyl)-3-pyridinecarboxylate (Compound 33);

Methyl 5-(1-Bromo-2-methoxyethenyl)-4-(cyclopropylmethyl)-2-(difluoromethyl)-6-(trifluoromethyl)-3-pyridinecarboxylate (Compound 35);

Methyl 5-(Chloroethylthio)-2-(difluoromethyl)-4-(2-methylpropyl)-6-(trifluoromethyl)-3-pyridinecarboxylate (Compound 44);

Methyl 4-(i-Propoxy)-5-{[3-(methoxycarbonyl)-4-(i-propoxy-)-6-(trifluoromethyl)-5-pyridyl]carbonyl}-6-(trifluoromethyl)-3-pyridinecarboxylate (Compound 54);

Methyl 2-(Difluoromethyl)-4-cyclobutyl-5-(1-pyrrolyl)-6-(trifluoromethyl)-3-pyridinecarboxylate (Compound 70);

Methyl 2-(Difluoromethyl)-4-(2-methylpropyl)-5-(aminothionocarbonyl)-6-(trifluoromethyl)-3-pyridinecarboxylate (Compound 77);

Methyl 2-(Difluoromethyl)-4-(2-methylpropyl)-5-{[(dimethylamino)carbonyl]thiomethyl}-6-(trifluoromethyl)-3-pyridinecarboxylate (Compound 79);

Methyl 2-(Difluoromethyl)-5-[(diethylphosphono)carbonyl]-4-(i-propylamino)-6-(trifluoromethyl)-3-pyridinecarboxylate (Compound 85);

Dimethyl 2,6-Bis(methoxymethyl)-4-propyl-3,5-pyridinecarboxylate (Compound 92);

Methyl 5-[(Aminocarbonyl)methylthio]-2-(difluoromethyl)-4-(2-methylpropyl-6-(trifluoromethyl)-3-pyridinecarboxylate (Compound 145);

Methyl 2-(Difluoromethyl)-5-(1-ethoxyethylthio)-4-(2-methylpropyl)-6-(trifluoromethyl)-3-pyridinecarboxylate (Compound 146);

Methyl 2-(Difluoromethyl)-4-(2-methylpropyl)-5-(1-methoxyethylthio)-6-(trifluoromethyl)-3-pyridinecarboxylate (Compound 147);

Methyl 2-(Difluoromethyl)-5-(2-fluoroethylthio)4-(2-methylpropyl)-6-(trifluoromethyl)-3-pyridinecarboxylate (Compound 148);

Methyl 5-(Acetylthio)-2-(difluoromethyl)-4-(2-methylpropyl)-6-(trifluoromethyl)-3-pyridinecarboxylate (Compound 149);

Methyl 2-(Difluoromethyl)-4-(2-methylpropyl)-5-(2-tetrhydrofurylthio)-6-(trifluoromethyl)-3-pyridinecarboxylate (Compound 150);

Methyl 2-(Difluoromethyl)-5-{[(3,5-di-t-butylphenyl)thio]carbonyl}-4-(2-methylpropyl)-6-(trifluoromethyl)-3-pyridinecarboxylate (Compound 151);

Methyl 2-(Difluoromethyl)-5-{[(2,4-dimethylphenyl)thio]carbonyl}-4-(2-methylpropyl)-6-(trifluoromethyl)-3-pyridinecarboxylate (Compound 152);

Methyl 2-(Difluoromethyl)-4-(2-methylpropyl)-5-{[(2-methoxyphenyl)thio]carbonyl}-6-(trifluoromethyl)-3-pyridinecarboxylate (Compound 153);

Methyl 2-(Difluoromethyl)-4-(2-methylpropyl)-5-{[(3-methoxyphenyl)thio]carbonyl}-6-(trifluoromethyl)-3-pyridinecarboxylate (Compound 154);

Methyl 2-(Difluoromethyl)-5-{[(2,4-di-t-butylphenyl)thio]carbonyl}-4-(2-methylpropyl)-6-(trifluoromethyl)-3-pyridinecarboxylate (Compound 155);

Methyl 5-{[(4-t-Butylphenyl)thio]carbonyl}-2-(difluoromethyl)-4-(2-methylpropyl)-6-(trifluoromethyl)-3-pyridinecarboxylate (Compound 156);

Methyl 2-(Difluoromethyl)-4-(2-methylpropyl)-5-{[(2-isopropylphenyl)thio]carbonyl}-6-(trifluoromethyl)-3-pyridinecarboxylate (Compound 157);

Methyl 2-(Difluoromethyl)-5-{[(3,5-dimethylphenyl)thio]carbonyl}-4-(2-methylpropyl)-6-(trifluoromethyl)-3-pyridinecarboxylate (Compound 158);

Methyl 2-(Difluoromethyl)-4-(2-methylpropyl)-5-{[(4-methylthiophenyl)thio]carbonyl}-6-(trifluoromethyl)-3-pyridinecarboxylate (Compound 159);

Methyl 2-(Difluoromethyl)-4-(2-methylpropyl)-5-{[(2-(4-fluorobenzyl)-4-isopropylphenyl)thio]carbonyl}-6-(trifluoromethyl)-3-pyridinecarboxylate (Compound 160);

Methyl 2-(Difluoromethyl)-4-(2-methylpropyl)-5-{[(2-(4-fluorobenzyl)-4-fluorophenyl)thio]carbonyl}-6-(trifluoromethyl)-3-pyridinecarboxylate (Compound 161);

Methyl 5-{[(4-chlorophenyl)thio]carbonyl}-2-(difluoromethyl)-4-(2-methylpropyl)-6-(trifluoromethyl)-3-pyridinecarboxylate (Compound 162);

Methyl 5-{[(2,5-Dichlorophenyl)thio]carbonyl}-2-(difluoromethyl)-4-(2-methylpropyl)-6-(trifluoromethyl)-3-pyridinecarboxylate (Compound 163);

Methyl 5-{[(2,6-Dichlorophenyl)thio]carbonyl}-2-(difluoromethyl)-4-(2-methylpropyl)-6-(trifluoromethyl)-3-pyridinecarboxylate (Compound 164);

Methyl 2-(Difluoromethyl)-4-(2-methylpropyl)-5-{[(2-naphthyl)thio]carbonyl)-6-(trifluoromethyl)-3-pyridinecarboxylate (Compound 178);

Methyl 2-(Difluoromethyl)-4-(2-methylpropyl)-5-{[(1-naphthyl)thio]carbonyl)-6-(trifluoromethyl)-3-pyridinecarboxylate (Compound 179);

3-Methyl 5-(3-Methoxyphenyl) 2-(Difluoromethyl)-4-(2-methylpropyl)-6-(trifluoromethyl)-3,5-pyridicarboxylate (Compound 165);

3-Methyl 5-(2-Nitrophenyl) 2-(Difluoromethyl)-4-(2-methylpropyl)-6-(trifluoromethyl)-3,5-pyridicarboxylate (Compound 166);

3-Methyl 5-(3,5-Di-t-butylphenyl) 2-(Difluoromethyl)-4-(2-methylpropyl)-6-(trifluoromethyl)-3,5-pyridicarboxylate (Compound 167);

3-Methyl 5-(2,4-Di-t-butylphenyl) 2-(Difluoromethyl)-4-(2-methylpropyl)-6-(trifluoromethyl)-3,5-pyridicarboxylate (Compound 168);

3-Methyl 5-(4-t-Butylphenyl) 2-(Difluoromethyl)-4-(2-methylpropyl)-6-(trifluoromethyl)-3,5-pyridicarboxylate (Compound 169);

3-Methyl 5-[2-(4-Fluorobenzyl)-4-isopropylphenyl]2-(Difluoromethyl)-4-(2-methylpropyl)-6-(trifluoromethyl)-3,5-pyridicarboxylate (Compound 170);

3-Methyl 5-[2-(4-Fluorobenzyl)-3,4,5-(trimethoxy)phenyl] 2-(Difluoromethyl)-4-(2-methylpropyl)-6-(trifluoromethyl)-3,5-pyridicarboxylate (Compound 171);

3-Methyl 5-(2-Methoxyphenyl) 2-(Difluoromethyl)-4-(2-methylpropyl)-6-(trifluoromethyl)-3,5-pyridicarboxylate (Compound 172);

3-Methyl 5-(4-Chlorophenyl) 2-(Difluoromethyl)-4-(2-methylpropyl)-6-(trifluoromethyl)-3,5-pyridicarboxylate (Compound 173);

3-Methyl 5-(3,5-Dimethylphenyl) 2-(Difluoromethyl)-4-(2-methylpropyl)-6-(trifluoromethyl)-3,5-pyridicarboxylate (Compound 174);

3-Methyl 5-(2-Isopropylphenyl) 2-(Difluoromethyl)-4-(2-methylpropyl)-6-(trifluoromethyl)-3,5-pyridicarboxylate (Compound 175);

3-Methyl 5-(2,6-Dimethyl-4-nitrophenyl) 2-(Difluoromethyl)-4-(2-methylpropyl)-6-(trifluoromethyl)-3,5-pyridicarboxylate (Compound 176);

3-Methyl 5-(2,4-Dimethylphenyl) 2-(Difluoromethyl)-4-(2-methylpropyl)-6-(trifluoromethyl)-3,5-pyridicarboxylate (Compound 177);

Methyl 5-(4-t-Butylphenyldithio)-2-(difluoromethyl)-4-(2-methylpropyl)-6-(trifluoromethyl)-3-pyridinecarboxylate (Compound 180);

Dimethyl 5,5'-Dithiobis[2-(Difluoromethyl)-4-(2-methylpropyl)-6-(trifluoromethyl)-3-pyridinecarboxylate] (Compound 181);

Methyl 5-{[2-(Difluoromethyl)-4-(2-methylpropyl)-3-(methoxycarbonyl)-6-(trifluoromethyl)-5-pyridyl]methylthio}-2-(difluoromethyl)-4-(2-methylpropyl)-6-(trifluoromethyl)-3-pyridinecarboxylate (Compound 182);

Methyl 5-{[2-(Difluoromethyl)-4-(2-methylpropyl)-3-(methoxycarbonyl)-6-(trifluoromethyl)-5-pyridyl]carbonylthio}-2-(difluoromethyl)-4-(2-methylpropyl)-6-(trifluoromethyl)-3-pyridinecarboxylate (Compound 183);

Methyl 5-[(3-Bromophenyl)thiomethyl]-2-(difluoromethyl)-4-(2-methylpropyl)-6-(trifluoromethyl)-3-pyridinecarboxylate (Compound 184);

Methyl 5-[(4-Chlorophenyl)thiomethyl]-2-(difluoromethyl)-4-(2-methylpropyl)-6-(trifluoromethyl)-3-pyridinecarboxylate (Compound 185);

Methyl 5-[(2,3,5,6-Tetrafluorophenyl)thiomethyl]-2-(difluoromethyl)-4-(2-methylpropyl)-6-(trifluoromethyl)-3-pyridinecarboxylate (Compound 186);

Methyl 5-[(3,5-Di-t-butylphenyl)thiomethyl]-2-(difluoromethyl)-4-(2-methylpropyl)-6-(trifluoromethyl)-3-pyridinecarboxylate (Compound 187);

Methyl 5-[(1-Methylimidazol-2-yl)thiomethyl]-2-(difluoromethyl)-4-(2-methylpropyl)-6-(trifluoromethyl)-3-pyridinecarboxylate (Compound 188);

Methyl 5-[(1-Methyltetrazol-5-yl)thiomethyl]-2-(difluoromethyl)-4-(2-methylpropyl)-6-(trifluoromethyl)-3-pyridinecarboxylate (Compound 189);

Methyl 5-[(5-Nitrobenzimidazol-2-yl)thiomethyl]-2-(difluoromethyl)-4-(2-methylpropyl)-6-(trifluoromethyl)-3-pyridinecarboxylate (Compound 190);

Methyl 5-[(4-(Trifluoromethoxy)phenyl))thiomethyl]-2-(difluoromethyl)-4-(2-methylpropyl)-6-(trifluoromethyl)-3-pyridinecarboxylate (Compound 191);

Methyl 5-[(Quinolin-2-yl)thiomethyl]-2-(difluoromethyl)-4-(2-methylpropyl)-6-(trifluoromethyl)-3-pyridinecarboxylate (Compound 192);

Methyl 5-[(4-Bromophenyl)thiomethyl]-2-(difluoromethyl)-4-(2-methylpropyl)-6-(trifluoromethyl)-3-pyridinecarboxylate (Compound 193);

Methyl 5-[(Pentafluorophenyl)thiomethyl]-2-(difluoromethyl)-4-(2-methylpropyl)-6-(trifluoromethyl)-3-pyridinecarboxylate (Compound 194);

Methyl 5-[(2,5-Dichlorophenyl)thiomethyl]-2-(difluoromethyl)-4-(2-methylpropyl)-6-(trifluoromethyl)-3-pyridinecarboxylate (Compound 195);

Methyl 5-[(2,3,5,6-Tetrafluoro-4-(trifluoromethyl)phenyl)thiomethyl]-2-(difluoromethyl)-4-(2-methylpropyl)-6-(trifluoromethyl)-3-pyridinecarboxylate (Compound 196);

Methyl 5-[(4-Methylpyrimidin-2-yl)thiomethyl]-2-(difluoromethyl)-4-(2-methylpropyl)-6-(trifluoromethyl)-3-pyridinecarboxylate (Compound 197);

Methyl 5-[(4-Nitrophenyl)thiomethyl]-2-(difluoromethyl)-4-(2-methylpropyl)-6-(trifluoromethyl)-3-pyridinecarboxylate (Compound 198);

Methyl 5-[(4-Methoxyphenyl)thiomethyl]-2-(difluoromethyl)-4-(2-methylpropyl)-6-(trifluoromethyl)-3-pyridinecarboxylate (Compound 199);

Methyl 5-[(2-Chlorophenyl)thiomethyl]-2-(difluoromethyl)-4-(2-methylpropyl)-6-(trifluoromethyl)-3-pyridinecarboxylate (Compound 200);

Methyl 5-[(2,6-Dichlorophenyl)thiomethyl]-2-(difluoromethyl)-4-(2-methylpropyl)-6-(trifluoromethyl)-3-pyridinecarboxylate (Compound 201);

Methyl 5-[(Quinolin-8-yl)thiomethyl]-2-(difluoromethyl)-4-(2-methylpropyl)-6-(trifluoromethyl)-3-pyridinecarboxylate (Compound 202);

Methyl 5-[(Pyrimidin-2-yl)thiomethyl]-2-(difluoromethyl)-4-(2-methylpropyl)-6-(trifluoromethyl)-3-pyridinecarboxylate (Compound 203);

Methyl 5-[(4-(Acetylamino)phenyl)thiomethyl]-2-(difluoromethyl)-4-(2-methylpropyl)-6-(trifluoromethyl)-3-pyridinecarboxylate (Compound 204);

Methyl 5-[(Benzoxazol-2-yl)thiomethyl]-2-(difluoromethyl)-4-(2-methylpropyl)-6-(trifluoromethyl)-3-pyridinecarboxylate (Compound 205);

Methyl 5-[(4-Bromo-2-(trifluoromethoxy)phenyl)thiomethyl]-2-(difluoromethyl)-4-(2-methylpropyl)-6-(trifluoromethyl)-3-pyridinecarboxylate (Compound 206);

Methyl 5-[(3-Aminophenyl)thiomethyl]-2-(difluoromethyl)-4-(2-methylpropyl)-6-(trifluoromethyl)-3-pyridinecarboxylate (Compound 207);

Methyl 5-[(2-Methoxyphenyl)thiomethyl]-2-(difluoromethyl)-4-(2-methylpropyl)-6-(trifluoromethyl)-3-pyridinecarboxylate (Compound 208);

Methyl 5-[(5-Methylbenzimidazol-2-yl)thiomethyl]-2-(difluoromethyl)-4-(2-methylpropyl)-6-(trifluoromethyl)-3-pyridinecarboxylate (Compound 209);

Methyl 5-[(Benzimidazol-2-yl)thiomethyl]-2-(difluoromethyl)-4-(2-methylpropyl)-6-(trifluoromethyl)-3-pyridinecarboxylate (Compound 210);

Methyl 5-[(3-Methoxyphenyl)thiomethyl]-2-(difluoromethyl)-4-(2-methylpropyl)-6-(trifluoromethyl)-3-pyridinecarboxylate (Compound 211);

Methyl 5-[(Benzothiazol-2-yl)thiomethyl]-2-(difluoromethyl)-4-(2-methylpropyl)-6-(trifluoromethyl)-3-pyridinecarboxylate (Compound 212);

Methyl 5-[(3-Chlorophenyl)thiomethyl]-2-(difluoromethyl)-4-(2-methylpropyl)-6-(trifluoromethyl)-3-pyridinecarboxylate (Compound 213);

Methyl 5-[(3,4-Dichlorophenyl)thiomethyl]-2-(difluoromethyl)-4-(2-methylpropyl)-6-(trifluoromethyl)-3-pyridinecarboxylate (Compound 214);

Methyl 5-[(2-Naphthyl)thiomethyl]-2-(difluoromethyl)-4-(2-methylpropyl)-6-(trifluoromethyl)-3-pyridinecarboxylate (Compound 215);

Methyl 5-[(2-Pyridyl)thiomethyl]-2-(difluoromethyl)-4-(2-methylpropyl)-6-(trifluoromethyl)-3-pyridinecarboxylate (Compound 216);

Methyl 5-[(2-bromophenyl)thiomethyl]-2-(difluoromethyl)-4-(2-methylpropyl)-6-(trifluoromethyl)-3-pyridinecarboxylate (Compound 217);

Bis(3-(carbomethoxy)-2-(difluoromethyl)-4-(2-methylpropyl)-6-(trifluoromethyl)-5-pyridyl]methyl Sulfide (Compound 218);

Methyl 5-[(2-Chloro-3,4-methylenedioxyphenyl)methylthio]-2-(difluoromethyl)-4-(2-methylpropyl)-6-(trifluoromethyl)-3-pyridinecarboxylate (Compound 226);

Methyl 5-[(2-pyridyl)methylthio]-2-(difluoromethyl)-4-(2-methylpropyl)-6-(trifluoromethyl)-3-pyridinecarboxylate (Compound 233);

Methyl 5-[(2-quinolinyl)methylthio]-2-(difluoromethyl)-4-(2-methylpropyl)-6-(trifluoromethyl)-3-pyridinecarboxylate (Compound 241);

Methyl 5-[(1,2,3,4-tetrahydro-1,1,4,4-tetramethyl-6-naphthyl)methylthio]-2-(difluoromethyl)-4-(2-methylpropyl)-6-(trifluoromethyl)-3-pyridinecarboxylate (Compound 245); and Methyl 5[(6-chloro-1,3-benzodioxan-8-yl)methylthio]-2-(difluoromethyl)-4-(2-methylpropyl)-6-(trifluoromethyl)-3-pyridinecarboxylate (Compound 246);

Diethyl 5,5'-(Carbonyldiimino)bis[6(difluoromethyl)-4-ethyl-2-(trifluoromethyl)-3-pyridinecarboxylate (Compound 48);

Methyl 2-(Difluoromethyl)-4-(2-methylpropyl)-5-{[(dimethylamino)thiono]thiomethyl}-6-(trifluoromethyl)-3-pyridinecarboxylate (Compound 43);

2-(Difluoromethyl)-5-hydroxymethyl-4-phenyl-6-(trifluoromethyl)-3-{[4-(trifluoromethyl)phenyl]hydroxymethyl}pyridine;

2-(Difluoromethyl)-5-hydroxymethyl-4-phenyl-6-(trifluoromethyl)-3-{[4-(trifluoromethyl)phenyl]carbonyl}pyridine;

2-(Difluoromethyl)-5-hydroxymethyl-4-(4-fluorophenyl)-6-(trifluoromethyl)-3-{[4-(trifluoromethyl)phenyl]hydroxymethyl}pyridine;

2-(Difluoromethyl)-5-hydroxymethyl-4-(4-fluorophenyl)-6-(trifluoromethyl)-3-{[4-(trifluoromethyl)phenyl]carbonyl}pyridine;

2-(Difluoromethyl)-5-hydroxymethyl-4-(4-fluorophenyl)-6-(trifluoromethyl)-3-{[4-(trifluoromethyl)phenyl]fluoromethyl}pyridine;

2-(Difluoromethyl)-5-hydroxymethyl-4-(4-fluorophenyl)-6-(trifluoromethyl)-3-([4-(trifluoromethyl)phenyl]fluoromethyl}pyridine;

2-(Difluoromethyl)-5-hydroxymethyl-4-(4-fluorophenyl)-6-(trifluoromethyl)-3-(2-naphthylfluoromethyl)pyridine;

2-(Difluoromethyl)-5-hydroxymethyl-4-(4-fluorophenyl)-6-(trifluoromethyl)-3-{[4-(trifluoromethyl)phenyl]mercaptomethyl}pyridine;

2-(Difluoromethyl)-5-hydroxymethyl-4-phenyl-6-(trifluoromethyl)-3-{[4-(trifluoromethyl)phenyl]mercaptomethyl}pyridine;

2-(Cyclopentyl)-5-hydroxymethyl-4-(4-fluorophenyl)-6-(trifluoromethyl)-3-{[4-(trifluoromethyl)phenyl]carbonyl)pyridine;

2-(1-Pyrrolidinyl)-5-hydroxymethyl-4-(4-fluorophenyl)-6-(trifluoromethyl)-3-{[4-(trifluoromethyl)phenyl]carbonyl}pyridine;

2-(1-Pyrrolidinyl)-5-hydroxymethyl-4-(4-fluorophenyl)-6-(trifluoromethyl)-3-{[4-(trifluoromethyl)phenyl]hydroxymethyl}pyridine; and 2-(1-Pyrrolidinyl)-5-hydroxymethyl-4-(4-fluorophenyl)-6-(trifluoromethyl)-3-{[4-(trifluoromethyl)phenyl]fluoromethyl)pyridine.

In yet another embodiment, the compound of Formula IA is Dimethyl 5,5'-dithiobis[2-difluoromethyl)-4-(2-methylpropyl)-6-(trifluoromethyl)-3-pyridinecarboxylate].

In another embodiment, the novel compounds comprise a compound of Formula IIB:

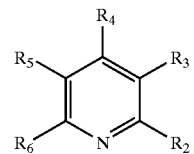

(IIB)

wherein:

$R_2$ and $R_6$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of $R_2$ and $R_6$ is fluorinated alkyl, chlorofluorinated alkyl or alkoxyalkyl;

$R_3$ is selected from the group consisting of arylcarbonyl, heteroarylcarbonyl, hydroxymethyl, arylalkoxyalkyl, trialkylsilyloxyalkyl,

—CHO,

—CO$_2$R$_7$, wherein $R_7$ is selected from the group consisting of hydrogen and alkyl; and

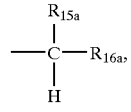

wherein $R_{15a}$ is selected from the group consisting of hydroxy, halogen, alkylthio and alkoxy, and $R_{16a}$ is selected from the group consisting of alkyl, haloalkyl, alkenyl, aryl and heteroaryl;

$R_4$ is selected from the group consisting of hydrogen, hydroxy, alkyl, cycloalkyl, cycloalkylalkyl, heteroarylalkyl, alkoxy, thio, trialkylsilyl, alkylamino, and —OC(O)N(R$_8$)$_2$, wherein $R_8$ is aryl;

$R_5$ is selected from the group consisting of hydrogen, alkyl, haloalkyl, alkenyl, haloalkenyl, alkynyl, haloalkynyl, aralkyl, alkoxy, aryloxy, cycloalkylthioalkyl, arylthioalkyl, heteroarylthioalkyl, alkoxyalkenyl, arylcarbonyloxyalkyl, pyrrolyl, substituted pyrrolidinyl, hydroxymethyl, arylalkoxyalkyl, and trialkylsilyloxyalkyl,

wherein $R_{14}$ is alkyl;

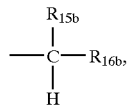

wherein $R_{15b}$ is selected from the group consisting of hydroxy, halogen, alkoxy, and alkylthio, aroyloxy, and alkylsulfonyloxy, and $R_{16b}$ is selected from the group consisting of alkyl, alkenyl, aryl, and heteroaryl;

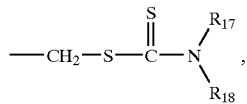

wherein $R_{17}$ and $R_{18}$ are independently alkyl;

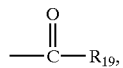

wherein $R_{19}$ is aryl, heteroaryl, —$SR_{20}$, and —$OR_{21}$, wherein $R_{20}$ is selected from the group consisting of aryl, heteroaryl and aminoalkyl, and $R_{21}$ is selected from the group consisting of aryl and heteroaryl;

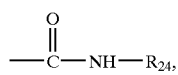

wherein $R_{24}$ is aralkyl;

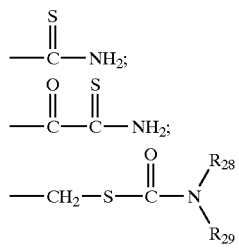

wherein $R_{28}$ and $R_{29}$ are independently alkyl;

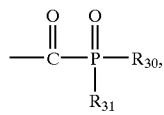

wherein $R_{30}$ and $R_{31}$ are independently alkoxy;

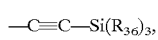

wherein $R_{36}$ is alkyl;

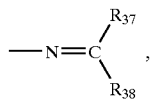

wherein $R_{37}$ is selected from the group consisting of hydrogen, alkoxy, and alkylthio, and $R_{38}$ is selected from the group consisting of haloalkyl, cycloalkyl, heterocyclylalkoxy, and alkylthio;

provided that when $R_{37}$ is hydrogen, then $R_{38}$ is selected from the group consisting of haloalkyl, cycloalkyl, and heterocyclylalkoxy;

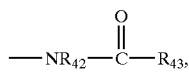

wherein $R_{42}$ is selected from the group consisting of hydrogen and alkyl, and $R_{43}$ is substituted heteroaryl;

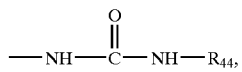

wherein $R_{44}$ is selected from the group consisting of aryl and heteroaryl;

wherein $R_{45}$ is selected from the group consisting of haloalkyl, heterocyclyl, alkylthioalkyl, aminocarbonylalkyl, —$SR_{46}$, and —$CH_2R_{47}$, wherein $R_{46}$ is selected from the group consisting of aryl and heteroaryl, and $R_{47}$ is selected from the group consisting of methylenedioxyphenyl, pyridyl, quinolinyl, tetrahydronaphthyl and benzodioxanyl;

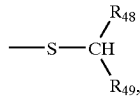

wherein $R_{48}$ is selected from the group consisting of hydrogen and alkyl, and $R_{49}$ is selected from the group consisting of alkoxy and haloalkyl;

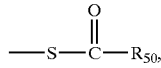

wherein $R_{50}$ is selected from the group consisting of alkyl, alkoxy, and heteroaryl; and

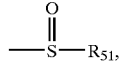

wherein $R_{51}$ is haloalkyl;

or a pharmaceutically acceptable salt or tautomer thereof, provided that:

when $R_2$ is selected from the group consisting of difluoromethyl and trifluoromethyl, $R_3$ is selected from the group consisting of —$CO_2H$, —$CO_2CH_3$ and —$CO_2C_2H_5$, $R_5$ is hydrogen, and $R_6$ is selected from the group consisting of hydrogen and trifluoromethyl, then $R_4$ is selected from the group consisting of cycloalkyl, cycloalkylalkyl, heteroarylalkyl, aralkenyl, alkoxy, thio, trialkylsilyl, alkylamino, and —$OC(O)N(R_8)_2$, wherein $R_8$ is aryl; provided further that when $R_2$, $R_3$ and $R_5$ are as defined above, and $R_4$ is alkoxy, then $R_6$ is hydrogen;

when $R_2$ is selected from the group consisting of fluorinated methyl and chlorofluorinated methyl, $R_3$ is selected from the group consisting of hydroxymethyl and $CO_2R_7$, $R_5$ is selected from the group consisting of hydroxymethyl and $CO_2R_{14}$, $R_6$ is selected from the group consisting of fluorinated methyl and chlorofluorinated methyl, and $R_7$ and $R_{14}$ are independently alkyl, then $R_4$ is selected from the group consisting of thio, trialkylsilyl, and —$OC(O)N(R_8)_2$, wherein $R_8$ is aryl;

when $R_2$ is difluoromethyl, $R_3$ is —$CO_2C_2H_5$, $R_4$ is hydrogen, $R_5$ is —$CO_2C_2H_5$, then $R_6$ is selected from the group consisting of hydrogen, monofluoroalkyl, difluoroalkyl and alkoxyalkyl;

when $R_2$ is trifluoromethyl, $R_3$ is —$CO_2R_7$, $R_5$ is methyl, $R_6$ is selected from the group consisting of fluorinated methyl, fluorinated ethyl and chlorofluorinated methyl, and $R_7$ is selected from the group consisting of hydrogen and alkyl, then $R_4$ is selected from the group consisting of hydrogen, alkyl, cycloalkyl, cycloalkylalkyl, heteroarylalkyl, thio, trialkylsilyl, and —$OC(O)N(R_8)_2$, wherein $R_8$ is aryl;

when $R_4$ is selected from the group consisting of alkyl, cycloalkyl and cycloalkylalkyl, $R_3$ is —$CO_2R_7$, and $R_7$ is alkyl, then $R_5$ is other than arylcarbonyl, heteroarylcarbonyl or

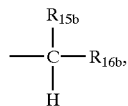

wherein $R_{16b}$ is alkyl when $R_{15b}$ is selected from the group consisting of hydroxy, halogen, alkylthio and alkoxy, or wherein $R_{16b}$ is aryl or heteroaryl when $R_{15b}$ is hydroxy;

when $R_4$ is selected from the group consisting of alkyl, cycloalkyl and cycloalkylalkyl, $R_5$ is —$CO_2R_{14}$, and $R_{14}$ is alkyl, then $R_3$ is other than arylcarbonyl, heteroarylcarbonyl or

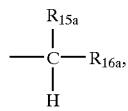

wherein $R_{16a}$ is alkyl when $R_{15a}$ is selected from the group consisting of hydroxy, halogen, alkylthio and alkoxy, or wherein $R_{16a}$ is aryl or heteroaryl when $R_{15a}$ is hydroxy; and when $R_2$ and $R_6$ are independently selected from fluorinated methyl and chlorofluorinated methyl, $R_3$ is $CO_2R_7$, $R_5$ is hydroxy, alkoxy or aryloxy, then $R_4$ is selected from the group consisting of aryl, cycloalkyl, cycloalkylalkyl, heteroarylalkyl, thio, trialkylsilyl, alkylamino, and —$OC(O)N(R_8)_2$, wherein $R_8$ is aryl; and when $R_4$ is aryl and one of $R_2$ and $R_6$ is trifluoromethyl, then the other of $R_2$ and $R_6$ is difluoromethyl.

Additional Compounds

Additional novel compounds that could be used in the methods and compositions of the present invention include, but are not limited to, the compounds:

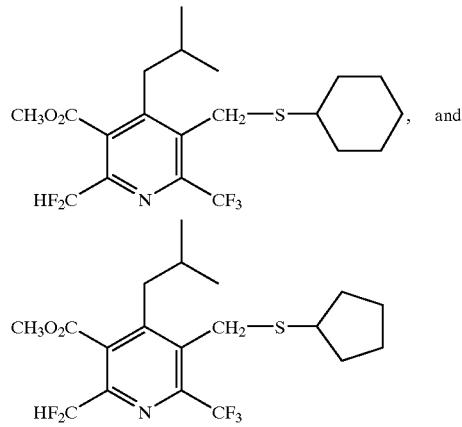

and those compounds listed in Tables 9, 10, 11 and 12 below. These compounds could be prepared by appropriate modification of the synthetic schemes previously referenced in this application.

TABLE 9

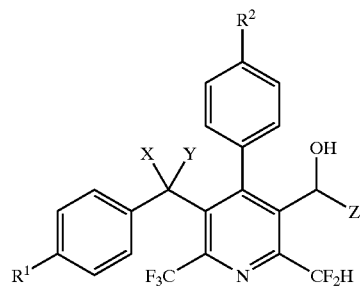

| $R^1$ | $R^2$ | X | Y | Z |
|---|---|---|---|---|
| Cl | H | H | OH | H |
| iPr | H | H | OH | H |
| F | H | H | OH | H |
| $CF_3$ | H | H | OH | H |
| Cl | H | O | O | H |
| iPr | H | O | O | H |
| F | H | O | O | H |
| $CF_3$ | H | O | O | H |
| Cl | H | F | H | H |
| iPr | H | F | H | H |
| F | H | F | H | H |
| $CF_3$ | H | F | H | H |
| Cl | H | H | OH | $CH_3$ |
| iPr | H | H | OH | $CH_3$ |
| F | H | H | OH | $CH_3$ |
| $CF_3$ | H | H | OH | $CH_3$ |
| Cl | H | O | O | $CH_3$ |
| iPr | H | O | O | $CH_3$ |
| F | H | O | O | $CH_3$ |
| $CF_3$ | H | O | O | $CH_3$ |
| Cl | H | F | H | $CH_3$ |
| iPr | H | F | H | $CH_3$ |
| F | H | F | H | $CH_3$ |
| $CF_3$ | H | F | H | $CH_3$ |
| Cl | H | H | OH | $C_2H_5$ |
| iPr | H | H | OH | $C_2H_5$ |
| F | H | H | OH | $C_2H_5$ |
| $CF_3$ | H | H | OH | $C_2H_5$ |
| Cl | H | O | O | $C_2H_5$ |

TABLE 9-continued

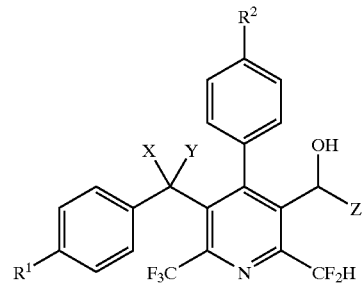

| R¹ | R² | X | Y | Z |
|---|---|---|---|---|
| iPr | H | O | O | C₂H₅ |
| F | H | O | O | C₂H₅ |
| CF₃ | H | O | O | C₂H₅ |
| Cl | H | F | H | C₂H₅ |
| iPr | H | F | H | C₂H₅ |
| F | H | F | H | C₂H₅ |
| CF₃ | H | F | H | C₂H₅ |
| Cl | H | H | OH | iBu |
| iPr | H | H | OH | iBu |
| F | H | H | OH | iBu |
| CF₃ | H | H | OH | iBu |
| Cl | H | O | O | iBu |
| iPr | H | O | O | iBu |
| F | H | O | O | iBu |
| CF₃ | H | O | O | iBu |
| Cl | H | F | H | iBu |
| iPr | H | F | H | iBu |
| F | H | F | H | iBu |
| CF₃ | H | F | H | iBu |
| Cl | H | H | OH | CF₃ |
| iPr | H | H | OH | CF₃ |
| F | H | H | OH | CF₃ |
| CF₃ | H | H | OH | CF₃ |
| Cl | H | O | O | CF₃ |
| iPr | H | O | O | CF₃ |
| F | H | O | O | CF₃ |
| CF₃ | H | O | O | CF₃ |
| Cl | H | F | H | CF₃ |
| iPr | H | F | H | CF₃ |
| F | H | F | H | CF₃ |
| CF₃ | H | F | H | CF₃ |

TABLE 10

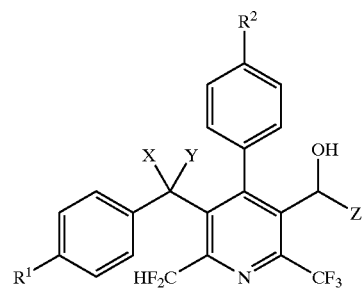

| R¹ | R² | X | Y | Z |
|---|---|---|---|---|
| Cl | H | H | OH | H |
| iPr | H | H | OH | H |
| F | H | H | OH | H |
| CF₃ | H | H | OH | H |
| Cl | H | O | O | H |
| iPr | H | O | O | H |
| F | H | O | O | H |
| CF₃ | H | O | O | H |
| Cl | H | F | H | H |

TABLE 10-continued

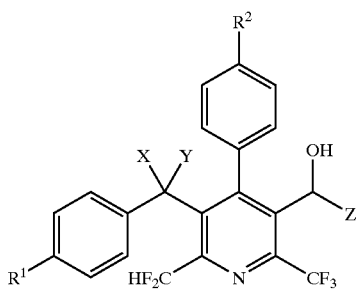

| R¹ | R² | X | Y | Z |
|---|---|---|---|---|
| iPr | H | F | H | H |
| F | H | F | H | H |
| CF₃ | H | F | H | H |
| Cl | H | H | OH | CH₃ |
| iPr | H | H | OH | CH₃ |
| F | H | H | OH | CH₃ |
| CF₃ | H | H | OH | CH₃ |
| Cl | H | O | O | CH₃ |
| iPr | H | O | O | CH₃ |
| F | H | O | O | CH₃ |
| CF₃ | H | O | O | CH₃ |
| Cl | H | F | H | CH₃ |
| iPr | H | F | H | CH₃ |
| F | H | F | H | CH₃ |
| CF₃ | H | F | H | CH₃ |
| Cl | H | H | OH | C₂H₅ |
| iPr | H | H | OH | C₂H₅ |
| F | H | H | OH | C₂H₅ |
| CF₃ | H | H | OH | C₂H₅ |
| Cl | H | O | O | C₂H₅ |
| iPr | H | O | O | C₂H₅ |
| F | H | O | O | C₂H₅ |
| CF₃ | H | O | O | C₂H₅ |
| Cl | H | F | H | C₂H₅ |
| iPr | H | F | H | C₂H₅ |
| F | H | F | H | C₂H₅ |
| CF₃ | H | F | H | C₂H₅ |
| Cl | H | H | OH | iBu |
| iPr | H | H | OH | iBu |
| F | H | H | OH | iBu |
| CF₃ | H | H | OH | iBu |
| Cl | H | O | O | iBu |
| iPr | H | O | O | iBu |
| F | H | O | O | iBu |
| CF₃ | H | O | O | iBu |
| Cl | H | F | H | iBu |
| iPr | H | F | H | iBu |
| F | H | F | H | iBu |
| CF₃ | H | F | H | iBu |
| Cl | H | H | OH | CF₃ |
| iPr | H | H | OH | CF₃ |
| F | H | H | OH | CF₃ |
| CF₃ | H | H | OH | CF₃ |
| Cl | H | O | O | CF₃ |
| iPr | H | O | O | CF₃ |
| F | H | O | O | CF₃ |
| CF₃ | H | O | O | CF₃ |
| Cl | H | F | H | CF₃ |
| iPr | H | F | H | CF₃ |
| F | H | F | H | CF₃ |
| CF₃ | H | F | H | CF₃ |

TABLE 11

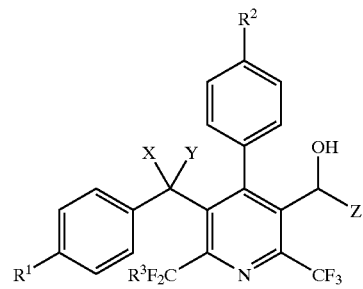

| R¹ | R² | X | Y | Z | R³ |
|---|---|---|---|---|---|
| Cl | H | H | OH | H | CH₃ |
| iPr | H | H | OH | H | CH₃ |
| F | H | H | OH | H | CH₃ |
| CF₃ | H | H | OH | H | CH₃ |
| Cl | H | O | O | H | CH₃ |
| iPr | H | O | O | H | CH₃ |
| F | H | O | O | H | CH₃ |
| CF₃ | H | O | O | H | CH₃ |
| Cl | H | F | H | H | CH₃ |
| iPr | H | F | H | H | CH₃ |
| F | H | F | H | H | CH₃ |
| CF₃ | H | F | H | H | CH₃ |
| Cl | H | H | OH | CH₃ | CH₃ |
| iPr | H | H | OH | CH₃ | CH₃ |
| F | H | H | OH | CH₃ | CH₃ |
| CF₃ | H | H | OH | CH₃ | CH₃ |
| Cl | H | O | O | CH₃ | CH₃ |
| iPr | H | O | O | CH₃ | CH₃ |
| F | H | O | O | CH₃ | CH₃ |
| CF₃ | H | O | O | CH₃ | CH₃ |
| Cl | H | F | H | CH₃ | CH₃ |
| iPr | H | F | H | CH₃ | CH₃ |
| F | H | F | H | CH₃ | CH₃ |
| CF₃ | H | F | H | CH₃ | CH₃ |
| Cl | H | H | OH | C₂H₅ | CH₃ |
| iPr | H | H | OH | C₂H₅ | CH₃ |
| F | H | H | OH | C₂H₅ | CH₃ |
| CF₃ | H | H | OH | C₂H₅ | CH₃ |
| Cl | H | O | O | C₂H₅ | CH₃ |
| iPr | H | O | O | C₂H₅ | CH₃ |
| F | H | O | O | C₂H₅ | CH₃ |
| CF₃ | H | O | O | C₂H₅ | CH₃ |
| Cl | H | F | H | C₂H₅ | CH₃ |
| iPr | H | F | H | C₂H₅ | CH₃ |
| F | H | F | H | C₂H₅ | CH₃ |
| CF₃ | H | F | H | C₂H₅ | CH₃ |
| iPr | H | H | OH | iBu | CH₃ |
| F | H | H | OH | iBu | CH₃ |
| CF₃ | H | H | OH | iBu | CH₃ |
| Cl | H | O | O | iBu | CH₃ |
| iPr | H | O | O | iBu | CH₃ |
| F | H | O | O | iBu | CH₃ |
| CF₃ | H | O | O | iBu | CH₃ |
| Cl | H | F | H | iBu | CH₃ |
| iPr | H | F | H | iBu | CH₃ |
| F | H | F | H | iBu | CH₃ |
| CF₃ | H | F | H | iBu | CH₃ |
| Cl | H | H | OH | CF₃ | CH₃ |
| iPr | H | H | OH | CF₃ | CH₃ |
| F | H | H | OH | CF₃ | CH₃ |
| CF₃ | H | H | OH | CF₃ | CH₃ |
| Cl | H | O | O | CF₃ | CH₃ |
| iPr | H | O | O | CF₃ | CH₃ |
| F | H | O | O | CF₃ | CH₃ |
| CF₃ | H | O | O | CF₃ | CH₃ |
| Cl | H | F | H | CF₃ | CH₃ |
| iPr | H | F | H | CF₃ | CH₃ |
| F | H | F | H | CF₃ | CH₃ |
| CF₃ | H | F | H | CF₃ | CH₃ |
| Cl | H | H | OH | H | Ph |
| iPr | H | H | OH | H | Ph |
| F | H | H | OH | H | Ph |

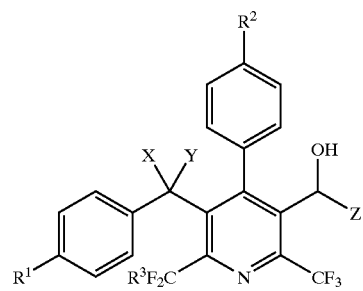

| R¹ | R² | X | Y | Z | R³ |
|---|---|---|---|---|---|
| CF₃ | H | H | OH | H | Ph |
| Cl | H | O | O | H | Ph |
| iPr | H | O | O | H | Ph |
| F | H | O | O | H | Ph |
| CF₃ | H | O | O | H | Ph |
| Cl | H | F | H | H | Ph |
| iPr | H | F | H | H | Ph |
| F | H | F | H | H | Ph |
| CF₃ | H | F | H | H | Ph |
| Cl | H | H | OH | CH₃ | Ph |
| iPr | H | H | OH | CH₃ | Ph |
| F | H | H | OH | CH₃ | Ph |
| CF₃ | H | H | OH | CH₃ | Ph |
| Cl | H | O | O | CH₃ | Ph |
| iPr | H | O | O | CH₃ | Ph |
| F | H | O | O | CH₃ | Ph |
| CF₃ | H | O | O | CH₃ | Ph |
| Cl | H | F | H | CH₃ | Ph |
| iPr | H | F | H | CH₃ | Ph |
| F | H | F | H | CH₃ | Ph |
| CF₃ | H | F | H | CH₃ | Ph |
| Cl | H | H | OH | C₂H₅ | Ph |
| iPr | H | H | OH | C₂H₅ | Ph |
| F | H | H | OH | C₂H₅ | Ph |
| CF₃ | H | H | OH | C₂H₅ | Ph |
| Cl | H | O | O | C₂H₅ | Ph |
| iPr | H | O | O | C₂H₅ | Ph |
| F | H | O | O | C₂H₅ | Ph |
| CF, | H | O | O | C₂H₅ | Ph |
| Cl | H | F | H | C₂H₅ | Ph |
| iPr | H | F | H | C₂H₅ | Ph |
| F | H | F | H | C₂H₅ | Ph |
| CF₃ | H | F | H | C₂H₅ | Ph |
| iPr | H | H | OH | iBu | Ph |
| F | H | H | OH | iBu | Ph |
| OF3 | H | H | OH | iBu | Ph |
| Cl | H | O | O | iBu | Ph |
| iPr | H | O | O | iBu | Ph |
| F | H | O | O | iBu | Ph |
| CF₃ | H | O | O | iBu | Ph |
| Cl | H | F | H | iBu | Ph |
| iPr | H | F | H | iBu | Ph |
| F | H | F | H | iBu | Ph |
| CF₃ | H | F | H | iBu | Ph |
| Cl | H | H | OH | H | CF₃ |
| iPr | H | H | OH | H | CF₃ |
| F | H | H | OH | H | CF₃ |
| CF₃ | H | H | OH | H | CF₃ |
| Cl | H | O | O | H | CF₃ |
| iPr | H | O | O | H | CF₃ |
| F | H | O | O | H | CF₃ |
| CF₃ | H | O | O | H | CF₃ |
| Cl | H | F | H | H | CF₃ |
| iPr | H | F | H | H | CF₃ |
| F | H | F | H | H | CF₃ |
| CF₃ | H | F | H | H | CF₃ |

TABLE 12

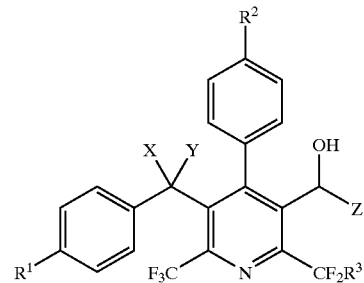

| R¹ | R² | X | Y | Z | R³ |
|---|---|---|---|---|---|
| Cl | H | H | OH | H | $CH_3$ |
| iPr | H | H | OH | H | $CH_3$ |
| F | H | H | OH | H | $CH_3$ |
| $CF_3$ | H | H | OH | H | $CH_3$ |
| Cl | H | O | O | H | $CH_3$ |
| iPr | H | O | O | H | $CH_3$ |
| F | H | O | O | H | $CH_3$ |
| $CF_3$ | H | O | O | H | $CH_3$ |
| Cl | H | F | H | H | $CH_3$ |
| iPr | H | F | H | H | $CH_3$ |
| F | H | F | H | H | $CH_3$ |
| $CF_3$ | H | F | H | H | $CH_3$ |
| Cl | H | H | OH | $CH_3$ | $CH_3$ |
| iPr | H | H | OH | $CH_3$ | $CH_3$ |
| F | H | H | OH | $CH_3$ | $CH_3$ |
| $CF_3$ | H | H | OH | $CH_3$ | $CH_3$ |
| Cl | H | O | O | $CH_3$ | $CH_3$ |
| iPr | H | O | O | $CH_3$ | $CH_3$ |
| F | H | O | O | $CH_3$ | $CH_3$ |
| $CF_3$ | H | O | O | $CH_3$ | $CH_3$ |
| Cl | H | F | H | $CH_3$ | $CH_3$ |
| iPr | H | F | H | $CH_3$ | $CH_3$ |
| F | H | F | H | $CH_3$ | $CH_3$ |
| $CF_3$ | H | F | H | $CH_3$ | $CH_3$ |
| Cl | H | H | OH | $C_2H_5$ | $CH_3$ |
| iPr | H | H | OH | $C_2H_5$ | $CH_3$ |
| F | H | H | OH | $C_2H_5$ | $CH_3$ |
| $CF_3$ | H | H | OH | $C_2H_5$ | $CH_3$ |
| Cl | H | O | O | $C_2H_5$ | $CH_3$ |
| iPr | H | O | O | $C_2H_5$ | $CH_3$ |
| F | H | O | O | $C_2H_5$ | $CH_3$ |
| $CF_3$ | H | O | O | $C_2H_5$ | $CH_3$ |
| Cl | H | F | H | $C_2H_5$ | $CH_3$ |
| iPr | H | F | H | $C_2H_5$ | $CH_3$ |
| F | H | F | H | $C_2H_5$ | $CH_3$ |
| $CF_3$ | H | F | H | $C_2H_5$ | $CH_3$ |
| iPr | H | H | OH | iBu | $CH_3$ |
| F | H | H | OH | iBu | $CH_3$ |
| $CF_3$ | H | H | OH | iBu | $CH_3$ |
| Cl | H | O | O | iBu | $CH_3$ |
| iPr | H | O | O | iBu | $CH_3$ |
| F | H | O | O | iBu | $CH_3$ |
| $CF_3$ | H | O | O | iBu | $CH_3$ |
| Cl | H | F | H | iBu | $CH_3$ |
| iPr | H | F | H | iBu | $CH_3$ |
| F | H | F | H | iBu | $CH_3$ |
| $CF_3$ | H | F | H | iBu | $CH_3$ |
| Cl | H | H | OH | $CF_3$ | $CH_3$ |
| iPr | H | H | OH | $CF_3$ | $CH_3$ |
| F | H | H | OH | $CF_3$ | $CH_3$ |
| $CF_3$ | H | H | OH | $CF_3$ | $CH_3$ |
| Cl | H | O | O | $CF_3$ | $CH_3$ |
| iPr | H | O | O | $CF_3$ | $CH_3$ |
| F | H | O | O | $CF_3$ | $CH_3$ |
| $CF_3$ | H | O | O | $CF_3$ | $CH_3$ |
| Cl | H | F | H | $CF_3$ | $CH_3$ |
| iPr | H | F | H | $CF_3$ | $CH_3$ |
| F | H | F | H | $CF_3$ | $CH_3$ |
| $CF_3$ | H | F | H | $CF_3$ | $CH_3$ |
| Cl | H | H | OH | H | Ph |
| iPr | H | H | OH | H | Ph |
| F | H | H | OH | H | Ph |
| $CF_3$ | H | H | OH | H | Ph |
| Cl | H | O | O | H | Ph |
| iPr | H | O | O | H | Ph |
| F | H | O | O | H | Ph |
| $CF_3$ | H | O | O | H | Ph |
| Cl | H | F | H | H | Ph |
| iPr | H | F | H | H | Ph |
| F | H | F | H | H | Ph |
| $CF_3$ | H | F | H | H | Ph |
| Cl | H | H | OH | $CH_3$ | Ph |
| iPr | H | H | OH | $CH_3$ | Ph |
| F | H | H | OH | $CH_3$ | Ph |
| $CF_3$ | H | H | OH | $CH_3$ | Ph |
| Cl | H | O | O | $CH_3$ | Ph |
| iPr | H | O | O | $CH_3$ | Ph |
| F | H | O | O | $CH_3$ | Ph |
| $CF_3$ | H | O | O | $CH_3$ | Ph |
| Cl | H | F | H | $CH_3$ | Ph |
| iPr | H | F | H | $CH_3$ | Ph |
| F | H | F | H | $CH_3$ | Ph |
| $CF_3$ | H | F | H | $CH_3$ | Ph |
| Cl | H | H | OH | $C_2H_5$ | Ph |
| iPr | H | H | OH | $C_2H_5$ | Ph |
| F | H | H | OH | $C_2H_5$ | Ph |
| $CF_3$ | H | H | OH | $C_2H_5$ | Ph |
| Cl | H | O | O | $C_2H_5$ | Ph |
| iPr | H | O | O | $C_2H_5$ | Ph |
| F | H | O | O | $C_2H_5$ | Ph |
| $CF_3$ | H | O | O | $C_2H_5$ | Ph |
| Cl | H | F | H | $C_2H_5$ | Ph |
| iPr | H | F | H | $C_2H_5$ | Ph |
| F | H | F | H | $C_2H_5$ | Ph |
| $CF_3$ | H | F | H | $C_2H_5$ | Ph |
| iPr | H | H | OH | iBu | Ph |
| F | H | H | OH | iBu | Ph |
| $CF_3$ | H | H | OH | iBu | Ph |
| Cl | H | O | O | iBu | Ph |
| iPr | H | O | O | iBu | Ph |
| F | H | O | O | iBu | Ph |
| $CF_3$ | H | O | O | iBu | Ph |
| Cl | H | F | H | iBu | Ph |
| iPr | H | F | H | iBu | Ph |
| F | H | F | H | iBu | Ph |
| $CF_3$ | H | F | H | iBu | Ph |
| Cl | H | H | OH | H | $CF_3$ |
| iPr | H | H | OH | H | $CF_3$ |
| F | H | H | OH | H | $CF_3$ |
| $CF_3$ | H | H | OH | H | $CF_3$ |
| Cl | H | O | O | H | $CF_3$ |
| iPr | H | O | O | H | $CF_3$ |
| F | H | O | O | H | $CF_3$ |
| $CF_3$ | H | O | O | H | $CF_3$ |
| Cl | H | F | H | H | $CF_3$ |
| iPr | H | F | H | H | $CF_3$ |
| F | H | F | H | H | $CF_3$ |
| $CF_3$ | H | F | H | H | $CF_3$ |

Pharmaceutical Compositions

Also embraced within this invention is a class of pharmaceutical compositions comprising the active compounds of Formulae I, IA, IB and/or Formulae IIA or IIB in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and compositions may, for example, be administered orally, intravascularly, intraperitoneally, subcutaneously, intramuscularly or topically.

The phrase "co-therapy" (or combination-therapy), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. The compounds of the invention can be administered as the sole active pharmaceutical agent, they can also be used in co-therapy with one or more cardiovascular agents, such as compounds that lower serum cholesterol concentrations including inhibitors of cholesterol biosynthesis such as HMG-CoA reductase inhibitors such as the statins (atorvastatin, cerivastatin, pravastatin, simvastatin, fluvastatin and lovastatin), inhibitors of squalene synthase, oxido squalene cyclase or inhibitors of other enzymes involved with cholesterol biosynthesis; inhibitors of the ileal bile acid transport protein (IBAT), cholesterol absorption antagonists, ACAT inhibitors, bile acid sequestrants such as Cholestyramine and Cholestagel, fibrates such as Gemfibrozil, niacins such as Niaspan, and omega-3 fatty acids such as Omacor. Compounds of the present invention can also be used in co-therapy with cardiovascular drugs that reduce hypertension such as Enalopril and Captopril, or with anti-diabetes drugs such as troglitazone, or with antithrombotic agents such as aspirin, warfarin, and glycoprotein IIbIIIa antagonists such as Reopro, Xemilofiban and Orbofiban. The compounds of this invention can also be used in co-therapy with agents which lower serum triglyceride concentrations, including inhibitors of cholesterol biosynthesis such as HMG-CoA reductase inhibitors such as the statins (atorvastatin), fibrates such as Gemfibrozil, niacins such as Niaspan, and omega-3 fatty acids such as Omacor.

The phrase "therapeutically-effective" is intended to qualify the amount of each agent which will achieve the goal of improvement in disease severity and the frequency of incidence over treatment of each agent by itself, while avoiding adverse side effects typically associated with alternative therapies.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. Patients undergoing treatment with the compounds and/or compositions disclosed herein can be routinely monitored by conventional methods to determine the effectiveness of therapy. Continuous analysis of the data obtained permits modification of the treatment regimen during treatment so that optimal amounts of the compounds and/or compositions of this invention are administered, and so that the duration of treatment can be determined as well. Thus, the treatment regimen/dosing schedule can be rationally modified over the course of treatment so as to achieve the lowest doses of each of the compounds and/or compositions of this invention which together result in satisfactory anti-lipidemic effectiveness, and so that administration of these compounds is continued only so long as is necessary to successfully treat the patient.

The pharmaceutical compositions may contain active ingredients in the range of about 0.1 to 2000 mg, and preferably in the range of about 0.5 to 500 mg. A daily dose of about 0.01 to 100 mg/kg body weight, and preferably between about 0.5 and about 20 mg/kg body weight, may be appropriate. The daily dose can be administered in one to four doses per day.

The compounds may be formulated in topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Additional Substituted Pyridines

The present invention further includes a group of substituted pyridines which exhibit percentage transfers in excess of 100% and are useful (i) in examining the structural requirements of the active site of the CTEP molecule, (ii) as control pyridines in the study of the mechanism for inhibiting the activity of CETP, and (ii) in the design of substituted pyridines which are effective CTEP inhibitors. Accordingly, they are useful in studying the prevention and treatment of dyslipidemia (hypoalphalipoproteinaemia), hyperlipoproteinaemia (chylomicronemia and hyperapobetalipoproteinaemia), peripheral vascular disease, hypercholesterolemia, atherosclerosis, coronary artery disease and other CETP-mediated disorders. These substituted pyridines include those compounds listed in Table 13 below:

TABLE 13

(T-8)

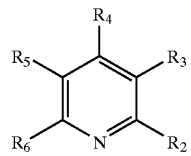

| CP | $R_2$ | $R_3$ | $R_4$ | $R_5$ | $R_6$ |
|---|---|---|---|---|---|
| 300 | $OCH_3$ | H | H | $CO_2H$ | H |
| 301 | $CF_2H$ | $CO_2CH_3$ | i-Bu | $NHC(O)CH_2Br$ | $CF_3$ |
| 302 | $CF_3$ | H | $CF_3$ | $CO_2C_2H_5$ | $CH_2CO_2C_2H_5$ |
| 303 | $CF_2H$ | $CO_2CH_3$ | i-Pr | $C(O)N(CH_3)OCH_3$ | $CF_3$ |
| 304 | $NH_2$ | $CO_2H$ | H | H | H |
| 305 | $CH_3$ | $CO_2C_2H_5$ | H | $CO_2C_2H_5$ | $CH_3$ |
| 306 | $CF_3$ | $CO_2C_2H_5$ | Et | CN | $CF_2H$ |
| 307 | $CF_3$ | $CO_2CH_3$ | O-i-Pr | S(O)Ph | $CF_3$ |
| 308 | $CH_2CO_2C_2H_5$ | $CO_2C_2H_5$ | H | H | H |
| 309 | $CF_3$ | $CO_2CH_3$ | OH | SPh | $CF_3$ |
| 310 | $CF_2C$ | $CO_2CH_3$ | 1-azyridinyl | $CO_2C_2H_5$ | $CF_3$ |
| 311 | $CF_3$ | $CO_2CH_3$ | OC(O)-(4-$CF_3$—Ph) | H | $CF_3$ |
| 312 | $CO_2H$ | H | H | H | $CO_2H$ |
| 313 | $CF_3$ | $CO_2CH_3$ | i-Bu | $CO_2CH_3$ | $CH_3$ |
| 314 | $CF_2H$ | $CO_2C_2H_5$ | H | $CO_2C_2H_5$ | $CF_3$ |
| 315 | $CF_3$ | $CO_2C_2H_5$ | $OCH_2CH=CH_2$ | H | $CF_3$ |
| 316 | $CF_2H$ | $CON(CH_3)_2$ | i-Bu | $CO_2CH_3$ | $CF_3$ |
| 317 | $CF_2H$ | $CO_2H$ | $CH=C(CH_3)_2$ | CN | $CF_3$ |
| 318 | $CF_3$ | $CO_2CH_3$ | OC(O)-Pr | H | $CF_3$ |
| 319 | $CF_3$ | $CO_2CH_3$ | O-(4-Cl—Ph) | H | $CF_3$ |
| 320 | $CF_2H$ | $CO_2CH_3$ | NH-i-Pr | C(O)-1-pyrazolyl | $CF_3$ |
| 321 | $CF_3$ | $CO_2C_2H_5$ | OH | $CH_3$ | H |
| 322 | $CH_3$ | $CO_2C_2H_5$ | H | $C(O)NHCH_2$-(4-Cl—Ph) | $CH_3$ |
| 323 | $CF_2H$ | $CO_2CH_3$ | Pr | $C(O)NH(CH_{21})_2Cl$ | $CF_3$ |
| 324 | $CF_3$ | $CO_2CH_3$ | OC(O)-t-Bu | H | $CF_3$ |

TABLE 13-continued (T-8)

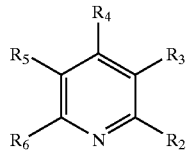

| CP | $R_2$ | $R_3$ | $R_4$ | $R_5$ | $R_6$ |
|---|---|---|---|---|---|
| 325 | $CF_2H$ | $CO_2H$ | $CH=C(CH_3)_2$ | $CO_2CH_3$ | $CF_3$ |
| 326 | $CF_2H$ | $CO_2CH_3$ | $N=S(CH_3)_2$ | $CO_2C_2H_5$ | $CF_3$ |
| 327 | OH | $CO_2H$ | H | H | $CH_3$ |
| 328 | $CF_2H$ | $CO_2CH_3$ | Pr | $C(O)N(CH_3)OCH_3$ | $CF_3$ |
| 329 | $CF_3$ | $CO_2C_2H_5$ | OH | H | H |
| 330 | $CF_2H$ | $CO_2CH_3$ | i-Bu | $NHC(O)CH_3$ | $CF_3$ |
| 331 | H | $CO_2CH_3$ | H | H | $OCH_3$ |
| 332 | $CF_3$ | $CO_2H$ | OH | $CH_3$ | $CF_3$ |
| 333 | $CF_2H$ | $CO_2CH_3$ | i-Bu | $C(O)NH(CH_2)_3OH$ | $CF_3$ |
| 334 | $CH_3$ | $CO_2CH_3$ | $CF_3$ | H | $CH_3$ |
| 335 | $CF_3$ | $CO_2CH_3$ | $OCH_3$ | $NHCO_2CH_3$ | $CF_3$ |
| 336 | $CF_2H$ | $CO_2CH_3$ | $CH_2$-c-Pr | 2-oxazolinyl | $CF_3$ |
| 337 | $CF_3$ | $CO_2CH_3$ | O(CO)-(pentafluorophenyl) | H | $CF_3$ |
| 338 | $CF_2H$ | $CO_2CH_3$ | i-Bu | $C(SCH_3)=NCH_2Ph$ | $CF_3$ |
| 339 | $CH_3$ | $CO_2C_2H_5$ | O-i-Pr | $CO_2C_2H_5$ | $CH_3$ |
| 340 | $CF_2H$ | $CO_2H$ | $CH_2SCH_3$ | $CO_2C_2H_5$ | $CF_3$ |
| 342 | $CF_3$ | $CO_2CH_3$ | i-Bu | $CO_2CH_3$ | $CH(1\text{-morpholinyl})_2$ |
| 342 | $CF_2H$ | $CO_2CH_3$ | i-Pr | $C(O)NH(CH_2)_2OH$ | $CF_3$ |
| 343 | $CF_2H$ | $CONHCH_3$ | i-Pr | $CO_2C_2H_5$ | $CF_3$ |
| 344 | $CF_2H$ | $CO_2CH_3$ | $CH_2S^+(CH_3)_2\ BF_4^-$ | $CO_2C_2H_5$ | $CF_3$ |
| 345 | $CF_3$ | $Si(CH_3)_3$ | $OCH_3$ | $CO_2CH_3$ | $CF_3$ |
| 346 | $CF_2H$ | $CO_2CH_3$ | i-Pr | $C(O)N(CH_3)_2$ | $CF_3$ |
| 347 | $CH_3$ | $CO_2CH_3$ | i-Bu | $CO_2CH_3$ | $CH_2Cl$ |
| 348 | $CH_3$ | $CO_2C_2H_5$ | $CO_2C_2H_5$ | $OS(O)_2$-(4-$CH_3Ph$) | $CH_3$ |
| 349 | $CF_3$ | $CO_2H$ | H | H | $CF_3$ |
| 350 | $CF_2H$ | $CO_2CH_3$ | i-Bu | H | $CF_3$ |

Definitions and Abbreviations

The use of generic terms and abbreviations in the description of the compounds are herein defined for clarity.

The term "alkyl", either alone or within other terms such as "haloalkyl", "cyanoalkyl" and "alkylthio", embraces substituted or unsubstituted linear or branched radicals having one to about 10 carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, and the like. The term "higher alkyl" denotes linear or branched radicals having eleven to about twenty carbon atoms. Examples of such radicals include undecyl, dodecyl, tridecyl, tetradecyl, and pentadecyl.

The term "alkenyl", either alone or within other terms such as "haloalkenyl" and "alkenylthio", embraces substituted or unsubstituted linear or branched radicals having one to about 10 carbon atoms and having one or more double bonds. More preferred alkenyl radicals are "lower alkenyl" radicals having one to about six carbon atoms. Examples of such radicals include ethenyl, propenyl, isopropenyl, butenyl, isobutenyl, hexenyl, and the like. The term "higher alkenyl" denotes linear or branched radicals having from 11 to about 20 carbon atoms and having one or more double bonds. Examples of such radicals include undecenyl, dodecenyl, tridecenyl, tetradecenyl, and pentadecenyl. Preferably, the unsaturation is remote from the moiety attaching the alkenyl group to the pyridine ring.

The term "alkynyl", either alone or within other terms such as "haloalkynyl" and "alkynylthio", embraces substituted or unsubstituted linear or branched radicals having one to about 10 carbon atoms and having one or more triple bonds. More preferred alkynyl radicals are "lower alkynyl" radicals having one to about six carbon atoms. Examples of such radicals include ethynyl, propynyl, butynyl, isobutynyl, hexynyl, and the like. The term "higher alkynyl" denotes linear or branched radicals having from 11 to about 20 carbon atoms having one or more triple bonds. Examples of such radicals include undecynyl, dodecynyl, tridecynyl, tetradecynyl, and pentadecynyl. Preferably, the unsaturation is remote from the moiety attaching the alkynyl group to the pyridine ring.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane, anthryl and biphenyl. Said "aryl" group can be substituted or unsubstituted.

The term "heterocyclyl" embraces saturated or partially saturated heteroatom-containing ring-shaped radicals, where the heteroatoms may be selected from nitrogen, sulfur and oxygen. Partially saturated heterocyclyl radicals have at least one double bond, but less than the maximum number of double bonds possible for the heterocyclyl ring. Examples of saturated heterocyclic radicals include saturated 3 to 6-membered heteromonocyclic groups containing 1 to 4 nitrogen atoms [e.g. azyrindinyl, pyrrolidinyl, imidazolidinyl, piperidino, piperazinyl, etc.]; saturated 3 to 6-membered heteromonocyclic groups containing 1 to 4 oxygen atoms [e.g. oxiranyl, oxolanyl, dioxolanyl, dioxanyl, etc.]; saturated 3 to 6-membered heteromonocyclic groups containing 1 to 4 sulfur atoms [e.g. thiolanyl, dithiolanyl, dithianyl, etc.]; saturated 3 to 6-membered heteromonocyclic groups containing 1 to 2 oxygen atoms and 1 to 3 nitrogen atoms [e.g. oxazolidinyl, morpholinyl, etc.]; saturated 3 to 6-membered heteromonocyclic groups containing 1 to 2 sulfur atoms and 1 to 3 nitrogen atoms [e.g., thiazolidinyl, etc.]; and saturated 3 to 6-membered heteromonocyclic groups containing 1 to 2 sulfur atoms and 1 to 3 oxygen atoms [e.g., oxathiolanyl, etc.]. Examples of partially saturated heterocyclyl radicals include imidazolinyl, oxazolinyl, isoxazolinyl, thiazolinyl, isothiazolinyl, dihydrothiophene, dihydropyran and dihydrofuran. Heterocyclic radicals also encompass unsaturated or partially saturated condensed heterocyclic radicals such as benzodioxanyl. Heterocyclyl radicals further can be unsubstituted or substituted with one or more groups including, for example, alkyl, halo, alkoxy, nitro, trifluoromethoxy, cycloalkyl, haloalkyl, alkylthio, alkylidene, acylamino, aryloxy, arylalkoxy, and oxo.

The term "heteroaryl" embraces unsaturated heteroatom-containing ring-shaped radicals, where the heteroatoms may be selected from nitrogen, sulfur and oxygen. Heteroaryl radicals have the maximum number of double bonds possible for the heterocyclyl ring. Examples of heteroaryl radicals include unsaturated 5 to 6 membered heteromonocyclyl groups containing 1 to 4 nitrogen atoms, for example, pyrrolyl, imidazolyl, pyrazolyl, 2-pyridyl, 3-pyridyl, 4-pyridyl, pyrimidyl, triazolyl, tetrazolyl, etc.; unsaturated condensed heterocyclic groups containing 1 to 5 nitrogen atoms, for example, indolyl, isoindolyl, benzimidazolyl, quinolyl, isoquinolyl, indazolyl and benzotriazolyl, etc.; unsaturated 3 to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl and isoxazolyl, etc.; unsaturated condensed heterocyclic groups containing 1 to 2 oxygen atoms and 1 to 3 nitrogen atoms [e.g. benzoxazolyl, benzoxadiazolyl, etc.]; unsaturated 5 to 6-membered heteromonocyclic groups containing 1 to 2 sulfur atoms and 1 to 3 nitrogen atoms, for example, thiazolyl, isothiazolyl, thiadiazolyl [e.g., 1,2,4- thiadiazolyl, 1,3,4-thiadiazolyl, 1,2,5-thiadiazolyl, etc.] etc.; unsaturated condensed heterocyclic groups containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said "heterocyclyl" group may have 1 to 3 substituents such as, for example, lower alkyl, lower alkoxy, halo, hydroxy, oxo, amino and lower alkylamino. Preferred heterocyclic radicals include five to ten membered fused or unfused radicals. More preferred examples of heteroaryl radicals include pyridyl, thienyl, thiazolyl, oxazolyl, furyl, and pyrazinyl. Heteroaryl can be unsubstituted or substituted with one or more groups selected from, for example, alkyl, halo, alkoxy, nitro, trifluoro-methoxy, cycloalkyl, haloalkyl, alkylthio, alkylidene, acylamino, aryloxy, arylalkoxy, and oxo.

The term "cycloalkyl" embraces substituted or unsubstituted radicals having three to ten carbon atoms. More preferred cycloalkyl radicals are "lower cycloalkyl" radicals having three to seven carbon atoms. Examples include radicals such as cyclopropyl, cyclobutyl, cyclopentyl, cyclohexyl and cycloheptyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Examples of such radicals include cyclopropylmethyl and cyclohexylhexyl. Also preferred cycloalkylalkyl radicals are "higher cycloalkylalkyl" radicals having cycloalkyl radicals attached to alkyl radicals having seven to fifteen carbon atoms. Examples of such radicals include cyclohexyldodecyl.

The term "cycloalkenyl" embraces radicals having three to ten carbon atoms and one or more carbon-carbon double bonds. More preferred cycloalkenyl radicals are "lower cycloalkenyl" radicals having three to seven carbon atoms. Examples include radicals such as cyclobutenyl, cyclopentenyl, cyclohexenyl and cycloheptenyl. Said "aryl" group may have 1 to 3 substituents such as, for example, lower alkyl, alkoxy, halo, hydroxy, oxo, amino and lower alkylamino.

The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. Also preferred aralkyl radicals are "higher aralkyl" radicals having aryl radicals attached to alkyl radicals having seven to fifteen carbon atoms. Examples of such radicals include phenyloctyl and phenylundecyl. The aryl in said aralkyl may be additionally substituted with, for example, halo, alkyl, alkoxy, halkoalkyl and haloalkoxy. The terms benzyl and phenylmethyl are used herein interchangeably.

The term "heteroaralkyl" embraces heteroaryl-substituted alkyl radicals. Preferable heteroaralkyl radicals are "lower heteroaralkyl" radicals having heteroaryl radicals attached to alkyl radicals having one to six carbon atoms. Examples of such radicals include —CH(OH)-2-furyl; —CH(OH)-2-thienyl; —CH(OCH$_3$)-2-thienyl; and —CH(OCH$_3$)-(5-isothiazolyl). Also preferred heteroaralkyl radicals are "higher heteroaralkyl" radicals having heteroaryl radicals attached to alkyl radicals having seven to fifteen carbon atoms. The heteroaryl in said heteroaralkyl may be additionally substituted with, for example, halo, alkyl, alkoxy, halkoalkyl and haloalkoxy.

The term "heterocyclylalkyl" embraces heterocyclyl-substituted alkyl radicals. Preferable heterocyclylalkyl radicals are "lower heterocyclylalkyl" radicals having heterocyclyl radicals attached to alkyl radicals having one to six carbon atoms. An examples of such radicals is —CH$_2$-(2-thiazolinyl). Also preferred heterocyclylalkyl radicals are "higher heterocyclylalkyl" radicals having heterocyclyl radicals attached to alkyl radicals having seven to fifteen carbon atoms. The heterocyclyl radical in said heterocyclylalkyl may be additionally substituted with, for example, halo, alkyl, alkoxy, halkoalkyl and haloalkoxy.

The term "aralkenyl" embraces aryl-substituted alkenyl radicals. Preferable aralkenyl radicals are "lower aralkenyl" radicals having aryl radicals attached to alkenyl radicals having one to six carbon atoms. Examples of such radicals include —CH=C(CH$_3$)Ph. Also preferred aralkenyl radicals are "higher aralkenyl" radicals having aryl radicals attached to alkenyl radicals having seven to fifteen carbon atoms. The aryl in said aralkenyl may be additionally substituted with, for example, halo, alkyl, alkoxy, halkoalkyl and haloalkoxy.

The term "alkoxy" embraces linear or branched oxy-containing radicals each having alkyl portions of one to about ten carbon atoms, such as methoxy radical. More preferred alkoxy radicals are "lower alkoxy" radicals having one to six carbon atoms. Examples of such radicals include methoxy, ethoxy, propoxy, iso-propoxy, butoxy and tert-butoxy. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "aryloxy" embraces aryl radicals, as defined above, attached to an oxygen atom. Examples of such radicals include phenoxy. The aryl in said aryloxy may be additionally substituted with halo, alkyl, alkoxy, halkoalkyl and haloalkoxy. The term "aralkoxy" embraces oxy-containing aralkyl radicals attached through an oxygen atom to other radicals. More preferred aralkoxy radicals are "lower aralkoxy" radicals having phenyl radicals attached to lower alkoxy radical as described above. The aryl in said aralkoxy radicals may be additionally substituted with, for example halo, alkyl, alkoxy, halkoalkyl and haloalkoxy.

The term "aryloxyalkyl" embraces aryloxy radicals, as defined above, attached to an alkyl group. Examples of such radicals include phenoxymethyl. The aryl in said aryloxy-alkyl may be additionally substituted with, for example, halo, alkyl, alkoxy, halkoalkyl and haloalkoxy.

The term "alkoxyalkyl" embraces alkoxy radicals, as defined above, attached to an alkyl group. Examples of such radicals include methoxymethyl. Also preferred alkoxyalkyl radicals are "higher alkoxyalkyl" radicals having seven to fifteen carbon atoms. An example of "higher alkoxyalkyl" is undecyloxymethyl.

The term "alkoxyalkenyl" embraces linear or branched alkenyl radicals having one or more alkoxy radicals attached to the alkenyl radical, that is, to form monoalkoxyalkenyl and dialkoxyalkenyl radicals. Preferred alkoxyalkenyl radicals are "lower alkoxyalkenyl" radicals having alkoxy radicals of six to fifteen carbon atoms. An examples of such radicals is —CH═CHOCH$_3$. The "alkenyl" and/or "alkoxy" radicals may be further substituted with one or more halo atoms, such as fluoro, chloro or bromo, to provide "haloalkenyl" and/or "haloalkoxy" radicals. Examples of such radicals include fluoromethoxy, chloromethoxy, trifluoromethoxy, trifluoroethoxy, fluoroethoxy and fluoropropoxy.

The term "aralkoxy" embraces alkoxy radicals having one or more aryl radicals attached to the alkoxy radical, that is, to form monoaralkoxy and diaralkoxy radicals. Preferred aralkoxy radicals are "lower aralkoxy" radicals having alkoxy radicals of one to ten carbon atoms. Examples of such radicals include phenylmethoxy. The "aryl" and "alkoxy" radicals may be further substituted with, for example, halogen, alkyl, haloalkyl, alkoxy, nitro, carboxy, carbalkoxy, alkylthio, alkylamino, dialkylamino, and amino. Examples of such radicals include, for example, methyl, chloro, trifluoromethyl, methoxy, —CO$_2$H, —CO$_2$C$_2$H$_5$, methylthio, methylamino and dimethylamino.

The term "heteroaralkoxy" embraces alkoxy radicals having one or more heteroaryl radicals attached to the alkoxy radical, that is, to form monoheteroaralkoxy and diheteroaralkoxy radicals. Preferred heteroaralkoxy radicals are "lower heteroaralkoxy" radicals having alkoxy radicals of one to ten carbon atoms. Examples of such radicals include oxaranylmethoxy and 2-pyridylmethoxy. The "heteroaryl" and "alkoxy" radicals may be further substituted with, for example, halogen, alkyl, haloalkyl, alkoxy, nitro, carboxy, carbalkoxy, alkylthio, alkylamino, dialkylamino, and amino. Examples of such radicals include, for example, methyl, chloro, trifluoromethyl, methoxy, —CO$_2$H, —CO$_2$C$_2$H$_5$, methylthio, methylamino and dimethylamino.

The term "carbonyl" embraces the —C(O)— radical found in such compounds as aldehydes and ketones.

The term "alkoxycarbonyl" embraces a carbonyl group, as defined above, having an attached alkoxy radical. Examples of such radicals include methoxycarbonyl and ethoxycarbonyl. The "alkoxy" radicals may be further substituted with, for example, halogen and cyano. Examples of such radicals include fluoroethoxycarbonyl and cyanomethoxycarbonyl.

The term "arylcarbonyloxy" embraces a carbonyl radical attached through an oxygen atom to other radicals and additionally having an aryl radical attached to the carbonyl group. More preferred arylcarbonyloxy radicals are "lower arylcarbonyloxy" radicals having phenyl radicals attached to the carbonyl radical as described above, such as benzoyloxy. The aryl in said arylcarbonyloxy radicals may be additionally substituted with, for example, halo, alkyl, alkoxy, halkoalkyl and haloalkoxy.

The term "arylcarbonyloxyalkyl" embraces an arylcarbonyloxy radical, as defined above, attached to attached an alkyl radical. More preferred arylcarbonyloxyalkyl radicals are "lower arylcarbonyloxyalkyl" radicals wherein the aryl portion of the arylcarbonyloxyalkyl radical comprises one or more phenyl radicals attached to the carbonyl as described above, such as benzoyloxymethyl. The aryl in said arylcarbonyloxy radicals may be additionally substituted with halo, alkyl, alkoxy, halkoalkyl and haloalkoxy.

The term "thio" embraces radicals containing a divalent sulfur. An example of a thio radical is the sulfhydryl (or —SH) radical.

The term "alkylthio" embraces radicals containing a linear or branched alkyl radical, of one to ten carbon atoms, attached to a divalent sulfur atom. More preferred alkylthio radicals are "lower alkylthio" radicals having one to six carbon atoms. Examples of "lower alkylthio" include methylthio (—S—CH$_3$) and ethylthio (—S—CH$_2$CH$_3$) Also preferred alkylthio radicals are "higher alkylthio" radicals having seven to fifteen carbon atoms. An example of "higher alkylthio" is dodecylthio.

The term "cycloalkylthio" embraces radicals containing a cyclic alkyl radical, of three to ten carbon atoms, attached to a divalent sulfur atom. More preferred cycloalkylthio radicals are "lower cycloalkylthio" radicals having three to six carbon atoms. An example of "lower cycloalkylthio" is cyclobutylthio. Also preferred cycloalkylthio radicals are "higher cycloalkylthio" radicals having seven to fifteen carbon atoms. An example of "higher cycloalkylthio" is cyclooctylthio.

The term "arylthio" embraces aryl radicals, as defined above, attached to an sulfur atom. Examples of such radicals include phenylthio. The aryl in said arylthio may be additionally substituted with, for example, halo, alkyl, alkoxy, halkoalkyl and haloalkoxy.

The term "heteroarylthio" embraces heteroaryl radicals, as defined above, attached to an sulfur atom. Examples of such radicals include pyridylthio. The heteroaryl in said heteroarylthio may be additionally substituted with, for example, halo, alkyl, alkoxy, halkoalkyl and haloalkoxy.

The term "alkylthioalkyl" embraces alkylthio radicals, as defined above, attached to an alkyl group. Examples of such radicals include methylthiomethyl and ethylthioethyl. Also preferred alkylthioalkyl radicals are "higher alkylthioalkyl"

radicals having seven to fifteen carbon atoms. An example of "higher alkylthioalkyl" is undecylthiomethyl.

The term "arylthioalkyl" embraces arylthio radicals, as defined above, attached to an alkyl group. Examples of such radicals include phenylthiomethyl. The aryl in said arylthioalkyl may be additionally substituted with halo, alkyl, alkoxy, halkoalkyl and haloalkoxy.

The term "heteroarylthioalkyl" embraces heteroarylthio radicals, as defined above, attached to an alkyl group. Examples of such radicals include pyrimidinylthiomethyl. The heteroaryl in said heteroarylthioalkyl may be additionally substituted with, for example, halo, alkyl, alkoxy, halkoalkyl and haloalkoxy.

The term "halo" or "halogen" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. More preferred haloalkyl radicals are "lower haloalkyl" radicals having one to about six carbon atoms. Examples of such haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "chlorinated methyl" means a methyl group having one or more chlorine atoms bonded thereto, including a alkyl radical wherein all the hydrogen atoms are replaced by chlorine. The term "fluorinated alkyl" means an alkyl group having one or more fluorine atoms bonded thereto, including a methyl radical wherein all the hydrogen atoms are replaced by fluorine. Fluorinated methyl is the preferred fluorinated alkyl. The term "chlorofluorinated methyl" means a methyl group having a chloro atom and one or two fluorine atoms bonded thereto, including a methyl radical wherein all the hydrogen atoms are replaced by a chlorine atom and two fluorine atoms.

The term "amido" or "aminocarbonyl" embraces amino radicals attached to a carbonyl radicals. The amino radical in said amido radical may be additionally substituted with, for example, halo, alkyl, alkoxy, halkoalkyl and haloalkoxy.

The term "alkylamino" embraces an alkyl radical, as defined above, attached to an amino group. Examples of such alkylamino radicals include methylamino and ethylamino. The alkyl radical in said alkylamino radical may be additionally substituted with, for example, halo, alkyl, alkoxy, halkoalkyl and haloalkoxy.

The term "trialkylsilyl" embraces silyl radicals trisubstituted with alkyl radicals. Examples of such trialkylsilyl radicals include trimethylsilyl and triethylsilyl. The alkyl radical in said trialkylsilyl radical may be additionally substituted with, for example, halo, alkyl, alkoxy, halkoalkyl and haloalkoxy.

The terms "cis" and "trans" denote a form of geometric isomerism in which two carbon atoms connected by a double bond will each have a hydrogen atom on the same side of the double bond ("cis") or on opposite sides of the double bond ("trans").

In addition to those substitutions described above, the substituents of the substituted alkyl, alkenyl, alkynyl, aryl, and heteroaryl groups and other moieties described above include, but are not limited to, alkyl, alkenyl, alkynyl, aryl, heteroaryl, nitrogen, oxygen, sulfur, haloalkyl such as trifluoromethyl, lower alkoxy such as methoxy, ethoxy or butoxy, lower haloalkoxy, hydroxy, halogen such as chloro or fluoro, nitro, amino, and keto.

As used herein, "Ph" means phenyl; "Me" means methyl"; "Et" means ethyl; "Ethylidine" means the group $CH_3CH=$; "R" means alkyl unless otherwise defined; "Pr" means propyl; "i-Pr" means iso-propyl; "i-propoxy" means isopropoxy; "c-Pr" means cyclopropyl; "Bu" means butyl; "i-Bu" means iso-butyl; "t-Bu" means tert-butyl; "c-Bu" means cyclobutyl; "Hx" means hexyl; "c-$C_5H_9$" means cyclopentyl; "c-Hx" means cyclohexyl; "B" means boron; "Br" means bromine; "C" means carbon; "Cl" means chlorine; "F" means fluorine; "H" means hydrogen; "I" means iodine; "N" means nitrogen; "O" means oxygen; "P" means phosphorus; "S" means sulfur; "Si" means silicon; and "TBS" means dimethyl-tert-butyl-silyl.

Preparation of Substituted Pyridines

A number of the substituted pyridine compounds and intermediates having pharmacological activity were previously known as herbicides. Accordingly, the specific and/or general procedures for preparing such known compounds can be found in U.S. Pat. Nos. 4,609,399, 4,655,816; 4,692,184; 4,698,093; 4,789,395; 4,885,026; 4,936,905; 4,988,384; 5,037,469; 5,125,961; 5,129,943; 5,156,670; 5,169,432; and 5,260,262; and in *Chem. Pharm. Bull.,* 14, 918 (1966); *Biokhimya,* 33, 350 (1968); *J. Agric Chem.,* 39, 2072 (1991); *Ann.,* 246, 32 (1888); *Res. Discl.,* 295, 867 (1988); and *J. Heterocyclic Chem.,* 26, 1771 (1989). These references are incorporated herein by reference.

The "Procedure Reference" column of Tables 1–2 provides exemplary references disclosing the specific procedures for the preparation of many of the substituted pyridines identified in those Tables. These references are incorporated herein by reference. One skilled in the art can prepare these compounds based on the disclosure of the references. A reference to "See Example _____" indicates that the procedure, while not specifically for the preparation of the compound listed in the Table, is sufficiently analogous that one skilled in the art can prepare the compound by making the necessary modifications to the referenced procedure without undue experimentation. Additional information for the preparation of a number of these compounds also is set forth below. A written description of the procedures for preparing the remaining substituted pyridines for which no corresponding reference appears in the Tables is set forth below.

The 2,6-dimethyl- and 2,6-bis(methoxymethyl)-3,5-pyridinedicarboxylates (such as Compound 92 and Compound 106) can be prepared by the procedure described in *Ann.,* 246, 32 (1888) and *Ann.,* 241, 1 (1882).

The 5-mercapto analogs II (see, e.g., Example 2 below) can be prepared from the 5-bromo derivative I (which itself can be prepared as shown in U.S. Pat. No. 4,789,395) by reaction with lithium sulfide. The 5-mercapto analogs II can be converted to the disulfide III by oxidation or by reaction with a mixture of 2-fluoroethanol, methanesulfonyl chloride and triethylamine or by reaction with bromine in acetic acid. The 5-mercapto analogs can be reacted with alkyl halides and acyl halides to give the derivatives IV and V cited in this invention. Alternatively pyridyl methylchloride VI can be reacted with a thiol to give the sulfide VII (see, e.g., Example 22 below)

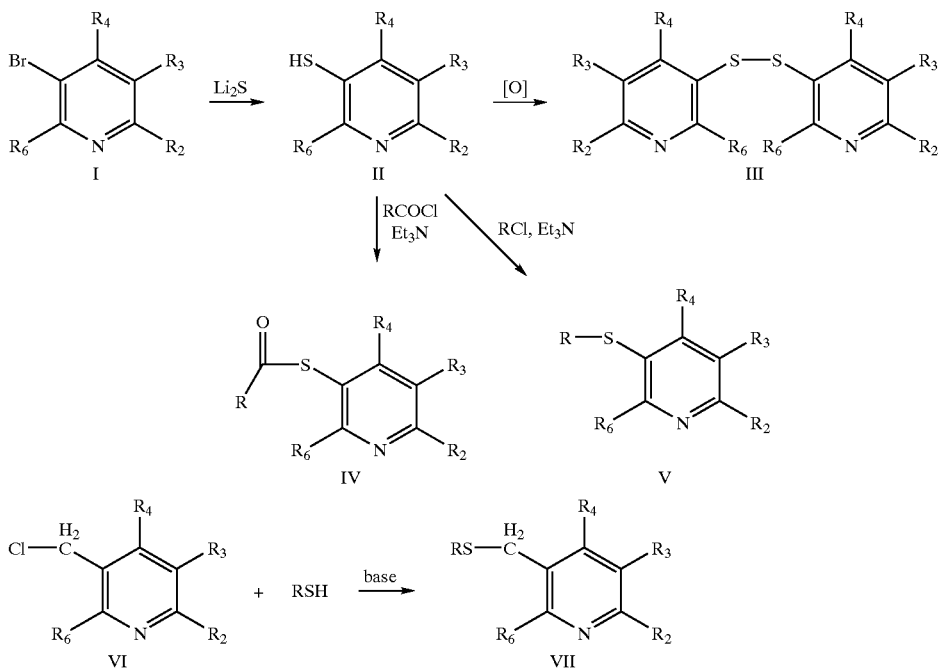

EXAMPLE 1

Preparation of Methyl 2-(Difluoromethyl)-5-mercapto-4-(2-methylpropyl)-6-(trifluoromethyl)-3-pyridinecarboxylate (Compound 7)

To a stirred solution of 10.11 g (0.026 mol) of methyl 5-bromo-2-(difluoromethyl)-4-(2-methylpropyl)-6-(trifluoromethyl)-3-pyridinecarboxylate (example 122 of U.S. Pat. No. 5,019,153) in 75 mL dry DMF was added 1.42 g (0.031 mol) of lithium sulfide in one portion and the mixture was stirred overnight at room temperature. The reaction mixture was diluted with 150 mL of 10% HCl solution and extracted with ether (3×100 mL). The combined extracts were washed with water, dried ($MgSO_4$) and evaporated. The residue was purified by kugelrohr distillation (oven temperature 100–110° C., 1.5 torr) to give 7.35 g (83%) of product as a yellow-green oil:

Anal. Calcd. for $C_{13}H_{14}F_5NO_2S$: C, 45.48; H, 4.11; N, 4.08 Found: C, 45.58; H, 4.14; N, 4.08.

EXAMPLE 2

Preparation of Dimethyl 5,5'-Dithiobis[2-(difluoromethyl)-4-(2-methylpropyl)-6-(trifluoromethyl)-3-pyridinecarboxylate] (Compound 181)

To a solution of 1.14 g (0.018 mol) of 2-fluoroethanol and 0.95 g (0.0094 mol) of triethylamine in 20 mL dry THF at −78° C. was added 1.07 g (0.0094 mol) of methanesulfonyl chloride in 10 mL of dry THF. After stirring the mixture for 30 min, 2.5 g (0.0073 mol) of product of example 1 and 0.95 g (0.0094 mol) of triethylamine were added. The mixture was slowly warmed to room temperature and stirred for an additional 2 h. The reaction mixture was evaporated, the residue was diluted with 100 mL of water and extracted with 125 mL of ether. The organic layer was washed with water, dried ($MgSO_4$) and evaporated. The residue was purified by preparative HPLC (8% ethyl acetate-hexane) to give 1.82 g (73%) of product as a yellow oil:

Anal. Calcd. for $C_{26}H_{26}F_{10}N_2O_4S_2$: C, 45.61; H, 3.83; N, 4.09 Found: C, 45.80; H, 3.87; N, 4.02

The same compound can be obtained by reacting compound 7 (see Table 1) with one half equivalent of bromine in acetic acid.

EXAMPLE 3

Preparation of Methyl 5-(4-t-Butylphenylthiomethyl)-2-(difluoromethyl)-4-(2-methylpropyl)-6-(trifluoromethyl)-3-pyridinecarboxylate (Compound 3)

Reaction of methyl 5-chloromethyl-2-(difluoromethyl)-4-(2-methylpropyl)-6-(trifluoromethyl)-3-pyridinecarboxylate (example 3 of U.S. Pat. No. 5,169,432) with 4-t-butylbenzenethiol according to the procedure of example 29 of U.S. Pat. No. 5,169,432 yielded the product as an oil.

Anal. Calcd. for $C_{18}H_{20}F_5NO_3$: C, 54.96; H, 5.13; N, 3.56. Found: C, 55.05; H, 5.13; N, 3.51.

EXAMPLE 4

Preparation of Ethyl 2,6-Bis(trifluoromethyl)-4-[4-(isopropylphenyl)thio]-5-methyl-3-pyridinecarboxylate (Compound 11)

Reaction of ethyl 2,6-bis(trifluoromethyl)-4-chloro-5-methyl-3-pyridinecarboxylate (example 65 of U.S. Pat. No. 4,655,816) with 4-isopropylbenzenethiol according to the procedure in example 23 of U.S. Pat. No. 4,655,816) yielded the desired product.

EXAMPLE 5

Preparation of Ethyl 2,6-Bis(trifluoromethyl)-4-(isopropoxy)-5-methyl-3-pyridinecarboxylate (Compound 53)

Example 37 of U.S. Pat. No. 4,655,816 discloses a procedure for the preparation of this compound.

EXAMPLE 6

Preparation of Methyl 2,6-bis(Trifluoromethyl)-4-(benzyloxy)-3-pyridinecarboxylate (Compound 37)

Example 9 of U.S. Pat. No. 4,655,816 discloses a procedure for the preparation of this compound.

EXAMPLE 7

Preparation of Methyl 2,6-Bis(trifluoromethyl)-5-(4,5-dihydro-2-thiazoly)-4-(2-methylpropyl)-3-pyridinecarboxylate (Compound 12)

Example 21 of U.S. Pat. No. 4,988,384 discloses a procedure for the preparation of this compound.

EXAMPLE 8

Preparation of Diethyl 2,6-Bis(trifluoromethyl)-4-(2-methylpropyl)-3,5-pyridinedicarboxylate (Compound 36)

Example 7 of U.S. Pat. No. 4,692,184 discloses a procedure for the preparation of this compound.

EXAMPLE 9

Preparation of Di-t-Butyl 2-(difluoromethyl)-4-(2-methylpropyl)-6-(trifluoromethyl)-3,5-pyridinedicarboxylate (Compound 9)

Reaction of the product of step 6 of U.S. Pat. No. 4,988,384 with excess t-butanol according to the procedure of example 56 of U.S. Pat. No. 4,692,184 yielded the product, mp 48–50° C.

EXAMPLE 10

Preparation of Methyl 2-(difluoromethyl)-5-(1-hydroxyl-furylmethyl)-4-(2-methylpropyl)-6-(trifluoromethyl)-3-pyridinecarboxylate (Compound 13)

Reaction of methyl 2-(difluoromethyl)-5-formyl-4-(2-methylpropyl)-6-(trifluoromethyl)-3-pyridinecarboxylate (compound B1 of U.S. Pat. No. 5,169,432) with 2-furyllithium according to the procedure in Example H of U.S. Pat. No. 5,260,262 yielded the product as an orange oil, $n_D^{25}$ 1.4863.

EXAMPLE 11

Preparation of Methyl 2-(Difluoromethyl)-4-(2-methylpropyl)-5-[(methoxycarbonyl)thio]-6-(trifluoromethyl)-3-pyridinecarboxylate (Compound 6)

To a stirred solution of 3.05 g (0.0089 mol) of product of example 1 and 0.094 g (0.01 mol) of methyl chloroformate in 25 mL dry THF was added 1.16 g (0.012 mol) of triethylamine dropwise at room temperature. After stirring for 30 min, the solvent was evaporated under reduced pressure. The residue was diluted with 100 mL of water and extracted with ether (3×50 mL). The combined organic layers were washed with water, dried (MgSO$_4$) and evaporated. Purification of the residue by preparative HPLC (5% ethyl acetate-hexane) gave 2.75 g (77%) of product as a yellow oil: $n_D^{25}$ 1.5830.

Anal. Calcd. for $C_{15}H_{16}F_5NO_4S$: C, 44.89; H, 4.02; N, 3.49 Found: C, 44.97; H, 4.04; N, 3.47

EXAMPLE 12

Preparation of Methyl 2-(Difluoromethyl)-5-[(i-propylthio)carbonyl]-4-(cyclobutyl)-6-(trifluoromethyl)-3-pyridinecarboxylate (Compound 14)

Methyl 5-chlorocarbonyl-4-cyclobutyl-2-(difluoromethyl)-6-(trifluoromethyl)-3-pyridinecarboxylate prepared similarly to the procedure in step 7 of U.S. Pat. No. 4,988,384 was reacted with 2-propanthiol according to the procedure in example 141 of U.S. Pat. No. 4,692,184 to give the product as an oil, $n_D^{25}$ 1.4946.

Anal. Calcd. for $C_{17}H_{18}F_5NO_3S$: C, 49.63; H, 4.41; N, 3.40; S, 7.79.

Found: C, 49.19; H, 4.59; N, 3.19; S, 7.40

EXAMPLE 13

Preparation of Methyl 2,6-Bis(trifluoromethyl)-4-(diphenylaminocarbonyloxy)-3-pyridinecarboxylate (Compound 25)

To a solution of 2 g (0.0069 mol) of methyl 2,6-bis(trifluoromethyl)-4-hydroxy-3-pyridinecarboxylate (example 4 of U.S. Pat. No. 4,655,816) in 20 mL of acetonitrile was added 0.7 g of triethylamine. A solution of 1.6 g (0.0069 mol) of diphenylcarbamyl chloride in 20 mL of acetonitrile was added to the above mixture and the resulting mixture was stirred at room temperature over the weekend. The precipitate formed was filtered off and the filtrate was concentrated in vacuo. The residue was slurried with ether. The insoluble material was filtered. The ether filtrate was concentrated and the residue was recrystallized from cyclohexane to give a white solid, mp 114–116° C.

Anal. Calcd. for $C_{22}H_{14}F_6N_2O_4$: C, 54.55; H, 2.91; N, 5.78. Found: C, 54.69; H, 3.05; N, 5.69.

EXAMPLE 14

Preparation of 3-Methyl 5-Ethyl 2-(Difluoromethyl)-4-mercapto-6-(trifluoromethyl)-3,5-pyridinedicarboxylate (Compound 2)

To a 5° C. solution of 6 g (0.017 mol) of 3-ethyl 5-methyl 6-(difluoromethyl)-4-chloro-2-(trifluoromethyl)-3,5-pyridinedicarboxylate (example 103 of U.S. Pat. No. 4,698,093) in 50 mL of dry THF was added 1.6 g (0.022 mol) of KSH. The resulting mixture was stirred at 0° C. for 15 min then at room temperature for 16 h. The mixture was poured into 5% NaOH and extracted with ether. The aqueous layer was made acidic with concentrated HCl and the product was extracted into ethyl acetate. The ethyl acetate layer was dried (MgSO$_4$) and solvent removed in vacuo affording 4.64 g of a light yellow oil. Purification by HPLC (10% MeOH/5% ethyl acetate/85% cyclohexane) gave 3.25 g of a yellow oil, $n_D^{25}$ 1.4775.

Anal. Calcd. for $C_{12}H_{10}F_5NO_4S$: C, 40.12; H, 2.81; N, 3.90; S, 8.92.

Found: C, 40.20; H, 2.79; N, 3.86; S, 8.90

EXAMPLE 15

Preparation of Diethyl 2-(Difluoromethyl)-4-(t-butylthio)-6-(trifluoromethyl)-3,5-pyridine-dicarboxylate (Compound 39)

Example 108 of U.S. Pat. No. 4,698,093 discloses a procedure for the preparation of this compound.

EXAMPLE 16

Preparation of Diethyl 2-(Difluoromethyl)-4-(cyclopentylthio)-6-(trifluoromethyl)-3,5-pyridinedicarboxylate (Compound 22)

Example 109 of U.S. Pat. No. 4,698,093 discloses a procedure for the preparation of this compound.

EXAMPLE 17

Preparation of Methyl 5-Chloromethyl-2-(difluoromethyl)-4-(2-methylpropyl)-6-(trifluoromethyl)-3-pyridinecarboxylate (Compound 83)

Example 3 of U.S. Pat. No. 5,169,432 discloses a procedure for the preparation of this compound.

EXAMPLE 18

Preparation of Methyl 2-(Difluoromethyl)-5-(1,3-dioxan-2-yl)-4-(2-methylpropyl)-6-(trifluoromethyl)-3-pyridinecarboxylate (Compound 59)

Example 109 of U.S. Pat. No. 4,988,384 discloses a procedure for the preparation of this compound.

EXAMPLE 19

Preparation of Methyl 2-(Difluoromethyl)-5-(methylthiomethyl)-4-(2-methylpropyl)-6-(trifluoromethyl)-3-pyridinecarboxylate (Compound 60)

Example 47 of U.S. Pat. No. 5,169,432 discloses a procedure for the preparation of this compound.

EXAMPLE 20

Preparation of Dimethyl 2-(Difluoromethyl)-4-{[(2-methylthio)pyrimidin-4-yl]methyl}-6-(trifluoromethyl)-3,5-pyridinedicarboxylate (Compound 67)

To a solution of 7.1 g (0.021 mol) of dimethyl 2-(difluoromethyl)-4-methyl-6-(trifluoromethyl)-3,5-pyridinedicarboxylate (example 218 of U.S. Pat. No. 4,692,184) in 90 mL of anhydrous THF cooled to −30° C. under nitrogen was added 25 mL (0.025 mol) of 1.0 M lithium bis(trimethylsilyl)amide in THF controlling the temperature range at −20° C. to −30° C. After 15 min at −30° C. a solution of 5.0 g (0.031 mol) of 4-chloro-2-methylthiopyrimidine in 20 mL of THF was added. The mixture is allowed to warm to −10° C., where it was held for 1.5 h. The reaction mixture was added to diluted HCl and worked up with methylene chloride. The product was purified by HPLC (12% ethyl acetate in hexane), and by recrystallization from hexane to give amber-yellow solid, mp 89–91° C.

Anal. Calcd. for $C_{17}H_{14}F_5N_3O_4S$: C, 45.24; H, 3.13; N, 9.31. Found: C, 45.27; H, 3.15; N, 9.26.

EXAMPLE 21

Preparation of Methyl 2-(Difluoromethyl)-4-(2-methylpropyl)-6-(trifluoromethyl)-5-[(trimethylsilyl)ethynyl]-3-pyridinedicarboxylate (Compound 19)

A mixture of 6 g (0.015 mol) of methyl 5-bromo-2-(difluoromethyl)-4-(2-methylpropyl)-6-(trifluoromethyl)-3-pyridinecarboxylate (example 122 of U.S. Pat. No. 5,019,153), 0.1 g of palladium (II) acetate, 0.2 g of triphenylphosphine, 30 ml of triethylamine and 5 g of (trimethylsilyl)acetylene was held at reflux under nitrogen for 4 hours and cooled to room temperature. The reaction mixture was filtered through a small plug of celite and the filtrate was concentrated in vacuo to give a dark oil. The residue was Kugelrohr distilled to give 5 g of light brown oil which was purified by Chromatotron (9:1 cyclohexane/methylene chloride). A total of 3 g (48% yield) of a yellow oil ($n_D^{25}$ 1.4681).

The 5-arylthiomethyl- and 5-heteroarylthiomethylpyridines shown in Table 6 can be prepared by reaction of an arylthiol or a heteroarylthiol with substituted 5-pyridylmethyl halide in the presence of base similar to the procedure in Example 3. The following procedures describe a typical synthesis of these compounds.

Scheme 1
Synthesis of Aryl Pyridylmethyl Sulfides X

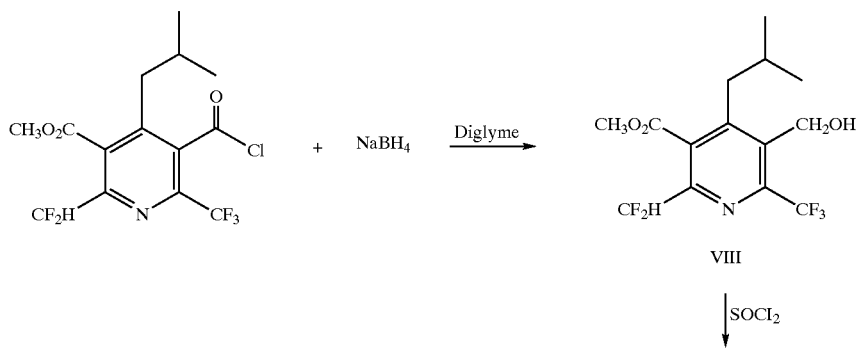

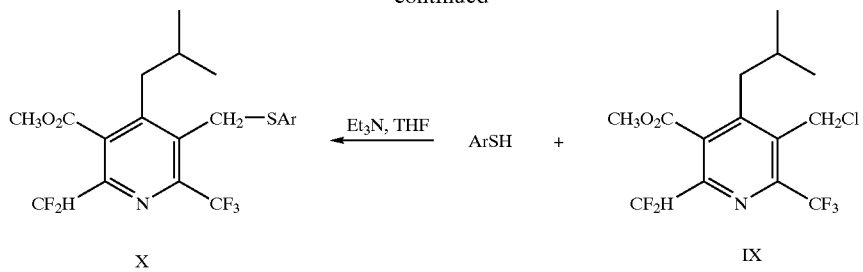

General Procedure for the Preparations of Sulfides X from IX.

To a solution of 1 mmol of triethylamine in 50 mL of THF was added 1 mmol of an arylthiol or a heteroarylthiol and 1 mmol of IX. The reaction mixture was stirred overnight and filtered to remove triethylamine hydrochloride. The filtrate was diluted with 50 mL of ether and washed with water. The ether layer was dried (MgSO$_4$) and concentrated in rotovap to give the product.

The 5-aryl- and heteroaryl-methylthiopyridines shown in Table 7 can be prepared by reaction of compound 7 with the appropriate arylmethyl chloride or heteroarylmethyl chloride.

Scheme 2
Synthesis of Arylmethyl Pyridyl Sulfides XI

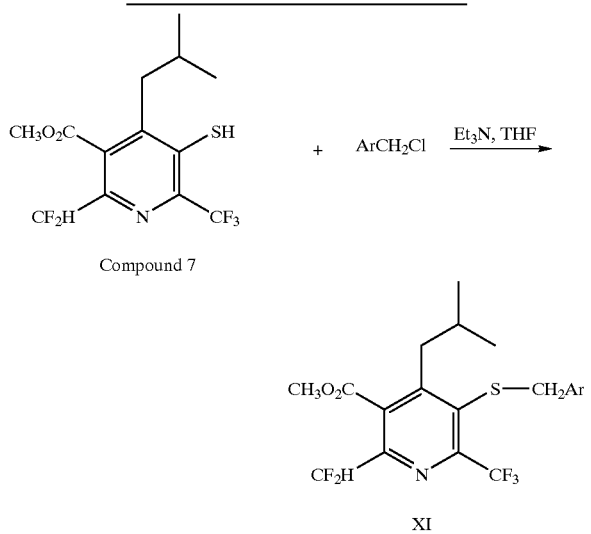

General Procedure for the Preparations of Sulfides XI

To a solution of 1 mmol of arylmethyl chloride and 1 mmol of methyl 2-(difluoromethyl)-4-isobutyl-5-mercapto-6-(trifluoromethyl)-3-pyridinecarboxylate (compound 7) in 50 mL of DMF was added 1 mmol of triethylamine. The reaction mixture was stirred until TLC showed that the reaction was mostly complete. The reaction mixture was diluted with ethyl acetate and washed successively with 1 N KHSO$_4$, water, 10% sodium hydroxide (to remove unreacted methyl 2-(difluoromethyl)-4-isobutyl-5-mercapto-6-(trifluoromethyl)-3-pyridinecarboxylate) and brine, dried (Na$_2$SO$_4$) and concentrated in rotovap. If necessary, the residue was purified by HPLC or chromatotron.

EXAMPLE 22

Preparation of Methyl 5-{[3-(Carbomethoxy)-2-(difluoromethyl)-4-isobutyl-6-(trifluoromethyl)-5-pyridyl]thiomethyl}-2-(difluoromethyl)-4-isobutyl-6-(trifluoromethyl)-3-pyridinecarboxylate (Compound 182)

To a solution of 550 mg (1.53 mmol) of 5-chloromethyl-2-(difluoromethyl)-4-(2-methylpropyl)-6-(trifluoromethyl)-3-pyridinecarboxylate (example 3 of U.S. Pat. No. 5,169,432) and 524 mg (1.53 mmol) of methyl 2-(difluoromethyl)-4-isobutyl-5-mercapto-6-(trifluoromethyl)-3-pyridinecarboxylate (compound 7) in 50 mL of DMF was added 154 mg (1.53 mmol) of triethylamine. The reaction mixture was stirred for 40 h, diluted with ethyl acetate (400 mL) and washed successively with 1 N KHSO$_4$ (200 mL) and brine (100 mL), dried (Na$_2$SO$_4$), and concentrated in a rotovap. The residue was purified by flash chromatography (10% EtOAc-hexane) to give 550 mg of material. TLC showed that this material contained product, compound 7 and disulfide of compound 181. A 110 mg of this material was further purified by HPLC (0–40% EtOAc-Hexane) to give pure product.

Reaction of compound 7 with the appropriate alkyl halide or acid chloride in THF in the presence of one equivalent of triethylamine with the procedure similar to Example 22 and Example 6 gave compounds 5, 33, 44, 145, 146, 147, and 183. Compound 148 was isolated as a byproduct from Example 2. The following example describes a typical procedure for the synthesis of these compounds.

EXAMPLE 23

Preparation of Methyl 2-(Difluoromethyl)-4-(2-methylpropyl)-5-(palmitoylthio)-6-(trifluoromethyl)-3-pyridinecarboxylate (Compound 5)

To a solution of 0.5 g of palmitoylchloride in 50 ml of THF was added 0.62 g of compound 7 followed by 0.37 g of triethylamine. The reaction mixture was stirred for 1 h, poured into water and extracted with ether. The ether extract was dried over MgSO$_4$ and concentrated in vacuo to give the product.

The compounds in Table 3 and Table 4 are prepared from reaction of methyl 5-chlorocarbonyl-2-(difluoromethyl)-4-(2-methylpropyl)-6-(trifluoromethyl)-3-pyridinecarboxylate (product of step 7 in U.S. Pat. No. 4,988,384) with appropriate the phenols and thiophenols. The following example describes a typical procedure for the synthesis of these compounds.

EXAMPLE 24

Preparation of Methyl 2-(Difluoromethyl)-5-{[(2,4-dimethyl-phenyl)thio]carbonyl}-4-(2-methylpropyl)-6-(trifluoromethyl)-3-pyridinecarboxylate (Compound 158)

To a solution of 1 g of 2,4-dimethylbenzenethiol and 3.29 g of methyl 5-chlorocarbonyl-2-(difluoromethyl)-4-2- methylpropyl)-6-(trifluoromethyl)-3-pyridinecarboxylate in 50 ml of THF was added 0.81 g of potassium t-butoxide. The reaction mixture was stirred for 1 h and poured into ice-water. The organic was extracted into methylene chloride. The methylene chloride extract was dried over $MgSO_4$ and concentrated in vacuo. The residue was recrystallized from ether-hexane to give 2.73 g of the product.

The unsymmetric aryl pyridyl disulfides can be prepared by oxidation of a mixture of the appropriate pyridinethiol and arylthiol with bromine in acetic acid followed by separation of the unsymmetric aryl pyridyl disulfide from the symmetric diaryl disulfide and dipyridyl disulfide by chromatography. The following example describes a typical procedure for the synthesis of these compounds.

EXAMPLE 25

Preparation of Methyl 5-(4-t-Butylphenyldithio)-2-(difluoromethyl)-4-(2-methylpropyl)-6-(trifluoromethyl)-3-pyridinecarboxylate (Compound 180)

To a mixture of 100 mg of compound 7 and 48.6 mg of 4-t-butylbenzenethiol in 5 ml of acetic acid was added 23 mg of bromine. The reaction mixture was stirred for 1 h, poured into water and extracted with ether. The ether extract was washed with saturated sodium bicarbonate, dried over $MgSO_4$ and concentrated in vacuo. The residue was purified by preparative TLC (9:1 Hexane: EtOAc) on silica gel to give the desired product.

EXAMPLE 26

Preparation of Dimethyl 2,6-Bis(trifluoromethyl)-4-(trimethylsilyl)-3,5-pyridinedicarboxylate (Compound 31)

To 10 ml of dry THF at −78° C. was added 8.4 ml (0.012 mol) of 1.55 M n-butyllithium in hexane followed by 1.21 g (1.7 ml, 0.012 mol) of diisopropylamine. After stirring at −78° C. for 30 min, a solution of 3.59 g (0.01 mol) of diethyl 2,6-bis(trifluoromethyl)-3,5-pyridine-dicarboxylate (prepared by the procedure similar to example 1 of U.S. Pat. No. 4,692,184) in 10 ml of dry THF was added. The reaction turned dark red and after stirring at −78° C. for 10 min, 4.4 g (0.05 mol) of chlorotrimethylsilane was added. The reaction was warmed to room temperature, stirred for 30 min and then was poured into 0° C. water, extracted with ether, dried ($MgSO_4$) and concentrated in vacuo. The residue was purified by HPLC (1:20 EtOAc:hexane) affording 2.09 g of the product as a light yellow oil which crystallized upon standing: mp 29–31° C.

EXAMPLE 27

Preparation of Diethyl 5,5'-(Carbonyldiimino)bis [6-(difluoromethyl)-4-ethyl-2-(trifluoromethyl)-3-pyridinecarboxylate (Compound 48)

A mixture of 2-(difluoromethyl)-5-ethoxycarbonyl-4-ethyl-(6-trifluoromethyl)-3-pyridinecarboxylic acid (example 28 of U.S. Pat. No. 4,692,184)and 40 ml of thionyl chloride was held at reflux for 1 h and concentrated in vacuo. The residue was dissolved in 50 ml of toluene and treated with 20 g of sodium azide and 0.1 g of 18-crown-6 (Aldrich). The reaction mixture was held at reflux for 24 h and filtered. The filtrate was treated with 50 ml of concentrated HCl and stirred for 18 h. The reaction mixture was treated with 50 ml of water and the toluene layer was separated and concentrated in vacuo. The residue was treated with 40 ml of trifluoroacetic acid and 10 ml of water then was held at reflux for 30 min and concentrated in vacuo. The residue was stirred with water and extracted with ether. The ether layer was washed with saturated sodium bicarbonate, dried ($MgSO_4$) and concentrated in vacuo to give 7.9 g of syrup. This syrup was stirred with ether and filtered to give 0.58 g of product, mp 219–221° C.

EXAMPLE 28

Preparation of Dimethyl 5,5'-Carbonylbis[4-(1-methylethoxy)-2-(trifluoromethyl)-3-pyridinecarboxylate (Compound 54)

Step 1: Methyl 4-Hydroxy-2-(trifluoromethyl)-3-pyridinecarboxylate.

A mixture of 105 g (0.5 mol) of methyl 2-acetyl-3-amino-4,4,4-trifluoro-2-butenoate (example 2 of U.S. Pat. No. 4,655,816), acetic anhydride (152 g), and trimethyl orthoformate (106 g) was held at reflux for 16 h then distilled to remove low boiling material (bp 65–90° C.). The remaining material was concentrated in vacuo and the residue was kugelrohr distilled at 2 torr (80–120° C.) to give 114 g of distillate. This distillate (44 g) was added dropwise to a mixture of 14.5 g of 60% sodium hydride oil dispersion in 100 ml of 1,2-dimethoxyethane (DME). The reaction mixture was maintained at 25–30° C. with an ice-water bath. The reaction mixture was stirred at room temperature for 18 h and poured into 300 ml of ice-water. The aqueous layer was extracted with ether and filtered. The aqueous layer was acidified with concentrated HCl. The oil precipitate was extracted into ether. The ether extract was extracted with 10% potassium carbonate. The potassium carbonate layer was acidified with concentrated HCl. The precipitate was filtered and air dried to give 20.4 g of the product, mp 78–82° C.

Step 2: Methyl 4-(1-Methylethoxy)-2-(trifluoromethyl)-3-pyridinecarboxylate (Compound 127).

A mixture of 7.0 g of product of step 1, 4.74 g of potassium carbonate, 14 g of 2-iodopropane and 50 ml of acetone was held at reflux for 18 h and concentrated in vacuo. The residue was treated with water and extracted with ether. The ether extract was dried ($MgSO_4$) and concentrated in vacuo. The residue was crystallized from hexane at low temperature to give 6.2 g of solid, mp 57.5–58.5° C.

Compound 121 in Table 1 was similarly prepared except using ethyl 2-acetyl-3-amino-4,4,4-trifluoro-butenoate (example 1 of U.S. Pat. No. 4,655,816) as the starting material in step 1.

Step 3: Dimethyl 5,5'-Carbonylbis[4-(1-methylethoxy)-2-(trifluoromethyl)-3-pyridinecarboxylate, Compound 54.

To a cold (−78° C.) solution of 20 ml dry DME was added 11.5 ml of 1.6 M butyllithium in hexane followed by 2.5 ml of diisopropylamine. The reaction mixture was stirred for 10 min. To the above solution was added a solution of 4.2 g of product of step 2 in 15 ml of dry DME. The reaction mixture turned orange. After 5 min stirring, 3.3 ml of ethyl chloroformate was added to the reaction mixture. After 10 min stirring, the reaction mixture was poured into water and extracted with ether. The ether extract was dried ($MgSO_4$) and concentrated in vacuo. The residue was purified by column chromatography on silica gel (20% EtOAc in hexane) to give 3.45 g of oil which was crystallized from hexane to give 2.2 g of solid, mp 74–75° C.

EXAMPLE 29

Preparation of Methyl 2-(Difluoromethyl)-4-cyclobutyl-5-(1-pyrrolyl)-6-(trifluoromethyl)-3-pyridinecarboxylate (Compound 70)

A solution of 1.62 g (5 mmol) of methyl 5-amino-2-(difluoromethyl)-4-cyclobutyl-6-(trifluoromethyl)-3- pyridinecarboxylate (example A-2 of U.S. Pat. No. 5,114,465) and 0.8 g (6 mmol) of 2,5-dimethoxytetrahydrofuran in 10 ml of acetic acid as heated at 70° C. for 2.5 h. The reaction mixture was then diluted with 100 ml of water and extracted with ethyl acetate. The combined organic layers were washed with saturated sodium bicarbonate (3×100ml), dried (MgSO$_4$) and concentrated in vacuo. The residue was purified by column chromatography on silica gel (10% EtOAc in hexane) to give the product, mp 70–71° C.

EXAMPLE 30

Preparation of Methyl 2-(Difluoromethyl)-4-(2-methylpropyl)-5-(aminothionocarbonyl)-6-(trifluoromethyl) -3-pyridinecarboxylate (Compound 77)

To 16.5 g of methyl 6-(difluoromethyl)-4-(2-methylpropyl)-5-(methoxycarbonyl)-2-(trifluoromethyl)-a-oxo-3-pyridineacetate (prepared by example E of U.S. Pat. No. 5,298,479) in 60 ml of methylene chloride was added 25 ml of concentrated ammonium hydroxide. The reaction mixture was stirred for 2 h and the aqueous layer was saturated with NaCl and the organic was extracted into methylene chloride. The methylene chloride layer was dried (MgSO$_4$) and concentrated in vacuo. The residue was recrystallized from 20% EtOAc-benzene to give 12.5 g of 6-(difluoromethyl) -4-(2-methylpropyl)-5-(methoxycarbonyl)-2-(trifluoromethyl)-a-oxo-3-pyridineacetamide. A mixture of 2.4 g of this material, 2.0 g of phosphorus pentasulfide, 2 g of Celite and 16 ml of toluene was held at reflux for 2h. The mixture was filtered and concentrated in vacuo. The residue was purified by column chromatography on silica gel (20% EtOAc in hexane) to give an oil which crystallized from 3% EtOAc in hexane as a solid.

EXAMPLE 31

Preparation of Methyl 2-(Difluoromethyl)-4-(2-methylpropyl)-5-[(tetrahydro-2-furyl)thio]-6-(trifluoromethyl)-3-pyridinecarboxylate (Compound 150)

A mixture of 7.07 g (0.021 mol) of compound 7, 2.92 g (0.042 mol) of dihydrofuran, and catalytic toluenesulfonic acid (9 mg) in 80 ml of ether was stirred overnight. The reaction mixture was concentrated in vacuo, and the residue was purified by HPLC (20% EtOAc in hexane) to give 5.82 g (68%) of the desired product as a yellow oil, n$^{25}$D 1.5803.

EXAMPLE 32

Preparation of Dimethyl 2,6-Bis(methoxymethyl)-4-propyl-3,5-pyridinedicarboxylate (Compound 92)

A solution of 4.93 g (0.068 mol) of n-butyraldehyde, 20 g (0.137 mol) of methyl 4-methoxyacetoacetate, 15 ml of ethanol, and 6.8 ml of concentrated ammonium hydroxide was held at reflux for 5 h and poured into 200 ml of ice water. The oil which precipitated out was extracted into ether. The ether layer was washed with water, dried (MgSO$_4$), and concentrated in vacuo. The residue was purified by HPLC (10% EtOAc in hexane) to give 7.91 g of yellow solid. Recrystallization from hexane gave 6.44 g of dimethyl 2,6-bis(methoxymethyl)-1,4-dihydro-4-propyl-3,5-pyridinedicarboxylate as yellow solid. A solution of this solid (4.35 g, 0.0133 mol) in 75 ml of 70% acetic acid was heated to 70° C. Chromium trioxide (3.99 g, 0.0399 mol) was added slowly. The reaction mixture was stirred at 65–70° C. for 1 h and poured into ice water and extracted with ether. The combined ether layers were stirred with 500 ml of saturated sodium bicarbonate. The ether layer was dried (MgSO$_4$) and concentrated in vacuo. The residue was kugelrohr distilled at 140° C. at 1 torr to give an oil, n$^{25}$D 1.4924.

EXAMPLE 33

Preparation of Methyl 5-[(Diethoxyphosphinyl) carbonyl]-2-(difluoromethyl)-4-(1-methylethylamino)-6-(trifluoromethyl)-3-pyridinecarboxylate (Compound 85)

A mixture of 46.27 g (0.1 mol) of 3-methyl 5-benzyl 2-(difluoromethyl)-4-(1-methylethylamino)-6-(trifluoromethyl)-3,5-pyridinedicarboxylate (example 181 of U.S. Pat. No. 4,698,093) in 1.2 L of a 1:5 mixture of THF in methanol was hydrogenated using catalytic 5% Pd/C under 50 lb of hydrogen pressure for 48 h. The reaction mixture was filtered through Celite and concentrated in vacuo to give 36 g of 3-methyl 5-hydrogen 2-(difluoromethyl)-4-(1-methylethylamino)-6-(trifluoromethyl)-3,5-pyridinedicarboxylate. To a mixture of 34.7 g of this monoacid in 400 ml of carbon tetrachloride was added 23 g (0.11 mol) of phosphorus pentachloride. The reaction mixture was stirred at room temperature until HCl evolution stopped. The reaction mixture was held at reflux for 20 min and concentrated in vacuo affording 38.04 g of monoacid chloride as a yellow oil. A portion (3.75 g 0.01 mol) of this oil and 1.7 g (0.01 mol) of triethyl phosphite was heated to 160° C. and then cooled. The resulting oil was purified by HPLC (25% EtOAc in hexane) affording 2.09 g of (44%) of product as a thick yellow oil.

EXAMPLE 34

Preparation of Methyl 2-(Difluoromethyl)-5-{[methoxy (methylthio)methylene]amino)-4-(2-methylpropyl)-6-(trifluoromethyl)-3-pyridinecarboxylate (Compound 27)

To a solution of 2.5 g (6.8 mmol) of methyl 2-(difluoromethyl)-5-isothiocyanato-4-(2-methylpropyl)-6-(trifluoromethyl)-3-pyridinecarboxylate (U.S. Pat. No. 5,129,943 example 41 step A) in 25 ml of anhydrous THF at room temperature was added 1.6 g (7.5 mmol) of 25% sodium methoxide in methanol. The reaction mixture was stirred for 30 min and was treated with 1.93 g (14 mmol) of methyl iodide. The reaction mixture was stirred for 3 h and concentrated in vacuo. The residue was partitioned with ether (75 ml) and 10% HCl (50 ml). The organic layer was washed with water (3×30 ml), dried (MgSO$_4$), and concentrated in vacuo. The crude product was purified by chromatotron (20% EtOAc in hexane) to afford 2.32 g (82%) of a colorless oil, n$^{25}$D 1.5982.

EXAMPLE 35

Preparation of Methyl 5-{[Bis(methylthio) methylene]amino}-2-(difluoromethyl)-4-(2-methylpropyl)-6-(trifluoromethyl)-3-pyridinecarboxylate (Compound 42)

This was prepared similar to example 33 except sodium methanethiolate was used instead of sodium methoxide. The product was isolated as a colorless oil, n$^{25}$D 1.5850.

EXAMPLE 36

Preparation of Methyl 2-(Difluoromethyl)-4-(2-methyl-propyl)-5-((oxiranylmethoxy)methylene] amino}-6-(trifluoromethyl)-3-pyridinecarboxylate (Compound 30)

A slurry of 10.0 g (0.028 mol)of methyl 2-(difluoromethyl)-5-formylamino-4-(2-methylpropyl)-6-

(trifluoromethyl)-3-pyridinecarboxylate (U.S. Pat. No. 5,037,469 example G1) and 6.03 g (0.029 mol) of phosphorus pentachloride in 75 ml of $CCl_4$ was stirred overnight at room temperature. The solvent was evaporated to give crude imidoyl chloride.

To a stirred solution of 6.02 g (0.0163 mol) of the crude imidoyl chloride in 75 ml of anhydrous THF at room temperature was added 6.43 g (0.087 mol) of glycidol in one portion followed by 2.53 g (0.021 mol) of 4-dimethylaminopyridine. The reaction mixture was held at reflux for 3 h and concentrated in vacuo. The residue was partitioned with ether (100 ml) and water (50 ml). The organic layer was washed with 10% HCl (3×30 ml) and saturated sodium bicarbonate (3×30 ml), dried ($MgSO_4$), and concentrated in vacuo. The crude product was purified by chromatotron (20W EtOAc in hexane) to afford 2.58 f (38%) of a solid, mp 41–43° C.

EXAMPLE 37

Preparation of Methyl 2-(Difluoromethyl)-5-(iodomethyl)-4-(2-methylpropyl)-6-(trifluoromethyl)-3-pyridinecarboxylate (Compound 32)

Reaction of methyl 2-(difluoromethyl)-5-(chloromethyl)-4-(2-methylpropyl)-6-(trifluoromethyl)-3-pyridinecarboxylate (U.S. Pat. No. 5,169,432 example 3) with sodium iodide in refluxing acetone according to the procedure known to those in the art yielded the product.

Compound 13 was prepared by the procedure in example H of U.S. Pat. No. 5,260,262. Compounds 89, 105, 131, and 133 were similarly prepared.

Compounds 34 and 40 were prepared from the 5-[(heteroaryl)hydroxymethyl] compounds which were prepared by the procedure H of U.S. Pat. No. 5,260,262. The following example described the preparations of these compounds.

EXAMPLE 38

Preparation of Methyl 2-(Difluoromethyl)-5-[(methoxy) isothiazol-5-ylmethyl]-4-(2-methylpropyl)-6-(trifluoromethyl)-3-pyridinecarboxylate (Compound 34)

Methyl 2-(difluoromethyl)-5-[(isothiazol-5-yl) hydroxymethyl]-4-(2-methylpropyl)-6-(trifluoromethyl)-3-pyridinecarboxylate (prepared by the procedure similar to example H of U.S. Pat. No. 5,260,262) was alkylated with methyl iodide by the procedure in example 61 of U.S. Pat. No. 5,169,432.

EXAMPLE 39

Methyl 5-(Benzoyloxymethyl)-2-(difluoromethyl)4-(cyclopropylmethyl)-6-(trifluoromethyl)-3-pyridinecarboxylate (Compound 41)

Reaction of methyl 2-(difluoromethyl)-5-(hydroxymethyl)-4-(cyclopropylmethyl)-6-(trifluoromethyl)-3-pyridinecarboxylate (U.S. Pat. No. 5,169,432 example A compound A4) with. Benzoyl chloride and triethylamine according to the procedure in example 99 of U.S. Pat. No. 5,169,432 gave the product.

EXAMPLE 40

Preparation of Methyl 2-(difluoromethyl)-5-{[isopropylimino(methylthio)methyl]}-4-(2-methylpropyl)-6-(trifluoromethyl)-3-pyridinecarboxylate (Compound 58)

Reaction of methyl 5-chlorocarbonyl-2-(difluoromethyl)-4-(2-methylpropyl)-6-(trifluoromethyl)-3-pyridinecarboxylate (step 7 of U.S. Pat. No. 4,988,384) with isopropylamine yielded the corresponding isopropylamide. A mixture of this amide (3.75 g), 1.97 g of $PCl_5$ and 150 ml of carbon tetrachloride was held at reflux overnight and concentrated in vacuo. The residue was dissolved in 60 ml of THF and cooled to 5° C. and treated with 0.27 g of sodium methanethiolate. The reaction mixture was stirred at room temperature overnight, poured into water and extracted into ether. The organic was dried ($MgSO_4$), filtered, and concentrated in vacuo. The residue was purified by chromatotron (20% EtOAc in hexane) to give 1.0 g of pale yellow oil.

Compound 68 in Table 1 was similarly prepared except using methylamine instead of isopropylamine as a reagent.

EXAMPLE 41

Preparation of 3-Ethyl 5-Isopropyl 4-hydroxy-2-(trifluoromethyl)-3,5-pyridinedicarboxylate (Compound 101)

Ethyl 4-i-propoxy-2-(trifluoromethyl)-3-pyridinecarboxylate (prepared similar to step 2 of example 28) was reacted with 2 equivalents of lithium diisopropylamide as in step 3 of example 28 and quenched with dry ice instead of ethyl chloroformate. The reaction mixture was stirred at −78° C. for 15 min then warmed to room temperature in 1 h. The reaction mixture was poured into water and extracted with ether. The aqueous layer was acidified with concentrated HCl to give 3-ethyl 5-hydrogen 4-isopropoxy-2-(trifluoromethyl)-3,5-pyridinedicarboxylate as a solid, mp 97–99° C. A mixture of 10 g of this acid and 25 ml of thionyl chloride was held at reflux for 1 h and concentrated. The residue was held at reflux with 15 ml of isopropanol for 1 h and concentrated. The residue was kugelrohr distilled at 0.15 torr to give product as an oil, $n^{25}D$ 1.4620.

Compound 125 was similarly prepared except using ethanol instead of isopropanol as a reagent.

EXAMPLE 42

Preparation of Methyl 4-(Cyclopropylmethyl)-2-(difluoromethyl)-5-(1-hydroxy-5-methyl-3-pyrrolidinyl)-6-(trifluoromethyl)-3-pyridinecarboxylate (Compound 107)

To a solution of 16.5 g (68.3 mmol) of methyl 5-(1-cyano-3-butenyl)-4-(cyclopropylmethyl)-2-(difluoromethyl)-6-(trifluoromethyl)-3-pyridinecarboxylate (example 16 of U.S. Pat. No. 5,169,432) in 250 ml of ether cooled in an ice bath was added 91 ml (136 mmol) of diisobutylaluminum hydride (1.5 M in toluene). The reaction mixture was stirred on an ice bath for 30 min and was treated with 200 ml of 2.4 M HCl. The organic layer was washed with brine, dried ($MgSO_4$), and filtered through silica gel. The filtrate was concentrated in vacuo and the residue was purified by HPLC (17% EtOAc in hexane) to give 8.1 g of methyl 4-(cyclopropylmethyl)-2-(difluoromethyl)-5-(1-formyl-3-butenyl)-6-(trifluoromethyl)-3-pyridinecarboxylate.

To a solution of 5.8 g (14.8 mmol) of the above aldehyde in 100 ml of $Ccl_4$ was added 1.1 g (15.8 mmol) of hydroxylamine hydrochloride. To the mixture was added 10 g of pyridine and the mixture was heated to reflux for 1.5 h. The reaction mixture was partitioned between ether and 2.4 M HCl. The organic layer was washed with brine, dried ($MgSO_4$), and filtered through silica gel, and the filtrate was concentrated in vacuo. The residue was purified by HPLC (15% EtOAc in hexane) to yield 1.6 g of the oxime as white crystals, mp 98.5–101° C.

To a solution of 3.0 g (7.4 mmol) of the above oxime and 0.5 g (7.9 mmol) of sodium cyanoborohydride in 30 ml of methanol was added 3 mg of methyl orange. To the resulting solution was added dropwise a solution of conc. HCl and methanol (1:1) at a rate to maintain a reddish color (pH ~3.4). After the red color remained (1 h) the reaction mixture was partitioned between ether and 10% NaOH. The organic was washed with brine, dried ($MgSO_4$), and filtered through silica gel, and the filtrate was concentrated in vacuo. The residue was purified by HPLC (35% EtOAc in hexane) to give two fractions. The first fraction amounted to 0.8 g (27% yield) of crystals which was the desired product, mp 141.5–143.5° C. The second fraction amounted to 1.5 g (50% yield) of a colorless oil identified as the other diastereomer.

EXAMPLE 43

Preparation of Ethyl 4-Hydroxy-5-phenoxy-6-(trifluoromethyl)-3-pyridinecarboxylate (Compound 109)

Ethyl 2-(1-amino-2,2,2-trifluoroethylidien)-3-oxo-4-phenoxy-butanoate (example B1 of U.S. Pat. No. 4,936,905) was reacted according to the procedure in step 1 of Example 28 to give the product.

EXAMPLE 44

Preparation of Methyl 2-(difluoromethyl)-4-(2-methylpropyl)-5-(2-oxazolyl)-6-(trifluoromethyl)-3-pyridinecarboxylate (Compound 110)

This compound was prepared according to the procedure in example 4 of U.S. Pat. No. 4,988,384 except ethanolamine was used instead of glycine methyl ester hydrochloride.

EXAMPLE 45

Preparation of Methyl 5-(Chloroethylsulfinyl)-2-(difluoromethyl)-4-(2-methylpropyl)-6-(trifluoromethyl)-3-pyridinecarboxylate (Compound 111)

Oxidation of compound 44 with one equivalent of MCPBA according to the procedure in example 21 of U.S. Pat. No. 4,789,395 gave the product.

EXAMPLE 46

Preparation of Methyl 4-(Cyclopropylmethyl)-2-(difluoromethyl)-5-[imino(methylthio)methyl]-6-(trifluoromethyl)-3-pyridinecarboxylate (Compound 112)

Step 1: Methyl 5-(aminothioxomethy)-4-(Cyclopropylmethyl)-2-(difluoromethyl)-6-(trifluoromethyl)-3-pyridinecarboxylate.

Methyl 5-chlorocarbonyl-4-(cyclopropylmethyl)-2-(difluoromethyl)-6-(trifluoromethyl)-3-pyridinecarboxylate (example B3 of U.S. Pat. No. 5,156,670) was converted to methyl 4-(cyclopropylmethyl)-5-cyano-2-(difluoromethyl)-6-(trifluoromethyl)-3-pyridinecarboxylate by the procedure similar to example 88 and 92 of U.S. Pat. No. 4,692,184. A solution of 20 g (60 mmol) of this cyano compound and 0.62 g (6 mmol) of diethylamine in 60 ml of DMF was heated to 50° C. Hydrogen sulfide gas was introduced into this solution. When absorption of hydrogen sulfide was complete the reaction mixture was stirred at 50° C. for 1 h and poured into water and extracted with ether. The ether extract was washed with brine, dried ($MgSO_4$), and concentrated in vacuo. The residue was kugelrohr distilled to give 17.7 g (80% yield) of yellow oil.

Step 2: Methyl 4-(Cyclopropylmethyl)-2-(difluoromethyl)-5-[imino(methylthio)methyl]-6-(trifluoromethyl)-3-pyridinecarboxylate (Compound 112)

A solution of 3.7 g (10 mmol) of product of step 1 in 20 ml of methylene chloride was treated with 1.24 ml (11 mmol) of methyl trifluoromethylsulfonate. The reaction mixture as stirred under nitrogen at room temperature overnight and diluted with 80 ml of methylene chloride and washed with a saturated sodium bicarbonate solution. The methylene chloride solution was dried ($MgSO_4$), and concentrated in vacuo. The residue was purified by chromatography (EtOAc: hexane=1:5) to give 2.30 g (60%) of a yellow oil, $n^{25}D$ 1.5059.

Compound 90 in Table 1 was similarly prepared except using methyl 5-(chlorocarbonyl)-2-(difluoromethyl)-4-(2-methylpropyl)-6-(trifluoromethyl)-3-pyridinecarboxylate as the reagent.

EXAMPLE 47

Preparation of Ethyl 5-Ethoxy-4-Hydroxy-6-(trifluoromethyl)-3-pyridinecarboxylate (Compound 114)

Ethyl 3-amino-2-(2-ethoxy-1-oxo-ethyl)-4,4,4-trifluoro-2-butenoate (example A2 of U.S. Pat. No. 4,936,905) was reacted according to the procedure in step 1 of example 28 to give the product.

EXAMPLE 48

Methyl {-[2-Chloro-4-(trifluoromethyl)-5-thiazolyl] carbonylamino}-2-(difluoromethyl)-4-(2-methylpropyl)-6-(trifluoromethyl)-3-pyridinecarboxylate (Compound 117)

Methyl 5-amino-2-(difluoromethyl)-4-(2-methylpropyl)-6-(trifluoromethyl)-3-pyridinecarboxylate (example A1 of U.S. Pat. No. 5,114,465) was reacted with 2-chloro-4-(trifluoromethyl)-5-thiazolecarbonyl chloride according to the procedure in example 1 of U.S. Pat. No. 5,114,465 afforded the product.

EXAMPLE 49

Preparation of Methyl 5-(aminothioxomethyl)-4-(cyclobutyl)-2-(difluoromethyl)-6-(trifluoromethyl)-3-pyridinecarboxylate (Compound 119)

This compound was prepared from methyl 5-(chlorocarbonyl)-4-(cyclobutyl)-2-(difluoromethyl)-6-(trifluoromethyl)-3-pyridinecarboxylate according to the procedure in step 1 of Example 46.

Compound 103 in Table 2 was made similarly except using methyl 5-chlorocarbonyl-4-(2-methylpropyl)-2-(difluoromethyl)-6-(trifluoromethyl)-3-pyridinecarboxylate (step 7 of U.S. Pat. No. 4,988,384) as the starting material.

EXAMPLE 50

Preparation of 4-(4-Isopropylphenylthio)-5-methyl-6-(trifluoromethyl)-3-pyridinecarboxylic Acid (Compound 126)

Methyl 4-(4-isopropylphenylthio)-5-methyl-6-(trifluoromethyl)-3-pyridinecarboxylate (compound 11) was hydrolyzed with sodium hydroxide to give the product.

EXAMPLE 51

Methyl 5-(aminoethylthiocarbonyl)-2-(difluoromethyl)-4-(2-methylpropyl)-6-(trifluoromethyl)-3-pyridinecarboxylate (Compound 134)

Reaction of methyl 5-(chlorocarbonyl)-2-(difluoromethyl)-4-(2-methylpropyl)-6-(trifluoromethyl)-3-pyridine carboxylate (step 7 of U.S. Pat. No. 4,988,384) with 2-mercaptoethylamine similar to the procedure in example 140 of U.S. Pat. No. 4,692,184 gave the product.

EXAMPLE 52

Preparation of Methyl 5-(1-Bromo-2-methoxyethenyl)-4-(cyclopropylmethyl)-2-(difluoromethyl)-6-(trifluoromethyl)-3-pyridinecarboxylate (Compound 35)

To a solution of 18.0 g (49.3 mmol) of methyl 4-(cyclopropylmethyl)-2-(difluoromethyl)-5-(2-methoxyethenyl)-6-(trifluoromethyl)-3-pyridinecarboxylate (example 127 of U.S. Pat. No. 6,169,432) in 250 ml of ether was added 7.9 g (49.4 mmol) of bromine. The reaction mixture was stirred at room temperature for 2 h and to the mixture was added 6.8 g of freshly ground potassium carbonate and 100 ml of methanol. The reaction mixture was stirred for another 45 min and was washed with water and brine. The organic layer was dried (MgSO$_4$), filtered through celite, and concentrated in vacuo. The residue was kugelrohr distilled and the distillate was purified by chromatography (7% EtOAc in hexane) to give 18.7 g (80% yield) of 1:1 mixture of methyl 5-(1-bromo-2,2-dimethoxy-ethyl)-4-(cyclopropylmethyl)-2-(difluoromethyl)-6-(trifluoromethyl)-3-pyridinecarboxylate and product. HPLC purification (10% EtOAc in hexane) gave 4.1 g of the desired product as a colorless oil which crystallized and was recrystallized from hexane to give crystals, mp 79–79.5° C.

EXAMPLE 52

Preparation of Methyl 2-(Difluoromethyl)-5-[(dimethylaminothionothio)methyl]-6-(trifluoromethyl)-3-pyridinecarboxylate (Compound 43)

To a solution of 0.91 g (20 mmol) of dimethylamine in 6 ml of water and 0.92 g of 50% NaOH at 0° C. was added 0.95 g (12.5 mmol) of carbon disulfide. The reaction mixture was stirred for 1 h and to the reaction mixture was added a solution of 3.6 g (10 mmol) of 5-chloromethyl-2-(difluoromethyl)-4-(2-methylpropyl)-6-(trifluoromethyl)-3-pyridinecarboxylate (example 3 of U.S. Pat. No. 5,169,432) in 10 ml of acetone. The reaction mixture was quenched with water, extracted with methylene chloride, dried (MgSO$_4$), filtered through celite, and concentrated in vacuo. The residual brown solid was crystallized from ethyl acetate-hexane to give 3.21 g (72% yield) of product, mp 91–92° C.

EXAMPLE 53

Preparation of Methyl 2-(Difluoromethyl)-5-[(dimethylaminothionothio)methyl]-6-(trifluoromethyl)-3-pyridinecarboxylate (Compound 79)

This compound was made by the procedure similar to example 52 except gaseous carbonyl sulfide was used to replace carbon disulfide. The product was isolated as white power, mp 80–81° C.

BIOLOGICAL ACTIVITY EXAMPLES

EXAMPLE 54

CETP Activity In Vitro

The ability of compounds to inhibit CETP were assessed using an in vitro assay that measured the rate of transfer of radiolabeled cholesteryl ester ([$^3$H]CE) from HDL donor particles to LDL acceptor particles. Details of the assay are provided by Glenn et al. ("Quantification of Cholesteryl Ester Transfer Protein (CETP): A) CETP Activity and B) Immunochemical Assay of CETP Protein," *Meth. Enzymol.*, Glenn and Melton (Meth. Enzymol., 263, 339–351 (1996), which is incorporated herein by reference). CETP was obtained from the serum-free conditioned medium of CHO cells transfected with a cDNA for CETP (Wang, S. et al. *J. Biol Chem.* 267, 17487–17490 (1992), which is incorporated herein by reference).

To measure CETP activity, [$^3$H]CE-labeled HDL, LDL, CETP and assay buffer (50 mM tris(hydroxymethyl)aminomethane, pH 7.4; 150 mM sodium chloride; 2 mM ethylenediamine-tetraacetic acid; 1% bovine serum albumin) were incubated in a volume of 200 μl, for 2 hours at 37° C. in 96 well plates. LDL was differentially precipitated by the addition of 50 μl of 1% (w/v) dextran sulfate/0.5 M magnesium chloride, mixed by vortex, and incubated at room temperature for 10 minutes The solution (200μl) was transferred to a filter plate (Millipore). After filtration, the radioactivity present in the precipitated LDL was measured by liquid scintillation counting. Correction for non-specific transfer or precipitation was made by including samples that did not contain CETP. The rate of [$^3$H]CE transfer using this assay was linear with respect to time and CETP concentration, up to 25–30% of [$^3$H]CE transferred.

The potency of test compounds was determined by performing the above described assay in the presence of varying concentrations of the test compounds and determining the concentration required for 50% inhibition of transfer of [$^3$H]CE from HDL to LDL. This value was defined as the IC$_{50}$. The IC$_{50}$ values determined by this method for the substituted pyridine compounds of the invention are specified in Tables 1–8.

EXAMPLE 55

Whole Serum CETP Activity Assay (Tritiated Cholesterol Ester)

Blood was obtained from healthy volunteers recruited from the personnel of Monsanto Company, Saint Louis, Mo. Blood was either collected in tubes containing EDTA (EDTA plasma pool) or in tubes without EDTA (spun to form the serum pool). The EDTA human plasma pool or human serum pool, previously stored at −20° C., was thawed at room temperature, and centrifuged for 5 minutes to remove any particulate matter. Tritiated HDL, radiolabeled in the cholesteryl ester moiety ([$^3$H]CE-HDL) as described by Morton and Zilversmit (J. Biol. Chem., 256, 11992–95 (1981) which is incorporated by reference herein), was added to the plasma or serum to a final concentration of (25 μg/ml cholesterol).

Inhibitor compounds were added to the plasma or serum as follows: Equal volumes of the plasma or serum containing the [$^3$H]CE-HDL (396 μl) were pipetted into micro tubes (Titertube®, Bio-Rad Laboratories, Hercules, Calif.). Compounds, usually dissolved as 20–50 mM stock solutions in DMSO, were serially diluted in DMSO (or an alternative solvent in some cases, such as dimethylformamide or ethanol). Four μl of each of the serial dilutions of inhibitor compounds or DMSO alone were then added to each of the plasma or serum tubes. The tubes were immediately mixed. Triplicate aliquots (100 μl) from each plasma or serum tube were then transferred to wells of 96-well round-bottomed polystyrene microtiter plates (Corning, Corning, N.Y.). Plates were sealed with plastic film and incubated at 37° C. for 4 hours.

Test wells contained plasma or serum with dilutions of inhibitor compounds. Control wells contained plasma or serum with DMSO alone. Blank wells contained plasma or serum with DMSO alone that were left in the micro tubes at 4° C. for the 4 hour incubation and were added to the microtiter wells at the end of the incubation period. VLDL and LDL were precipitated by the addition of 10 µl of precipitating reagent (1% (w/v) Dextran Sulfate (Dextralip50)/0.5M magnesium chloride, pH 7.4) to all wells. The wells were mixed on a plate mixer and then incubated at ambient temperature for 10 min. The plates were then centrifuged at 1000×g for 30 mins at 10° C. The supernatants (50 µl) from each well were then transferred to Picoplate™ 96 plate wells (Packard, Meriden, Conn.) containing 250:1 Microscint™-40 (Packard, Meriden, Conn.). The plates were heat-sealed (TopSeal™-P, Packard, Meriden, Conn.) according to the manufacturers directions and mixed for 30 min.

Radioactivity was measured on a microplate scintillation counter (TopCount, Packard, Meriden, Conn.). $IC_{50}$'s were determined as the concentration of inhibitor compound inhibiting transfer of [$^3$H]CE from the supernatant [$^3$H]CE-HDL to the precipitated VLDL and LDL by 50% compared to the transfer obtained in the control wells. The maximum percent transfer (in the control wells) was determined using the following equation:

$$\% \text{ Transfer} = \frac{[dpm_{blank} - dpm_{control}] \times 100}{dpm_{blank}}$$

The percent of control transfer determined in the wells containing inhibitor compounds was determined as follows:

$$\% \text{ Control} = \frac{[dpm_{blank} - dpm_{test}] \times 100}{dpm_{blank} - dpm_{control}}$$

$IC_{50}$ values were then calculated from plots of % control versus concentration of inhibitor compound. The $IC_{50}$ values of the substituted pyridine compounds determined by this method are as follows: Compound 7, 17 micromolar; Compound 180, 9 micromolar; Compound 181, 16 micromolar; Compound 214, 70 micromolar; and Compound 215, 110 micromolar.

EXAMPLE 56
Inhibition of CETP Activity In Vivo

Inhibition of CETP by a test compound can be determined by administering the compound to an animal by intravenous injection, determining the rate of transfer of tritium-labeled cholesteryl ester ($^3$H]CE) from HDL to VLDL and LDL particles, and comparing the rate of transfer with the rate of transfer observed in control animals.

Male golden Syrian hamsters were maintained on a diet of chow containing 0.24% cholesterol for at least two weeks prior to the study. Immediately before the experiment, animals were anesthetized with pentobarbital. Anesthesia was maintained throughout the experiment. Indwelling catheters were inserted into the jugular vein and carotid artery. Test compound, Dimethyl 5,5'-dithiobis[2-difluoromethyl)-4-(2-methylpropyl)-6-(trifluoromethyl)-3-pyridinecarboxylate] (Compound 181), was dissolved as a 80 mM stock solution in vehicle (2% ethanol: 98% PEG 400, Sigma Chemical Company, St. Louis, Mo., USA). At the start of the experiment all animals received 0.2 ml of a solution containing [$^3$H]-CE-HDL into the jugular vein. [$^3$H[-CE-HDL is a preparation of human HDL containing tritium-labeled cholesteryl ester, and was prepared according to the method of Glenn et al. ("Quantification of Cholesteryl Ester Transfer Protein (CETP): A) CETP Activity and B) Immunochemical Assay of CETP Protein," *Meth. Enzymol.*, Glenn and Melton (Meth. Enzymol., 263, 339–351 (1996) which is incorporated herein by reference).

After 2 minutes, the animals received 0.1 ml of the test solution injected into the jugular vein. Control animals received 0.1 ml of the vehicle solution without test compound. After 5 minutes, the first blood samples (0.5 ml) were taken from the carotid artery and collected in standard microtainer tubes containing ethylenediamine tetraacetic acid. Saline (0.5 ml) was injected to flush the catheter and replace blood volume. Subsequent blood samples were taken at two hours and four hours by the same method. Blood samples were mixed well and kept on ice until the completion of the experiment.

Plasma was obtained by centrifugation of the blood samples at 4° C. The plasma (50 µl) was then treated with 5 µl of precipitating reagent (dextran sulfate, 10 g/l; 0.5M magnesium chloride to remove VLDL/LDL. After centrifugation, the resulting supernatant (25 µl) containing the HDL was analyzed for radioactivity using a liquid scintillation counter. The percentage [$^3$H] CE transferred from HDL to LDL and VLDL (% transfer) was calculated based on the total radioactivity in equivalent serum samples before precipitation. Typically, the amount of transfer from HDL to LDL and VLDL in control animals was 30 to 35% after four hours. The polyethylene glycol vehicle was determined to have no effect on CETP activity in this model.

Table 14 shows the results of an experiment utilizing five animals that received Dimethyl 5,5'-dithiobis[2-difluoromethyl)-4-(2-methylpropyl)-6-(trifluoromethyl)-3-pyridinecarboxylate] (Compound 181), and five animals that received vehicle. At two hours, mean values of 13% [$^3$H]-Ce transfer from HDL to LDL and VLDL were obtained for the control animals, but only 4.7% transfer for the animals receiving Compound 181. This represents a 64% inhibition of CETP activity. Student t-tests were performed to determine if the means for control and animals treated with Compound 181 were statistically different. Values of p<0.01 for both sets of data indicate that the differences are highly significant.

TABLE 14

|  | % Transfer | | % Inhibition | |
| --- | --- | --- | --- | --- |
|  | Control | Compound 181 | Compound 181 | t-Test |
| Two Hours | 13 | 4.7 | 63.6 | 0.008 |
| Four hours | 21.6 | 10.6 | 50.8 | 0.001 |

Similarly, in separate experiments a mean of 21.6% [$^3$H]-CE transfer was obtained for the control animals at four hours, but only 10.6% was transferred in animals treated with methyl 2-(difluoromethyl)-5-mercapto-4-(2-methylpropyl)-6-(trifluoromethyl)-3-pyridinecarboxylate (Compound 7), representing a 50% inhibition of CETP activity.

EXAMPLE 57
Chronic Inhibition of CETP Activity In Vivo

Chronic inhibition of CETP can be achieved by administration of Dimethyl 5,5'-dithiobis[2-difluoromethyl)-4-(2-methylpropyl)-6-(trifluoromethyl)-3-pyridinecarboxylate] (Compound 181) to hamsters using Alzet pump delivery of Compound 181 into the jugular veins of hamsters. Inhibition of CETP should lead to an increase in HDL cholesterol with a concomitant decrease in LDL cholesterol. This can be determined by filtering serum obtained at different time intervals after initiation of inhibitor infusion and quantitating the amount of cholesterol in the LDL and HDL peaks, respectively. In addition the activity of CETP in the serum can be assessed in an ex vivo CETP activity assay.

Male golden Syrian hamsters were maintained on a diet of normal rodent chow enriched with 0.24% cholesterol for at least 2 weeks prior to study. On Day 1, the hamsters were anesthetized with pentobarbital. An indwelling catheter was inserted into the jugular vein and exteriorized onto the back of the neck. The hamsters received 100 μ of Compound 181 (38.5 mg/kg) in a 2% ethanol:98% PEG400 vehicle, or the 2% ethanol:98% PEG400 vehicle alone. An Alzet pump was then attached to the jugular catheter which delivered a steady infusion of 24 μl/day for a dose of 1.3 mg/day(9.2 mg/kg/day). The hamsters received the vehicle (2% ETOH:98% PEG400) or Compound 181 for 8 days. The hamsters were maintained for 12 days. Blood samples were taken on day 1 (pre-bleed) at the time of surgery, and on days 5, 7, 8 and 12. Fast Protein Liquid Chromatography (FPLC) on tandem Superose 6 columns of pooled hamster serum was performed to obtain cholesterol profiles for the two experimental groups.

Table 15 shows the results of an experiment utilizing 5 hamsters in each group, vehicle and Compound 181. Serum cholesterol profiles were determined on pooled sera from each group. Total serum cholesterol and CETP activity were determined on individual serum samples. In hamsters administered Compound 181 chronically, there was a 30% reduction and 26% increase in LDL cholesterol and HDL cholesterol concentrations, respectively, compared to the vehicle group at Day 5. The decrease in LDL and increase in HDL persisted until Day 8 when the Alzet pump was exhausted. At Day 12, LDL cholesterol concentrations began to rise and HDL cholesterol concentrations started to decrease toward the concentrations in the vehicle group (90% and 114% of vehicle group, respectively). It should be noted that an average 10% reduction in CETP activity was determined by ex vivo assay on Days 5 and 8 with a return to vehicle control level by day 12. Therefore, it would appear that for every percent reduction in CETP activity determined by the ex vivo assay, there was a 2–3% decrease in LDL cholesterol or increase in HDL cholesterol concentrations.

TABLE 15

Cholesterol Concentrations In Compound 181
% Cholesterol Concentration In Vehicle Group

| DAY | LDL | HDL |
| --- | --- | --- |
| Day 1 | 111% | 105% |
| Day 5 | 70% | 126% |
| Day 8 | 75% | 115% |
| Day 12 | 90% | 114% |

The foregoing biological data demonstrate that administration of the substituted pyridine inhibitors of the present invention produces inhibition of CETP-mediated lipid transfer in vivo.

All mentioned references are incorporated by reference as if here written.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

What is claimed is:

1. A method for inhibiting the activity of cholesteryl ester transfer protein in vivo by administering to a subject a therapeutically-effective amount of a compound, a tautomer of the compound, or a pharmaceutically-acceptable salt of the compound or tautomer, wherein:

the compound corresponds in structure to Formula I:

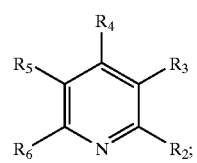

(I)

$R_2$ and $R_6$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl;

at least one of $R_2$ and $R_6$ is fluorinated alkyl, chlorofluorinated alkyl, or alkoxyalkyl;

$R_3$ is selected from the group consisting of amido, arylcarbonyl, heteroarylcarbonyl, —CHO, and —$CO_2R_7$;

$R_7$ is selected from the group consisting of hydrogen, alkyl, and cyanoalkyl;

$R_4$ is selected from the group consisting of thiol, alkylthio, alkenylthio, alkynylthio, arylthio, heteroarylthio, heterocyclylthio, cycloalkylthio, cycloalkenylthio, and —$SO_2R_9$;

$R_9$ is selected from the group consisting of hydroxy, alkyl, alkenyl, alkynyl, aryl, heteroaryl, and heterocyclyl;

$R_5$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, alkoxy, alkenoxy, alkynoxy, aryloxy, heteroaryloxy, heterocyclyloxy, alkylcarbonyloxyalkyl, alkenylcarbonyloxyalkyl, alkynylcarbonyloxyalkyl, arylcarbonyloxyalkyl, heteroarylcarbonyloxyalkyl, heterocyclylcarbonyloxyalkyl, cycloalkylalkyl, cycloalkenylalkyl, aralkyl, heteroarylalkyl, heterocyclylalkyl (other than δ-lactone-alkyl), cycloalkylalkenyl, cycloalkenylalkenyl, aralkenyl, heteroarylalkenyl, heterocyclylalkenyl (other than δ-lactone-alkenyl), alkylthioalkyl, cycloalkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkoxyalkyl, alkenoxyalkyl, alkynoxyalkyl, aryloxyalkyl, heteroaryloxyalkyl, heterocyclyloxyalkyl, alkoxyalkenyl, alkenoxyalkenyl, alkynoxyalkenyl, aryloxyalkenyl, heteroaryloxyalkenyl, heterocyclyloxyalkenyl, cyano, hydroxymethyl, —$CO_2R_{14}$,

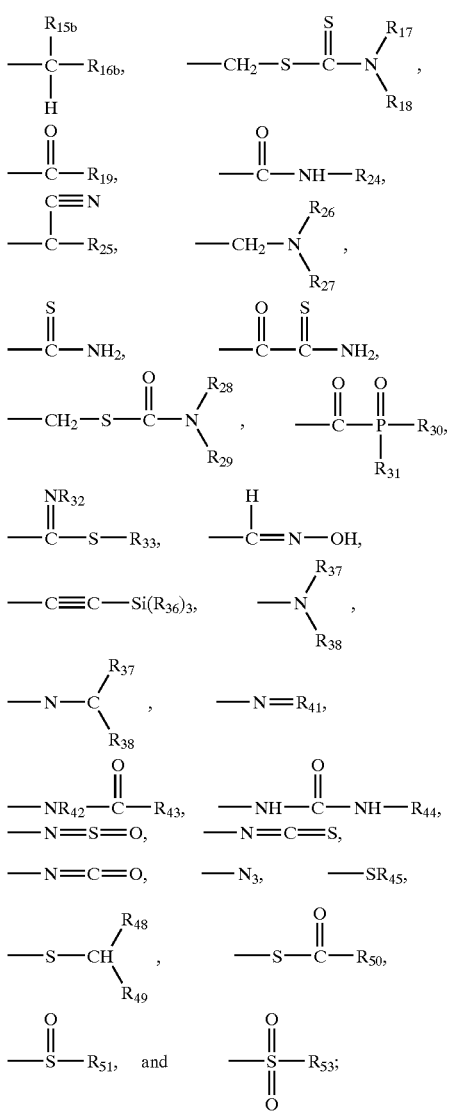

$R_{14}$ is selected from the group consisting of alkyl, alkenyl, alkynyl, aryl, heteroaryl, and heterocyclyl;

$R_{15b}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy, heterocyclyloxy, aroyloxy, and alkylsulfonyloxy;

$R_{16b}$ is selected from the group consisting of alkyl, alkenyl, alkynyl, aryl, heteroaryl, heterocyclyl, arylalkoxy, and trialkylsilyloxy;

$R_{17}$ and $R_{18}$ are independently selected from the group consisting of alkyl, cycloalkyl, alkenyl, alkynyl, aryl, heteroaryl, and heterocyclyl;

$R_{19}$ is selected from the group consisting of alkyl, cycloalkyl, alkenyl, alkynyl, aryl, heteroaryl, heterocyclyl, —$SR_{20}$, —$OR_{21}$, and —$R_{22}CO_2R_{23}$;

$R_{20}$ is selected from the group consisting of alkyl, alkenyl, alkynyl, aryl, heteroaryl, heterocyclyl, aminoalkyl, aminoalkenyl, aminoalkynyl, aminoaryl, aminoheteroaryl, aminoheterocyclyl, alkylheteroarylamino, and arylheteroarylamino;

$R_{21}$ is selected from the group consisting of alkyl, alkenyl, alkynyl, aryl, heteroaryl, and heterocyclyl;

$R_{22}$ is selected from the group consisting of alkylene and arylene;

$R_{23}$ is selected from the group consisting of alkyl, alkenyl, alkynyl, aryl, heteroaryl, and heterocyclyl;

$R_{24}$ is selected from the group consisting of hydrogen, alkyl, cycloalkyl, alkenyl, alkynyl, aryl, heteroaryl, heterocyclyl, aralkyl, aralkenyl, and aralkynyl;

$R_{25}$ is heterocyclylidenyl;

$R_{26}$ and $R_{27}$ are independently selected from the group consisting of hydrogen, alkyl, cycloalkyl, alkenyl, alkynyl, aryl, heteroaryl, and heterocyclyl;

$R_{28}$ and $R_{29}$ are independently selected from the group consisting of hydrogen, alkyl, cycloalkyl, alkenyl, alkynyl, aryl, heteroaryl, and heterocyclyl;

$R_{30}$ and $R_{31}$ are independently selected from the group consisting of alkoxy, alkenoxy, alkynoxy, aryloxy, heteroaryloxy, and heterocyclyloxy;

$R_{32}$ and $R_{33}$ are independently selected from the group consisting of hydrogen, alkyl, cycloalkyl, alkenyl, alkynyl, aryl, heteroaryl, and heterocyclyl;

each $R_{36}$ is independently selected from the group consisting of alkyl, alkenyl, aryl, heteroaryl, and heterocyclyl;

$R_{37}$ and $R_{38}$ are independently selected from the group consisting of hydrogen, alkyl, cycloalkyl, alkenyl, alkynyl, aryl, heteroaryl, and heterocyclyl;

$R_{39}$ is selected from the group consisting of hydrogen, alkoxy, alkenoxy, alkynoxy, aryloxy, heteroaryloxy, heterocyclyloxy, alkylthio, alkenylthio, alkynylthio, arylthio, heteroarylthio, and heterocyclylthio;

$R_{40}$ is selected from the group consisting of haloalkyl, haloalkenyl, haloalkynyl, haloaryl, haloheteroaryl, haloheterocyclyl, cycloalkyl, cycloalkenyl, heterocyclylalkoxy, heterocyclylalkenoxy, heterocyclylalkynoxy, alkylthio, alkenylthio, alkynylthio, arylthio, heteroarylthio, and heterocyclylthio;

$R_{41}$ is heterocyclylidenyl;

$R_{42}$ is selected from the group consisting of hydrogen, alkyl, alkenyl, alkynyl, aryl, heteroaryl, and heterocyclyl;

$R_{43}$ is selected from the group consisting of hydrogen, alkyl, alkenyl, alkynyl, aryl, heteroaryl, heterocyclyl, cycloalkyl, cycloalkenyl, haloalkyl, haloalkenyl, haloalkynyl, haloaryl, haloheteroaryl, and haloheterocyclyl;

$R_{44}$ is selected from the group consisting of hydrogen, alkyl, cycloalkyl, alkenyl, alkynyl, aryl, heteroaryl, and heterocyclyl;

$R_{45}$ is selected from the group consisting of hydrogen, alkyl, alkenyl, alkynyl, aryl, heteroaryl, heterocyclyl, haloalkyl, haloalkenyl, haloalkynyl, haloaryl, haloheteroaryl, haloheterocyclyl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, aminocarbonylalkyl, aminocarbonylalkenyl, aminocarbonylalkynyl, aminocarbonylaryl, aminocarbonylheteroaryl, aminocarbonylheterocyclyl, —$SR_{46}$, and —$CH_2R_{47}$;

$R_{46}$ is selected from the group consisting of alkyl, alkenyl, alkynyl, aryl, heteroaryl, and heterocyclyl;

$R_{47}$ is selected from the group consisting of hydrogen, alkyl, alkenyl, alkynyl, aryl, heteroaryl, and heterocyclyl;

$R_{48}$ is selected from the group consisting of hydrogen, alkyl, cycloalkyl, alkenyl, alkynyl, aryl, heteroaryl, and heterocyclyl;

$R_{49}$ is selected from the group consisting of alkoxy, alkenoxy, alkynoxy, aryloxy, heteroaryloxy, heterocyclyloxy, haloalkyl, haloalkenyl, haloalkynyl, haloaryl, haloheteroaryl, and haloheterocyclyl;

$R_{50}$ is selected from the group consisting of hydrogen, alkyl, cycloalkyl, alkenyl, alkynyl, aryl, heteroaryl, heterocyclyl, alkoxy, alkenoxy, alkynoxy, aryloxy, heteroaryloxy, and heterocyclyloxy;

$R_{51}$ is selected from the group consisting of alkyl, alkenyl, alkynyl, aryl, heteroaryl, heterocyclyl, haloalkyl, haloalkenyl, haloalkynyl, haloaryl, haloheteroaryl, and haloheterocyclyl;

$R_{53}$ is selected from the group consisting of alkyl, alkenyl, alkynyl, aryl, heteroaryl, and heterocyclyl;

except to the extent otherwise stated, the term alkyl, alone or in combination with other terms, encompasses both unsubstituted and substituted alkyl;

except to the extent otherwise stated, the term alkenyl, alone or in combination with other terms, encompasses both unsubstituted and substituted alkenyl;

except to the extent otherwise stated, the term alkynyl, alone or in combination with other terms, encompasses both unsubstituted and substituted alkynyl;

except to the extent otherwise stated, the term aryl, alone or in combination with other terms, encompasses both unsubstituted and substituted aryl;

except to the extent otherwise stated, the term heteroaryl, alone or in combination with other terms, encompasses both unsubstituted and substituted heteroaryl;

except to the extent otherwise stated, the term heterocyclyl, alone or in combination with other terms, encompasses both unsubstituted and substituted heterocyclyl; and except to the extent otherwise stated, the term cycloalkyl, alone or in combination with other terms, encompasses both unsubstituted and substituted cycloalkyl.

2. The method of claim 1, wherein:

$R_2$ and $R_6$ are independently selected from the group consisting of hydrogen, hydroxy, alkyl, fluorinated alkyl, chlorofluorinated alkyl, cycloalkyl, heterocyclyl, aryl, heteroaryl, alkoxy, alkoxyalkyl, and alkoxycarbonyl;

$R_3$ is selected from the group consisting of amido, arylcarbonyl, heteroarylcarbonyl, and —$CO_2R_7$;

$R_4$ is selected from the group consisting of thiol, alkylthio, arylthio, cycloalkylthio, heterocyclylthio, and —$SO_2R_9$;

$R_9$ is aryl;

$R_5$ is selected from the group consisting of hydrogen, hydroxy, halogen, alkyl, haloalkyl, alkynyl, heterocyclyl, heteroaryl, alkoxy, aryloxy, arylcarbonyloxyalkyl, heterocyclylalkyl (other than δ-lactone-alkyl and heterocyclyl-ethyl), alkylthioalkyl, arylthioalkyl, heteroarylthioalkyl, alkoxyalkenyl, cyano, hydroxymethyl, —$CO_2R_{14}$,

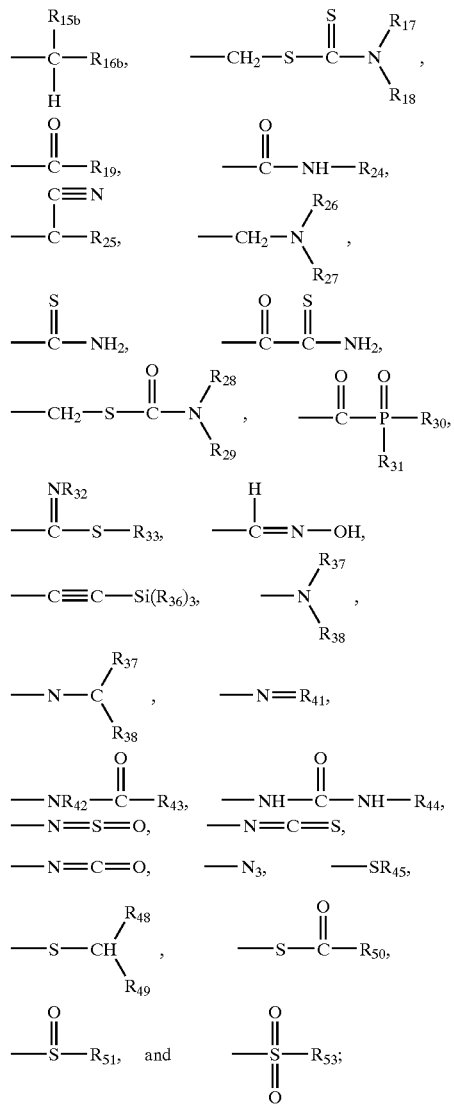

$R_{14}$ is alkyl;

$R_{15b}$ is selected from the group consisting of hydroxy, hydrogen, halogen, alkylthio, and alkoxy;

$R_{16b}$ is selected from the group consisting of alkyl, aryl, and heteroaryl;

$R_{17}$ and $R_{18}$ are independently selected alkyl;

$R_{19}$ is selected from the group consisting of aryl, heteroaryl, —$SR_{20}$, —$OR_{21}$, and —$R_{22}CO_2R_{23}$;

$R_{20}$ is selected from the group consisting of alkyl, aryl, and aminoalkyl;

$R_{21}$ is aryl;

$R_{22}$ is alkylene;

$R_{23}$ is alkyl;

$R_{24}$ is selected from the group consisting of hydrogen, unsubstituted alkyl, and aralkyl;

$R_{26}$ and $R_{27}$ are independently selected alkyl;

$R_{28}$ and $R_{29}$ are independently selected alkyl;

$R_{30}$ and $R_{31}$ are independently selected alkoxy;

$R_{32}$ is selected from the group consisting of hydrogen and alkyl;

$R_{33}$ is alkyl;

each $R_{36}$ is independently selected alkyl;

$R_{37}$ and $R_{38}$ are independently selected alkyl;

$R_{39}$ is selected from the group consisting of hydrogen, alkoxy, and alkylthio;

$R_{40}$ is selected from the group consisting of haloalkyl, cycloalkyl, heterocyclylalkoxy, and alkylthio;

$R_{42}$ is selected from the group consisting of hydrogen and alkyl;

$R_{43}$ is selected from the group consisting of cycloalkyl, chlorinated alkyl, and substituted heteroaryl;

$R_{44}$ is heteroaryl;

$R_{45}$ is selected from the group consisting of hydrogen, alkyl, haloalkyl, heterocyclyl, aralkyl, heteroaralkyl, alkylthioalkyl, aminocarbonylalkyl, —$SR_{46}$, and —$CH_2R_{47}$;

$R_{46}$ is selected from the group consisting of aryl and heteroaryl;

$R_{47}$ is selected from the group consisting of aryl and heteroaryl;

$R_{48}$ is selected from the group consisting of hydrogen and alkyl;

$R_{49}$ is selected from the group consisting of alkoxy and haloalkyl;

$R_{50}$ is selected from the group consisting of alkyl, alkoxy, aryl, and heteroaryl;

$R_{51}$ is selected from the group consisting of haloalkyl and alkyl; and $R_{53}$ is aryl.

3. The method of claim 1, wherein:

when $R_2$ is difluoromethyl, $R_3$ is —$CO_2CH_3$, $R_5$ is

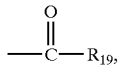

$R_6$ is trifluoromethyl, and $R_{19}$ is pyrazolyl, then:

$R_4$ is selected from the group consisting of thiol, alkylthio, arylthio, cycloalkylthio, heterocyclylthio, and alkylthioalkyl, trialkylsilyl, —OC(O)N($R_8$)$_2$, —$SO_2R_9$;

when $R_2$ is difluoromethyl, $R_3$ is —$CO_2CH_3$, $R_5$ is 2-(4,5-dihydro-oxazolyl), and $R_6$ is trifluoromethyl, then:

$R_4$ is selected from the group consisting of thiol, alkylthio, arylthio, cycloalkylthio, heterocyclylthio, and —$SO_2R_9$;

when $R_2$ and $R_6$ are independently fluorinated methyl, $R_3$ is —$CO_2R_7$, $R_5$ is cyano, and $R_7$ is selected from the group consisting of hydrogen and alkyl, then:

$R_4$ is selected from the group consisting of thiol, alkylthio, arylthio, cycloalkylthio, heterocyclylthio, and —$SO_2R_9$;

when $R_2$ is methyl, $R_3$ is —$CO_2C_2H_5$, $R_5$ is

$R_6$ is methyl, and $R_{24}$ is aralkyl, then:

$R_4$ is selected from the group consisting of thiol, alkylthio, arylthio, cycloalkylthio, heterocyclylthio, and —$SO_2R_9$;

when $R_2$ is selected from the group consisting of methyl, difluoromethyl, and trifluoromethyl, $R_3$ is —$CO_2CH_3$, $R_5$ is hydrogen, and $R_6$ is selected from the group consisting of methyl and trifluoromethyl, then:

$R_4$ is selected from the group consisting of thiol, alkylthio, arylthio, cycloalkylthio, heterocyclylthio, and —$SO_2R_9$; and when $R_2$ is trifluoromethyl, $R_3$ is selected from the group consisting of —$CO_2H$ and —$CO_2C_2H_5$, $R_5$ is methyl, and $R_6$ is selected from the group consisting of hydrogen and trifluoromethyl, then:

$R_4$ is selected from the group consisting of thiol, alkylthio, arylthio, cycloalkylthio, heterocyclylthio and —$SO_2R_9$.

4. The method of claim 2, wherein:

$R_2$ is selected from the group consisting of methyl and fluorinated methyl;

$R_3$ is —$CO_2R_7$; and $R_7$ is selected from the group consisting of hydrogen, methyl, and ethyl.

5. The method of claim 2, wherein:

$R_2$ is fluorinated alkyl;

$R_3$ is —$CO_2R_7$;

$R_7$ is selected from the group consisting of hydrogen and alkyl;

$R_5$ is selected from the group consisting of pyrrolyl,

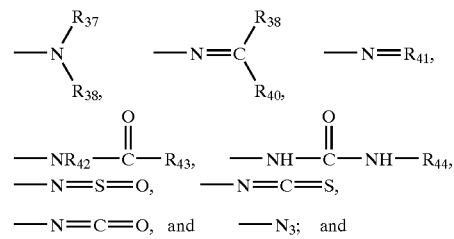

$R_6$ is fluorinated alkyl.

6. The method of claim 2, wherein:

$R_2$ is fluorinated alkyl;

$R_3$ is —$CO_2R_7$;

$R_7$ is selected from the group consisting of hydrogen and alkyl;

$R_4$ is alkylthio;

$R_5$ is selected from the group consisting of:

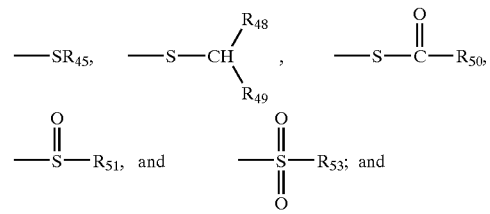

$R_6$ is fluorinated alkyl.

7. The method of claim 2, wherein:

$R_2$ is selected from the group consisting of alkyl and fluorinated alkyl;

$R_3$ is —$CO_2R_7$;

$R_7$ is selected from the group consisting of hydrogen and alkyl;

$R_4$ is selected from the group consisting of alkylthio, arylthio and —$SO_2R_9$;

R₅ is selected from the group consisting of hydrogen, hydroxy, halogen, alkoxy, and aryloxy; and R₆ is selected from the group consisting of hydrogen, fluorinated alkyl, and alkoxycarbonyl.

8. The method of claim 2, wherein:

R₂ is fluorinated alkyl;

R₃ is —CO₂R₇;

R₄ is arylthio;

R₅ is selected from the group consisting of alkyl, haloalkyl, alkynyl, heterocyclyl, heteroaryl, heterocyclylalkyl, arylcarbonyloxyalkyl, alkylthioalkyl, arylthioalkyl, heteroarylthioalkyl, alkoxyalkenyl, cyano,

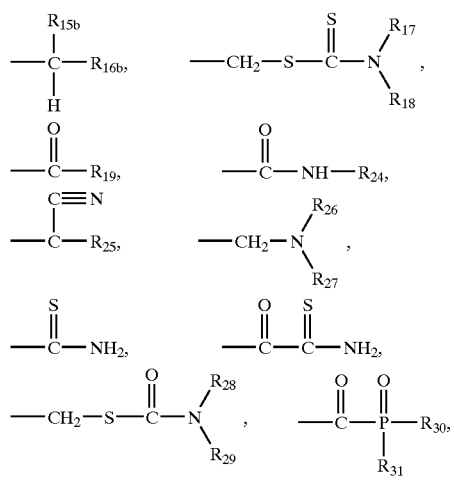

R₁₅ᵦ is selected from the group consisting of hydroxy, alkylthio, and alkoxy;

R₁₆ᵦ is selected from the group consisting of alkyl and heteroaryl; and

R₆ is selected from the group consisting of hydrogen, fluorinated alkyl, and alkoxy.

9. The method of claim 2, wherein:

R₂ is selected from the group consisting of hydroxy, alkyl, fluorinated alkyl, and alkoxyalkyl;

R₃ is selected from the group consisting of amido and —CO₂R₇;

R₇ is selected from the group consisting of hydrogen and alkyl;

R₄ is selected from the group consisting of thiol, alkylthio, cycloalkylthio, and heterocyclylthio;

R₅ is CO₂R₁₄; and

R₆ is selected from the group consisting of hydrogen, hydroxy, alkyl, fluorinated alkyl, and alkoxyalkyl.

10. The method of claim 2, wherein:

R₂ is selected from the group consisting of alkyl and fluorinated alkyl;

R₃ is —CO₂R₇;

R₇ is selected from the group consisting of hydrogen and alkyl;

R₄ is selected from the group consisting of thiol, arylthio, and heterocyclylthio;

R₅ is selected from the group consisting of alkyl, heterocyclyl, arylthioalkyl, heteroarylthioalkyl, —CO₂R₁₄,

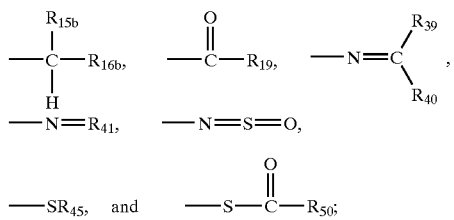

R₁₅ᵦ is hydroxy;

R₁₆ᵦ is heteroaryl;

R₁₉ is —SR₂₀;

R₂₀ is alkyl;

R₃₉ is alkoxy;

R₄₀ is haloalkyl;

R₄₅ is selected from the group consisting of hydrogen, —SR₄₆, and —CH₂R₄₇;

R₅₀ is selected from the group consisting of alkyl and alkoxy; and

R₆ is selected from the group consisting of alkyl and fluorinated alkyl.

11. The method of claim 2, wherein the compound is selected from the group consisting of 5 ethyl 3-methyl-2-(difluoromethyl)-4-[(4,5-dihydro-2-thiazolyl)thio]-6-(trifluoromethyl)-3,5-pyridinedicarboxylate; and methyl 4-(4-i-propylphenylthio)-5-methyl-6-(trifluoromethyl)-3-pyridinecarboxylate.

12. The method of claim 1, wherein the compound corresponds in structure to the following formula:

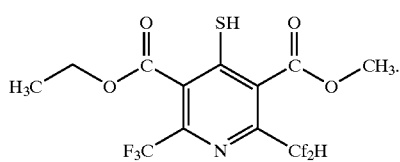

13. The method of claim 1, wherein the compound corresponds in structure to a formula selected from the group consisting of:

14. The method of claim 1, wherein the compound corresponds in structure to a formula selected from the group consisting of:

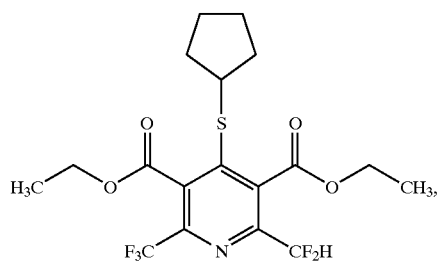
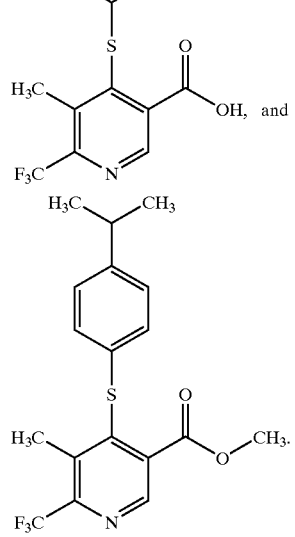
* * * * *